US010947582B2

(12) United States Patent
Myers et al.

(10) Patent No.: US 10,947,582 B2
(45) Date of Patent: Mar. 16, 2021

(54) METHODS OF NUCLEIC ACID SAMPLE PREPARATION FOR IMMUNE REPERTOIRE SEQUENCING

(71) Applicant: ArcherDX, LLC, San Francisco, CA (US)

(72) Inventors: Jason Myers, Boulder, CO (US); Joshua Stahl, Boulder, CO (US); Brady Culver, Aliso Viejo, CA (US); Brian Kudlow, Boulder, CO (US); Jens Eberlein, Boulder, CO (US)

(73) Assignee: ArcherDX, LLC, San Francisco, CA (US)

( * ) Notice: Subject to any disclaimer, the term of this patent is extended or adjusted under 35 U.S.C. 154(b) by 250 days.

(21) Appl. No.: 15/802,408

(22) Filed: Nov. 2, 2017

(65) Prior Publication Data

US 2018/0155767 A1  Jun. 7, 2018

Related U.S. Application Data

(60) Provisional application No. 62/416,677, filed on Nov. 2, 2016.

(51) Int. Cl.
| | | |
|---|---|---|
| *C12Q 1/68* | (2018.01) | |
| *C12Q 1/6813* | (2018.01) | |
| *A61P 35/02* | (2006.01) | |
| *C07K 16/28* | (2006.01) | |
| *C12N 15/09* | (2006.01) | |
| *C12Q 1/6806* | (2018.01) | |
| *C12Q 1/6869* | (2018.01) | |
| *C07D 495/04* | (2006.01) | |

(52) U.S. Cl.
CPC ............ *C12Q 1/6813* (2013.01); *A61P 35/02* (2018.01); *C07K 16/2809* (2013.01); *C12N 15/09* (2013.01); *C12Q 1/6806* (2013.01); *C07D 495/04* (2013.01); *C07K 2319/32* (2013.01); *C12Q 1/6869* (2013.01)

(58) Field of Classification Search
CPC ............... C12Q 1/6806; C12Q 1/6813; C07K 16/2809
See application file for complete search history.

(56) References Cited

U.S. PATENT DOCUMENTS

| | | | |
|---|---|---|---|
| 5,374,524 A | 12/1994 | Miller | |
| 5,827,658 A | 10/1998 | Liang | |
| 6,818,395 B1 | 11/2004 | Quake et al. | |
| 6,911,345 B2 | 6/2005 | Quake et al. | |
| 7,169,560 B2 | 1/2007 | Lapidus et al. | |
| 7,220,549 B2 | 5/2007 | Buzby | |
| 7,226,720 B2 | 6/2007 | Wisnudel et al. | |
| 7,279,563 B2 | 10/2007 | Kwiatkowski | |
| 7,282,337 B1 | 10/2007 | Harris | |
| 8,067,434 B2 | 11/2011 | Ibrahim et al. | |
| 10,683,531 B2 | 6/2020 | Stahl et al. | |
| 10,704,082 B2 | 7/2020 | Stahl et al. | |
| 2006/0252077 A1 | 11/2006 | Buzby | |
| 2007/0070349 A1 | 3/2007 | Harris et al. | |
| 2009/0093378 A1 | 4/2009 | Bignell et al. | |
| 2011/0201507 A1 | 8/2011 | Rava et al. | |
| 2011/0201598 A1 | 8/2011 | Gujral et al. | |
| 2012/0283145 A1 | 11/2012 | Wang | |
| 2013/0231253 A1 | 9/2013 | Amorese et al. | |
| 2013/0303461 A1 | 11/2013 | Iafrate et al. | |
| 2015/0211050 A1 | 7/2015 | Iafrate et al. | |
| 2015/0252361 A1 | 9/2015 | Hayden et al. | |
| 2017/0037459 A1* | 2/2017 | Godwin ............... C12Q 1/6853 |
| 2018/0127806 A1 | 5/2018 | Stahl et al. | |
| 2018/0127807 A1 | 5/2018 | Stahl et al. | |

FOREIGN PATENT DOCUMENTS

| | | |
|---|---|---|
| WO | WO 2001/083696 A2 | 11/2001 |
| WO | WO 2004/079326 A3 | 9/2004 |
| WO | WO 2006/034833 A1 | 4/2006 |
| WO | WO 2009/032167 A1 | 3/2009 |
| WO | WO 2011/014811 A1 | 2/2011 |
| WO | WO 2012/024658 A2 | 2/2012 |
| WO | WO 2014/008447 A1 | 1/2014 |
| WO | WO 2014/047678 A1 | 4/2014 |
| WO | WO 2014/144495 A1 | 9/2014 |
| WO | WO 2015/089496 A1 | 6/2015 |
| WO | WO 2015/112974 A1 | 7/2015 |
| WO | WO 2016/138500 A1 | 9/2016 |
| WO | WO 2017/177308 A1 | 10/2017 |
| WO | WO 2018/053362 A1 | 3/2018 |

OTHER PUBLICATIONS

Miyoshi D, Sugimoto N. Molecular crowding effects on structure and stability of DNA. Biochimie. Jul. 2008; 90(7):1040-51. Epub Feb. 21, 2008. (Year: 2008).*

Song Y, Liu KJ, Wang TH. Elimination of ligation dependent artifacts in T4 RNA ligase to achieve high efficiency and low bias microRNA capture. PLoS One. Apr. 10, 2014;9(4):e94619. pp. 1-9. (Year: 2014).*

Ruggiero et al. High-resolution analysis of the human T-cell receptor repertoire. Nat Commun. Sep. 1, 2015;6: 8081. pp. 1-7. (Year: 2015).*

Ruggiero et al. Supplemental Nat Commun. Sep. 1, 2015;6: 8081. pp. 1-45 (Year: 2015).*

Fadrosh DW, Ma B, Gajer P, Sengamalay N, Ott S, Brotman RM, Ravel J. An improved dual-indexing approach for multiplexed 16S rRNA gene sequencing on the Illumina MiSeq platform. Microbiome. Feb. 24, 2014; 2(1):6.pp. 1-7. (Year: 2014).*

(Continued)

*Primary Examiner* — Teresa E Strzelecka
*Assistant Examiner* — Olayinka A Oyeyemi
(74) *Attorney, Agent, or Firm* — Wolf, Greenfield & Sacks, P.C.

(57) ABSTRACT

Aspects of the technology disclosed herein relate to methods of preparing and analyzing nucleic acids, e.g., nucleic acids encoding immune receptors and immunoglobulins. In some embodiments, methods for preparing nucleic acids for sequence analysis (e.g., using next-generation sequencing) are provided herein.

24 Claims, 16 Drawing Sheets

Specification includes a Sequence Listing.

(56) References Cited

OTHER PUBLICATIONS

Boers SA, van der Reijden WA, Jansen R. High-throughput multilocus sequence typing: bringing molecular typing to the next level. PLoS One. 2012; 7(7):e39630 pp. 1-8. Epub Jul. 18, 2012. (Year: 2012).*
U.S. Appl. No. 16/919,238, filed Jul. 2, 2020, Stahl et al.
U.S. Appl. No. 16/804,695, filed Feb. 28, 2020, Stahl et al.
EP 17868046.8, Jun. 15, 2020, Extended European Search Report.
PCT/US2017/059804, Apr. 24, 2018, International Search Report and Written Opinion.
PCT/US2017/059804, May 16, 2019, International Preliminary Report on Patentability.
EP 17851671.2, Apr. 6, 2020, Extended European Search Report.
PCT/US2017/051924, Dec. 11, 2017, International Search Report and Written Opinion.
PCT/US2017/051924, Mar. 28, 2019, International Preliminary Report on Patentability.
EP 17851672.0, May 13, 2020, Extended European Search Report.
PCT/US2017/051927, Dec. 1, 2017, International Search Report and Written Opinion.
PCT/US2017/051927, Mar. 28, 2019, International Preliminary Report on Patentability.
Extended European Search Report for Application No. EP 17868046.8, dated Jun. 15, 2020.
International Search Report and Written Opinion for Application No. PCT/US2017/059804, dated Apr. 24, 2018.
International Preliminary Report on Patentability for Application No. PCT/US2017/059804, dated May 16, 2019.
Extended European Search Report for Application No. 17851671.2, dated Apr. 6, 2020.
International Preliminary Report on Patentability for Application No. PCT/US2017/051924, dated Mar. 28, 2019.
International Search Report and Written Opinion for Application No. PCT/US2017/051924, dated Dec. 11, 2017.
Extended European Search Report for Application No. 17851672.0, dated May 13, 2020.
International Preliminary Report on Patentability for Application No. PCT/US2017/051927, dated Mar. 28, 2019.
International Search Report and Written Opinion for Application No. PCT/US2017/051927, dated Dec. 1, 2017.
Akeno-Stuart et al., The RET kinase inhibitor NVP-AST487 blocks growth and calcitonin gene expression through distinct mechanisms in medullary thyroid cancer cells. Cancer Res. Jul. 15, 2007;67(14):6956-64.
Bentley, Whole-genome re-sequencing. Curr Opin Genet Dev. Dec. 2006;16(6):545-52. Epub Oct. 18, 2006.
Bowman et al., Multiplexed Illumina sequencing libraries from picogram quantities of DNA. BMC Genomics. Jul. 9, 2013;14:466. doi: 10.1186/1471-2164-14-466.
Carlomagno et al., BAY 43-9006 inhibition of oncogenic RET mutants. J Natl Cancer Inst. Mar. 1, 2006;98(5):326-34.
Cuccuru et al., Cellular effects and antitumor activity of RET inhibitor RPI-1 on MEN2A-associated medullary thyroid carcinoma. J Natl Cancer Inst. Jul. 7, 2004;96(13):1006-14.
Das et al., Full-length cDNAs: more than just reaching the ends. Physiol Genomics. Jul. 17, 2001;6(2):57-80.
Freier et al., Improved free-energy parameters for predictions of RNA duplex stability. Proc Natl Acad Sci U S A. Dec. 1986; 83(24): 9373-9377. doi: 10.1073/pnas.83.24.9373.
Galkin et al., Identification of NVP-TAE684, a potent, selective, and efficacious inhibitor of NPM-ALK. Proc Natl Acad Sci U S A. Jan. 2, 2007;104(1):270-5. Epub Dec. 21, 2006. Erratum in: Proc Natl Acad Sci U S A. Feb. 6, 2007;104(6):2025.
Gazzola et al., The evolution of clonality testing in the diagnosis and monitoring of hematological malignancies [published correction appears in Ther Adv Hematol. Oct. 2014;5(5):181]. Ther Adv Hematol. 2014;5(2):35-47. doi:10.1177/2040620713519729.
Grazma et al., Activity of novel RET inhibitors against RET genotypes associated with medullary thyroid cancer. J Clin Oncol. 2010;28:15s:5559. Epub Sep. 22, 2016. doi: 10/1200/jco.1010.28.15_suppl.5559.
Hallberg et al., ALK and NSCLC: Targeted therapy with ALK Inhibitors. F1000 Med Reports 2011;3:21. Epub Nov. 1, 2011. doi: 10.3410/M3-21. 9 pages.
Kohno et al., KIF5B-RET fusions in lung adenocarcinoma. Nat Med. Feb. 12, 2012;18(3):3757. doi: 10.1038/nm.2644.
Mardis, The impact of next-generation sequencing technology on genetics. Trends Genet. Mar. 2008;24(3):133-41. doi: 10.1016/j.tig.2007.12.007. Epub Feb. 11, 2008.
Mologni et al., Inhibition of RET tyrosine kinase by SU5416. J Mol Endocrinol. Oct. 2006;37(2):199-212.
Mologni, Development of RET kinase inhibitors for targeted cancer therapy. Curr Med Chem. 2011;18(2):162-75.
Mussolin et al., Plasma Cell-Free DNA in Paediatric Lymphomas. J Cancer. 2013; 4(4): 323-329. EPub Apr. 16, 2013. doi: 10.7150/jca.6226.
Nyrén et al., Solid phase DNA minisequencing by an enzymatic luminometric inorganic pyrophosphate detection assay. Anal Biochem. Jan. 1993;208(1):171-5.
Rikova et al., Global survey of phosphotyrosine signaling identifies oncogenic kinases in lung cancer. Cell. Dec. 14, 2007;131(6):1190-203.
Ruggiero et al., High-resolution analysis of the human T-cell receptor repertoire. Nat Commun. Sep. 1, 2015;6:8081. doi: 10.1038/ncomms9081.
Rumsby, An introduction to PCR techniques. Methods Mol Biol. 2006;324:75-89.
Sakamoto et al., CH5424802, a selective ALK inhibitor capable of blocking the resistant gatekeeper mutant. Cancer Cell. May 17, 2011;19(5):679-90. doi: 10.1016/j.ccr.2011.04.004.
Samadi et al., A novel RET inhibitor with potent efficacy against medullary thyroid cancer in vivo. Surgery. Dec. 2010;148(6):1228-36; discussion 1236. doi: 10.1016/j.surg.2010.09.026.
Shendure et al., Next-generation DNA sequencing. Nat Biotechnol. Oct. 2008;26(10):1135-45. doi: 10.1038/nbt1486.
Soda et al., Identification of the transforming EML4-ALK fusion gene in non-small-cell lung cancer. Nature. Aug. 2, 2007;448(7153):561-6. Epub Jul. 11, 2007.
Strausberg et al., Emerging DNA sequencing technologies for human genomic medicine. Drug Discov Today. Jul. 2008;13(13-14):569-77. doi: 10.1016/j.drudis.2008.03.025. Epub May 22, 2008.
Su et al., Next-generation sequencing and its applications in molecular diagnostics. Expert Rev Mol Diagn. Apr. 2011;11(3):333-43. doi: 10.1586/erm.11.3.
Xiao et al., Systematic Comparative Evaluation of Methods for Investigating the TCRβ Repertoire. PLoS One. 2016; 11(3): e0152464. EPub Mar. 28, 2016. doi: 10.1371/journal.pone.0152464. 18 pages.
Ying, Complementary DNA libraries: an overview. Mol Biotechnol. Jul. 2004;27(3):245-52.
Zhang et al., The impact of next-generation sequencing on genomics. J Genet Genomics. Mar. 20, 2011;38(3):95-109. doi: 10.1016/j.jgg.2011.02.003. Epub Mar. 15, 2011. Author Manuscript.
Zou et al., An orally available small-molecule inhibitor of c-Met, PF-2341066, exhibits cytoreductive antitumor efficacy through antiproliferative and antiangiogenic mechanisms. Cancer Res. May 1, 2007;67(9):4408-17.

* cited by examiner

METHODS OF NUCLEIC ACID SAMPLE PREPARATION FOR IMMUNE REPERTOIRE SEQUENCING

RELATED APPLICATIONS

This application claims priority under 35 U.S.C. § 119(e) to U.S. Provisional Patent Application No. 62/416,677, filed Nov. 2, 2016, which is hereby incorporated by reference in its entirety.

TECHNICAL FIELD

The technology described herein relates to methods and compositions useful in the preparation of nucleic acid molecules for analysis.

BACKGROUND

The adaptive immune system is composed of highly specialized, systemic cells and processes aimed at eliminating or preventing pathogen growth. T cells and B cells may be thought of as the principal cellular components of the adaptive immune system driving the adaptive immune response by generating a wide diversity of antigen-binding molecules through genetic recombination and somatic mutation of their antigen receptor loci. Immature T and B-cells undergo selective processes to yield populations largely devoid of auto-reactivity. Armed with this initial repertoire of antigen binding molecules (e.g., T cell receptors and immunoglobulins), naïve T and B cells circulate throughout the body where they can come in contact with antigen.

Upon exposure to cognate antigen, and in conjunction with sufficient co-stimulatory signals, antigen-specific T or B cells are activated and proliferate, and in the case of B cells, may undergo further sequence editing of their immune receptor loci (e.g., through somatic hypermutation and/or additional recombination).

As a result of these selective processes, the repertoire of binding specificities in an individual sample can provide a history of past antigenic exposures, as well as being informative of inherent repertoire capabilities and limitations.

SUMMARY

Aspects of the technology disclosed herein relate to methods of preparing and analyzing nucleic acids. Methods provided herein are useful, in some embodiments, for detecting ultra-low frequency nucleic acid variants (e.g., splice variants, fusions, single nucleotide variants, insertions and deletions, copy number variants, mRNAs from somatically recombined immune receptor loci, and expression level variants) in nucleic acid preparations, including sequences representative of an immune repertoire comprising a diverse landscape of nucleic acid sequences encoding immune receptors and immunoglobulins. Methods provided herein, in some embodiments, involve ligation-based capture that enriches for nucleic acid molecules having nucleotide sequences corresponding to transcribed nucleic acids that reflect previously occurring recombination and/or splicing events. In some embodiments, unique molecule capture is vastly improved over conventional methods for nucleic acids extracted from individuals, e.g., tumor bearing individuals or immune-compromised individuals. In some embodiments, capture efficiency is at least doubled compared with conventional methods for nucleic acids extracted from individuals, e.g., tumor bearing individuals or immune-compromised individuals. In some embodiments, improved depth is accomplished as a result of improved front-end capture chemistry.

In some embodiments, methods provided herein are useful for evaluating RNA immune repertoires via sequencing. In some embodiments, methods and compositions useful in the preparation of nucleic acid samples for sequence analysis (e.g., using next-generating sequencing) are provided herein. In some embodiments, techniques described herein are related to methods of determining a nucleic acid sequence. In some embodiments, methods and compositions described herein relate to the enrichment of nucleic acids comprising one or more target nucleotide sequences prior to sequencing. In some aspects, the disclosure provides methods of preparing nucleic acids (e.g., for use in a sequencing analysis) that involve the use of a capture moiety modified primer to synthesize a first nucleic acid strand or that involve adding one or more capture moiety modified nucleotides to a nucleic acid.

In some embodiments, the methods further involve ligating an adapter nucleic acid to the nucleic acid to which the capture moiety modified primer has been used in synthesizing a first strand of the nucleic acid to produce a ligation product. In some embodiments, the methods further involve ligating an adapter nucleic acid to the nucleic acid to which the capture moiety modified nucleotide has been added to produce a ligation product. In some embodiments, the methods further involve capturing the ligation product by contacting the ligation product with a binding partner of a capture moiety of the capture moiety modified primer or a binding partner of a capture moiety of the capture moiety modified nucleotide.

In some aspects, the disclosure provides methods of preparing nucleic acids for analysis, in which the methods involve: (a) contacting a nucleic acid molecule comprising a target nucleotide sequence with a capture moiety modified primer that specifically anneals to the target nucleotide sequence under hybridization conditions; (b) conducting a first strand synthesis reaction that is primed by a hybridized capture moiety modified primer and that uses the nucleic acid molecule as a template; (c) conducting a second strand synthesis reaction that uses a product of the first strand synthesis reaction as a template to generate a double-stranded nucleic acid comprising a capture moiety; (d) ligating an adapter nucleic acid to the double-stranded nucleic acid to produce a ligation product comprising the capture moiety; (e) capturing the ligation product by contacting the ligation product with a binding partner of the capture moiety; and (f) amplifying the captured ligation product by polymerase chain reaction using a target-specific primer that comprises a 3' portion that specifically anneals to the target nucleotide sequence and a first adapter primer that specifically anneals to a complementary sequence of the adapter nucleic acid, wherein the target-specific primer comprises a 5' tail portion that does not specifically anneal to the target nucleotide sequence.

In some embodiments, methods provided herein further comprise (g) amplifying an amplification product of step (f) by polymerase chain reaction using a tail primer that comprises a 3' portion that specifically anneals to a complementary sequence of the 5' tail portion of the target-specific primer and a second adapter primer that specifically anneals to a complementary sequence of the adapter nucleic acid, wherein the tail primer comprises a 5' portion that does not specifically anneal to a complementary sequence of the target-specific primer. In some embodiments, the 5' portion of the tail primer comprises at least one of a sample index region, a PCR primer binding region, a molecular barcode region, and a sequencing primer site region. In some embodiments, the first adapter primer and the second adapter primer are the same. For example, in some embodiments, the first and second adapter primers consist of the same nucleotide sequence. In some embodiments, the first adapter primer and the second adapter primer are different (e.g., consist of different nucleotide sequences and/or comprise one or more different moieties). In some embodiments, the second adapter primer is nested relative to the first adapter primer. In some embodiments, the second adapter primer is not nested relative to the first adapter primer.

In some embodiments, step (d) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid comprises a duplex portion and an overhang sequence, wherein the overhang sequence comprises a nucleotide sequence that is complementary to an overhang sequence at the 3' end of the double stranded nucleic acid. In some embodiments, the adapter nucleic acid comprises at least one of a sample index region, a PCR primer binding region, a molecular barcode region (e.g., a region that uniquely identifies input molecules), and a sequencing primer site region.

In some embodiments, step (d) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

In some embodiments, the capture moiety modified primer comprises at least one capture moiety modified nucleotide. In some embodiments, the capture moiety modified primer comprises a first chemical coupling group configured to bind a second chemical coupling group attached to a capture moiety. In some embodiments, the capture moiety is a biotin moiety. In some embodiments, the biotin moiety comprises biotin-triethylene glycol, bis-biotin, photocleavable biotin, desthiobiotin, desthiobiotin-triethylene glycol, or biotin azide. In some embodiments, the binding partner of the capture moiety is streptavidin. In some embodiments, the streptavidin is attached to a substrate. In some embodiments, the substrate comprises a solid surface. In some embodiments, the solid surface comprises a paramagnetic bead.

In some embodiments, methods described herein further comprise a step of releasing the captured ligation product from the binding partner of the capture moiety. In some embodiments, the captured ligation product is released from the binding partner of the capture moiety by contacting with a chemical reagent and/or applying heat. In some embodiments, the chemical reagent is a base or basic solution. In some embodiments, the chemical reagent comprises sodium hydroxide (NaOH). It should be appreciated that, in some embodiments, contacting can involve mixing two solutions (e.g., a solution comprising a base and a solution comprising a washed immobilized nucleic acid), adding a solid to a solution, or adding a solution to a solid. In some embodiments, the captured ligation product is released from the binding partner of the capture moiety by contacting with NaOH and heating (e.g., heating to above room temperature, such as a temperature in a range of 25 to 90° C., 25 to 70° C., 25 to 50° C., 35 to 65° C., 35 to 45° C., 30 to 40° C., 40 to 50° C.). In some embodiments, the captured ligation product remains bound to the binding partner of the capture moiety, e.g., for further preparation for analysis. In some embodiments, the captured ligation product is released from the binding partner of the capture moiety prior to further preparation for analysis.

In some embodiments, methods provided herein further comprise a washing step after step (d) and prior to step (e).

In some embodiments, methods provided herein further comprise, after step (e) and prior to step (f): i) immobilizing the double-stranded nucleic acid, which comprises the capture moiety, on a paramagnetic substrate; and ii) washing the immobilized double-stranded nucleic acid. In some embodiments, methods provided herein further comprise, after step ii): iii) releasing the washed immobilized double-stranded nucleic acid from the paramagnetic substrate.

In some embodiments, methods provided herein further comprise, after step (c) and prior to step (d), 5' phosphorylating the double-stranded nucleic acid. In some embodiments, 5' phosphorylating comprises generating a phosphate group at a 5' end of a strand of the double-stranded nucleic acid. For example, in some embodiments, a phosphate group can be added to a hydroxyl group at the 5' end of the strand (e.g., via the action of a polynucleotide kinase).

In some embodiments, methods provided herein further comprise, after step (c) and prior to step (d), end repairing the double-stranded nucleic acid to produce a blunt-ended, double-stranded nucleic acid. In some embodiments, end repair comprises blunt-ending. In some embodiments, blunt-ending is achieved by removing terminal unpaired nucleotides (e.g., an overhang sequence) from a strand of the double-stranded nucleic acid. For example, in some embodiments, terminal unpaired nucleotides may be removed from a strand of a double-stranded nucleic acid by using an enzyme (e.g., Klenow fragment) with exonuclease activity (e.g., to hydrolyze a terminal phosphodiester bond, thereby removing the overhang one base at a time). In some embodiments, blunt-ending is achieved by filling in a recessed terminus with a polymerizing enzyme (e.g., a DNA polymerase) in the presence of nucleotide triphosphates.

In some embodiments, methods provided herein further comprise adding (e.g., ligating, tailing) one or more nucleotides to a 3' end of the blunt-ended, double-stranded nucleic acid. In some embodiments, the one or more nucleotides comprise deoxyadenosine nucleotides. For example, in some embodiments, the methods further comprise dA-tailing a 3' end of the double-stranded nucleic acid (e.g., using Klenow fragment). In some embodiments, the adapter nucleic acid comprises a nucleotide sequence at a 3' end comprising one or more nucleotides complementary to the one or more nucleotides added to the 3' end of the blunt-ended, double-stranded nucleic acid. In some embodiments, the nucleotide sequence at the 3' end of the adapter nucleic acid comprises one or more deoxythymidine nucleotides. In some embodiments, the adapter nucleic acid further comprises a blocking strand annealed to an amplification strand that comprises the nucleotide sequence at the 3' end, and wherein the nucleotide sequence at the 3' end is unpaired such that it forms an overhang sequence.

In some embodiments, the methods further comprise, after end repair: i) immobilizing the double-stranded nucleic acid, which comprises the capture moiety, on a paramagnetic substrate; ii) washing the immobilized double-stranded nucleic acid; and iii) releasing the washed immobilized double-stranded nucleic acid from the paramagnetic substrate.

In some embodiments, the methods further comprise, after end repair: i) immobilizing the double-stranded nucleic acid, which comprises the capture moiety, on a paramagnetic substrate; and ii) washing the immobilized double-stranded nucleic acid. In some embodiments, the methods further comprise a washing step after end repair and prior to step i).

In some embodiments, methods provided herein further comprise: (h) immobilizing an amplification product of step (g) on a paramagnetic substrate; (i) washing the immobilized amplification product; and (j) releasing the washed immobilized amplification product from the paramagnetic substrate. In some embodiments, the method further comprises a washing step after step (g) and prior to step (h).

In some embodiments, in step (d), the double-stranded nucleic acid is ligated to the adapter nucleic acid in the presence of a crowding agent. In some embodiments, the crowding agent is polyethylene glycol in an amount representing 5% to 50% of a ligation mixture.

In some embodiments, methods provided herein further comprise, after step (b) and prior to step (c), contacting the nucleic acid molecule with a ribonuclease enzyme. In some embodiments, the ribonuclease enzyme degrades portions of the nucleic acid molecule such that fragments remain annealed to the product of the first strand synthesis reaction. In some embodiments, the second strand synthesis reaction is primed by a fragment of the nucleic acid molecule hybridized to the product of the first strand synthesis reaction.

In some embodiments, the second strand synthesis is randomly primed using a plurality of random primers. In some embodiments, the plurality of random primers are between 6 bases in length and 15 bases in length.

In some embodiments, the nucleic acid molecule comprises mRNA. In some embodiments, the nucleic acid molecule is obtained from a sample comprising a T cell, a B cell, or a mixture thereof. In some embodiments, the sample comprises one or more T cells, one or more B cells, or a mixture thereof. In some embodiments, the sample comprises a mixture of T cells and B cells. In some embodiments, the mixture of T cells and B cells further comprises one or more non-blood cell types. In some embodiments, the mixture of T cells and B cells further comprises one or more types of leukocytes (e.g., neutrophils, eosinophils, basophils, natural killer (NK) cells, monocytes, histiocytes, dendritic cells, mast cells, microglia, etc.).

In some embodiments, the sample is obtained from a subject having, or suspected of having, a T cell malignancy or a B cell malignancy. In some embodiments, the sample is obtained from a subject having, or suspected of having, lymphoma or leukemia (e.g., multiple myeloma, acute lymphoblastic leukemia, or chronic lymphocytic leukemia). In some embodiments, the sample is obtained from a subject having, or suspected of having, a solid tumor (e.g., sarcoma, carcinoma, lymphoma, or any tumor of non-lymphoid origin that may or may not contain non-malignant immune cells). In some embodiments, the sample is obtained from a subject that has undergone or will undergo transplantation. In some embodiments, the sample is obtained from a subject whose immune response to a treatment is being evaluated. In some embodiments, the sample is obtained from a subject having, or suspected of having, a white blood cell malignancy. In some embodiments, the sample is obtained from a subject having, or suspected of having, an autoimmune condition. For example, in some embodiments, the immune condition is any condition driven by autoreactive T cells, autoreactive B cells, or a combination thereof. In some embodiments, the sample is obtained from a subject having, or suspected of having, a T cell malignancy and/or a B cell malignancy (e.g., lymphoma and subtypes thereof, multiple myeloma, etc.) In some embodiments, the sample is obtained from a subject having a solid tumor. In some embodiments, the subject is a human. In some embodiments, the subject is a chordate. In some embodiments, the nucleic acid molecule is obtained from a sample comprising a leukocyte. In some embodiments, the target nucleotide sequence comprises a nucleotide sequence corresponding to a portion of a T cell receptor (TCR) gene or a B cell receptor (BCR) gene.

In some embodiments, the capture moiety modified primer comprises a nucleotide sequence that is complementary to an immune receptor gene or an immunoglobulin gene. In some embodiments, the capture moiety modified primer specifically anneals to a constant region that is downstream of a complementarity determining region 3 (CDR3). In some embodiments, the target-specific primer specifically anneals to a constant region or a J-segment that is downstream of a CDR3. In some embodiments, the target-specific primer specifically anneals to an exon-exon junction formed between a constant region and a J-segment, and wherein the exon-exon junction is downstream of a CDR3.

In some aspects, the disclosure provides methods of preparing nucleic acids for analysis, in which the methods involve: (a) contacting a nucleic acid molecule comprising a known target nucleotide sequence and an unknown target nucleotide sequence with a capture moiety modified primer that specifically anneals to the known target nucleotide sequence under hybridization conditions; (b) conducting a first strand synthesis reaction that is primed by a hybridized capture moiety modified primer and that uses the nucleic acid molecule as a template; (c) conducting a second strand synthesis reaction that is primed by a fragment of the nucleic acid molecule and that uses a product of the first strand synthesis reaction as a template to generate a double-stranded nucleic acid comprising a capture moiety; (d) end repairing the double-stranded nucleic acid to produce a blunt-ended, double-stranded nucleic acid comprising the capture moiety; (e) ligating an adapter nucleic acid to the blunt-ended, double-stranded nucleic acid to produce a ligation product, wherein the ligation product comprises the unknown target nucleotide sequence flanked by the adapter nucleic acid and the capture moiety; (f) capturing the ligation product by contacting the ligation product with an immobilized binding partner of the capture moiety; (g) amplifying the ligation product by polymerase chain reaction using a target-specific primer that comprises a 3' portion that specifically anneals to the known target nucleotide sequence and a first adapter primer that specifically anneals to a complementary sequence of the adapter nucleic acid, wherein the target-specific primer comprises a 5' tail portion that does not specifically anneal to the known target nucleotide sequence; and (h) amplifying an amplification product of step (g) by polymerase chain reaction using a tail primer that specifically anneals to a complementary sequence of the 5' tail portion of the target-specific primer and a second adapter primer that specifically anneals to a complementary sequence of the adapter nucleic acid. In some embodiments, methods described herein further comprise, after step (e) and prior to step (f), washing the ligation product. In some embodiments, methods described herein further comprise, after step (f) and prior to step (g), washing a captured ligation product. In some embodiments, methods described herein further comprise (i) washing an amplification product of step (h). In some embodiments, the second strand synthesis reaction of step (c) may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture.

In some aspects, the disclosure provides methods of preparing nucleic acids for analysis, in which the methods involve: (a) contacting a nucleic acid molecule comprising a target nucleotide sequence with a first target-specific primer that specifically anneals to the target nucleotide sequence under hybridization conditions; (b) conducting a first strand synthesis reaction that is primed by a hybridized first target-specific primer and that uses the nucleic acid molecule as a template; (c) conducting a second strand synthesis reaction that is primed by a hybridized fragment (e.g., a hybridized part or hybridized portion) of the nucleic acid molecule and that uses a product of the first strand synthesis reaction as a template to generate a double-stranded nucleic acid; (d) ligating an adapter nucleic acid to the double-stranded nucleic acid to produce a ligation product; (e) amplifying the ligation product by polymerase chain reaction using a second target-specific primer that comprises a 3' portion that specifically anneals to the target nucleotide sequence and a first adapter primer that specifically anneals to a complementary sequence of the adapter nucleic acid, wherein the second target-specific primer comprises a 5' tail portion that does not specifically anneal to the target nucleotide sequence; and (f) amplifying an amplification product of step (e) by polymerase chain reaction using a tail primer that comprises a 3' portion that specifically anneals to a complementary sequence of the 5' tail portion of the second target-specific primer and a second adapter primer that specifically anneals to a complementary sequence of the adapter nucleic acid, wherein the tail primer comprises a 5' portion that does not specifically anneal to a complementary sequence of the second target-specific primer. In some embodiments, the second strand synthesis reaction of step (c) may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture.

In some embodiments, the first target-specific primer comprises a capture moiety. In some embodiments, methods provided herein further comprise, after step (d) and prior to step (e), capturing the ligation product by contacting the ligation product with a binding partner of the capture moiety.

In some embodiments, the first strand synthesis reaction is conducted using at least one type of capture moiety modified nucleotide, and wherein the product of the first strand synthesis reaction comprises at least one capture moiety. In some embodiments, methods provided herein further comprise, after step (d) and prior to step (e), capturing the ligation product by contacting the ligation product with an immobilized binding partner of the at least one capture moiety.

In some embodiments, methods provided herein further comprise, after step (c) and prior to step (d), capturing the double-stranded nucleic acid by contacting the double-stranded nucleic acid with an immobilized binding partner of the at least one capture moiety.

In some aspects, the disclosure provides methods of determining an immune repertoire in a sample, in which the methods involve: (a) obtaining a sample comprising a nucleic acid molecule encoding at least one of an immune receptor and an immunoglobulin; (b) contacting the nucleic acid molecule from the sample with a first target-specific primer that specifically anneals to a target nucleotide sequence of the nucleic acid molecule under hybridization conditions; (c) conducting a first strand synthesis reaction that is primed by a hybridized first target-specific primer and that uses the nucleic acid molecule as a template; (d) conducting a second strand synthesis reaction that uses a product of the first strand synthesis reaction as a template to generate a double-stranded nucleic acid; (e) ligating an adapter nucleic acid to the double-stranded nucleic acid to produce a ligation product; and (f) amplifying the ligation product by polymerase chain reaction using a second target-specific primer that comprises a 3' portion that specifically anneals to the target nucleotide sequence and a first adapter primer that specifically anneals to a complementary sequence of the adapter nucleic acid, wherein the second target-specific primer comprises a 5' tail portion that does not specifically anneal to the target nucleotide sequence; (g) amplifying an amplification product of step (f) by polymerase chain reaction using a tail primer that comprises a 3' portion that specifically anneals to a complementary sequence of the 5' tail portion of the second target-specific primer and a second adapter primer that specifically anneals to a complementary sequence of the adapter nucleic acid, wherein the tail primer comprises a 5' portion that does not specifically anneal to a complementary sequence of the second target-specific primer; and (h) sequencing an amplification product of step (g) using a first and second sequencing primer.

In some embodiments, the immune receptor comprises a TCR. In some embodiments, the immunoglobulin comprises a BCR. In some embodiments, the target nucleotide sequence corresponds to a genetically recombined sequence. In some embodiments, the target nucleotide sequence corresponds to at least one of a TCR locus (e.g., TCRA, TCRB, TCRG, or TCRD). In some embodiments, the target nucleotide sequence corresponds to at least one of a BCR locus (e.g., IGH, IGK, or IGL). In some embodiments, the sample comprises a T cell, a B cell, or a mixture thereof. In some embodiments, the sample is obtained from a subject. In some embodiments, the subject is a human. In some embodiments, the subject is a rodent. For example, in some embodiments, the subject is a mouse, a rat, a gerbil, a hamster, a guinea pig, a chinchilla, a squirrel, or a humanized form of any such rodent (e.g., a rodent expressing human TCRs and/or human BCRs).

In some aspects, the disclosure provides methods of preparing nucleic acids for analysis, in which the methods involve: (a) contacting a nucleic acid molecule comprising a target nucleotide sequence with a first target-specific primer that specifically anneals to the target nucleotide sequence under conditions to generate a primer-hybridized nucleic acid molecule; (b) contacting the primer-hybridized nucleic acid molecule with a plurality of types of nucleotides for incorporation into a first strand that is complementary to the nucleic acid molecule, wherein at least one of the plurality of types of nucleotides comprises a capture moiety; (c) conducting a first strand synthesis reaction that is primed by the first target-specific primer of the primer-hybridized nucleic acid molecule and that uses the nucleic acid molecule of the primer-hybridized nucleic acid molecule as a template, wherein a product of the first strand synthesis reaction comprises at least one capture moiety; (d) conducting a second strand synthesis reaction that is primed by a fragment of the nucleic acid molecule and that uses the product of the first strand synthesis reaction as a template to generate a double-stranded nucleic acid comprising the at least one capture moiety; (e) ligating an adapter nucleic acid to the double-stranded nucleic acid to produce a ligation product comprising the at least one capture moiety; and (f)

amplifying the ligation product by polymerase chain reaction using a second target-specific primer that comprises a 3' portion that specifically anneals to the target nucleotide sequence and a first adapter primer that specifically anneals to a complementary sequence of the adapter nucleic acid, wherein the second target-specific primer comprises a 5' tail portion that does not specifically anneal to the target nucleotide sequence. In some embodiments, the second strand synthesis reaction of step (d) may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture.

In some embodiments, methods provided herein further comprise, after step (e) and prior to step (f), capturing the ligation product by contacting the ligation product with an immobilized binding partner of the capture moiety.

In some embodiments, methods provided herein further comprise, after step (d) and prior to step (e), capturing the double-stranded nucleic acid by contacting the double-stranded nucleic acid with an immobilized binding partner of the capture moiety.

In some aspects, the disclosure provides methods of preparing nucleic acids for analysis, in which the methods involve: (a) contacting a nucleic acid molecule comprising a target nucleotide sequence with a capture moiety modified primer that comprises a 3' portion that specifically anneals to the target nucleotide sequence under hybridization conditions and a 5' tail portion that does not specifically anneal to the target nucleotide sequence; (b) conducting a first strand synthesis reaction that is primed by a hybridized capture moiety modified primer and that uses the nucleic acid molecule as a template; (c) contacting a product of the first strand synthesis reaction with a plurality of random primers under hybridization conditions, wherein each of the plurality of random primers comprises a non-random 5' tail portion comprising a common sequence; (d) conducting a second strand synthesis reaction that is primed by at least one of the plurality of random primers and that uses a product of the first strand synthesis reaction as a template to generate a double-stranded nucleic acid comprising the capture moiety; (e) capturing the double-stranded nucleic acid comprising the capture moiety by contacting the double-stranded nucleic acid with a binding partner of the capture moiety; (f) amplifying the double-stranded nucleic acid by polymerase chain reaction using a first tail primer and a first target-specific primer that specifically anneals to the target nucleotide sequence, wherein the first tail primer comprises a 3' portion that specifically anneals to a complement of the common sequence and a 5' tail portion that does not specifically anneal to a complement of the common sequence; and (g) amplifying an amplification product of step (f) by polymerase chain reaction using a second target-specific primer a second tail primer that specifically anneals to a complement of the 5' tail portion of the first tail primer, wherein the second target-specific primer comprises a 3' portion that specifically anneals to the target nucleotide sequence and a 5' tail portion that does not specifically anneal to the target nucleotide sequence.

Other advantages and novel features of the present disclosure will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Among other aspects, the present disclosure provides improved techniques related to the preparation of nucleic acid libraries for immune repertoire analysis. As described herein, a target nucleic acid molecule (e.g., mRNA) comprising a known target nucleotide sequence is contacted with a target-specific primer and extended in a first strand synthesis reaction using the nucleic acid molecule as a template. In some embodiments, the first strand synthesis reaction may be conducted such that a product of the first strand synthesis reaction comprises a capture moiety, and a binding partner of the capture moiety can be used to capture (e.g., isolate) the product. Accordingly, aspects of the disclosure provide techniques useful for enriching for the product of the first strand synthesis that is complementary to the initial input comprising the target nucleic acid molecule (e.g., mRNA).

In some aspects, the disclosure relates to the recognition that incorporation of a capture moiety into a first strand synthesized from a target nucleic acid molecule (e.g., RNA) during library preparation minimizes the presence of non-target nucleic acids during enrichment for nucleic acids comprising a target nucleotide sequence. This may be particularly advantageous when preparing nucleic acid libraries for immune repertoire sequencing. For example, although TCR and BCR genomic sequences will be present in all cells, the TCR and BCR mRNA will only be expressed in T cells and B cells, respectively. Evaluation of the immune repertoire relies on analyzing these genes after processing (e.g., recombination, splicing, etc.) to evaluate the sequence landscape present in a system. Accordingly, in some embodiments, techniques provided herein permit selective capture of mRNAs expressed from recombined immune loci. For example, as described herein, when a first strand is synthesized directly from a target nucleic acid, the capture moiety allows for enrichment of the desired product while minimizing non-target nucleic acid carryover.

In some aspects, the disclosure provides a method of preparing nucleic acids for analysis, comprising synthesizing a first nucleic acid strand using a capture moiety modified primer and a nucleic acid molecule comprising a target nucleotide sequence as a template, ligating an adapter nucleic acid to the first nucleic acid strand, and capturing the adapter-ligated first nucleic acid strand with a binding partner of the capture moiety.

Figure 1:
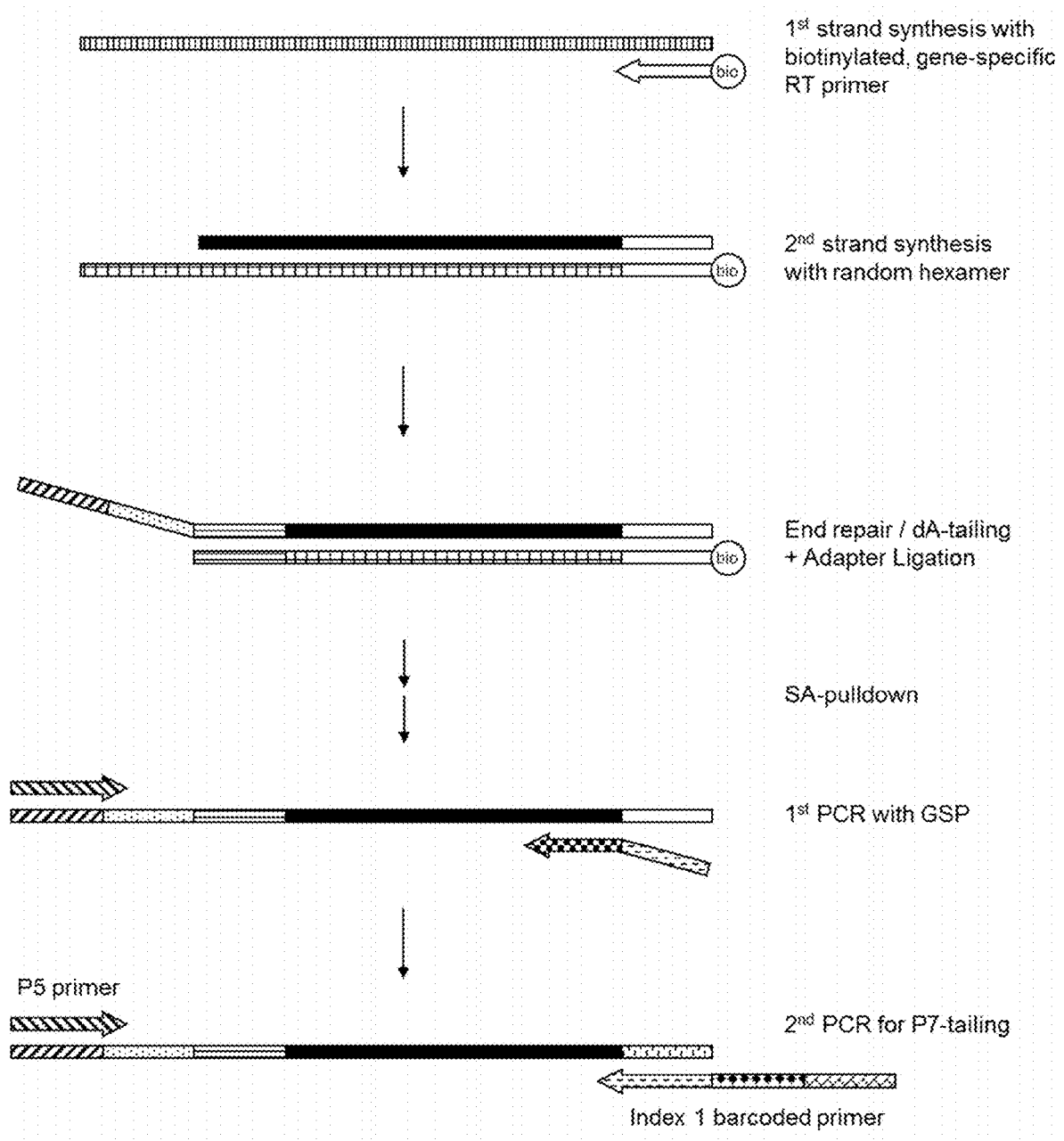
FIG. 1 is an illustration of a strategy for preparing a nucleic acid molecule for analysis using a capture moiety modified primer.

In some embodiments, the capture moiety modified primer is a biotin moiety modified primer. A depiction of this method is shown in FIG. 1, which provides a non-limiting example of a method involving a biotin moiety modified primer. In this embodiment, an RNA molecule (e.g., mRNA) is annealed with a DNA primer that is modified to comprise a biotin moiety. The biotin moiety modified primer is extended in a first strand synthesis reaction to generate a DNA/RNA hybrid. The RNA of the DNA/RNA hybrid is subjected to degradation via the action of a ribonuclease, and the RNA fragments that remain annealed to the DNA serve as primers in a second strand synthesis reaction to generate a double-stranded cDNA. In some embodiments, the second strand synthesis reaction of may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture. The double-stranded cDNA is subjected to end repair and dA-tailing to generate 3' overhangs suitable for a ligation reaction. Following ligation of an adapter nucleic acid to the double-stranded cDNA, these library molecules are captured, or isolated, from unligated adapter using a streptavidin-coated substrate (e.g., a paramagnetic substrate).

In some embodiments, following the capture, a first round of PCR amplification of the substrate-immobilized, captured adapter-ligated double-stranded cDNA is conducted. In yet other embodiments, the captured adapter-ligated double-stranded cDNA is eluted from the paramagnetic substrate prior to first round PCR. Elution of captured adapter-ligated nucleic acids from paramagnetic substrates can be performed, by way of example and not limitation, using a chemical reagent and/or heat. In some embodiments, the chemical reagent is a base (e.g., NaOH). In some embodiments, captured adapter-ligated double-stranded cDNA is eluted with a low concentration (e.g., less than 1 M, less than 0.5 M, less than 0.1 M, less than 0.05 M, less than 0.01 M, less than 0.001 M, less than 0.0001 M) of NaOH. In some embodiments, captured adapter-ligated double-stranded cDNA is eluted with a low concentration of NaOH and heat.

The immobilized or eluted adapter-ligated double-stranded cDNA is subjected to a first round of PCR amplification using a first adapter primer that anneals to a complement of the adapter and a target specific primer that hybridizes to a target nucleotide sequence and has a non-hybridized tail region comprising a common sequence. In this way, the first adapter primer primes off of the strand generated by the target specific primer. A second round of PCR amplification is conducted using a tail primer that anneals to a complement of the common sequence and a second adapter primer that anneals to a complement of the adapter. As shown, the tail primer includes an index 1 barcoded primer. In some embodiments, the tail primer includes an index 2 barcoded primer. In some embodiments, the adapter nucleic acid includes an index 1 primer and the tail primer includes an index 2 primer.

In some aspects, the disclosure provides a method of preparing nucleic acids for analysis, comprising contacting a primer-hybridized nucleic acid molecule comprising a target nucleotide sequence with a capture moiety modified nucleotide for incorporation into a newly synthesized strand, subjecting the mixture to extension conditions to synthesize a first nucleic acid strand comprising at least one capture moiety modified nucleotide, ligating an adapter nucleic acid to the first nucleic acid strand, and capturing the adapter-ligated first nucleic acid strand with a binding partner of the capture moiety.

Figure 2:
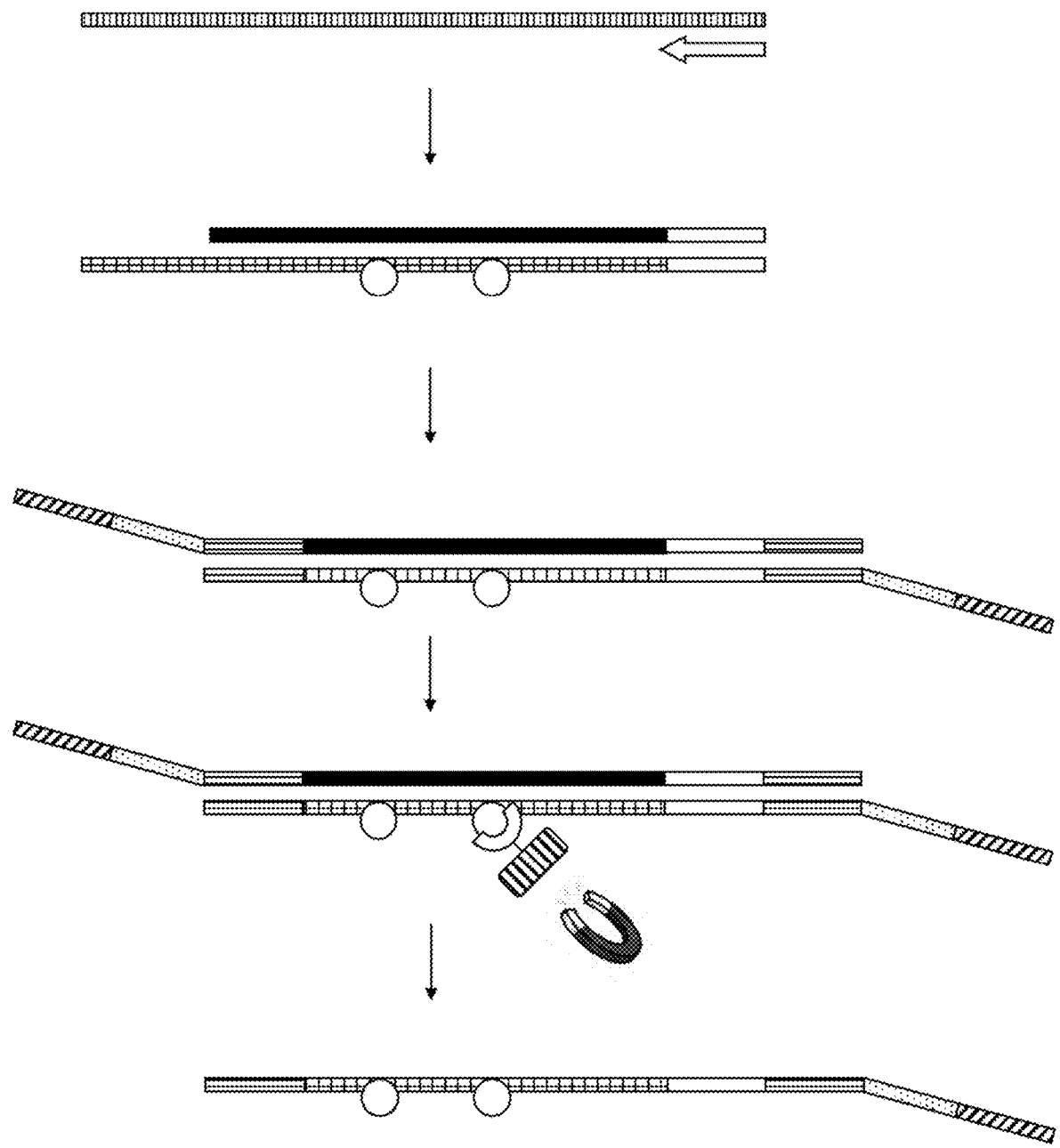
FIG. 2 is an illustration of a strategy for preparing a nucleic acid molecule for analysis using capture moiety modified nucleotides.

In some embodiments, the capture moiety of the capture moiety modified nucleotide is a biotin moiety. For example, FIG. 2 depicts a non-limiting embodiment of a method involving the use of biotin-modified nucleotides. In this embodiment, an RNA molecule (e.g., mRNA) is annealed with a DNA primer. A first strand synthesis reaction is conducted using biotinylated nucleotides to generate a biotinylated DNA/RNA hybrid. The RNA of the DNA/RNA hybrid is subjected to degradation via the action of a ribonuclease, and the RNA fragments that remain annealed to the DNA serve as primers in a second strand synthesis reaction to generate a double-stranded cDNA. In some embodiments, the second strand synthesis reaction of may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture. The double-stranded cDNA is subjected to end repair and dA-tailing to generate 3' overhangs suitable for a ligation reaction. Following ligation of an adapter nucleic acid to the double-stranded cDNA, these library molecules are captured, or isolated, from unligated adapter using a streptavidin coated paramagnetic bead.

Figure 3:
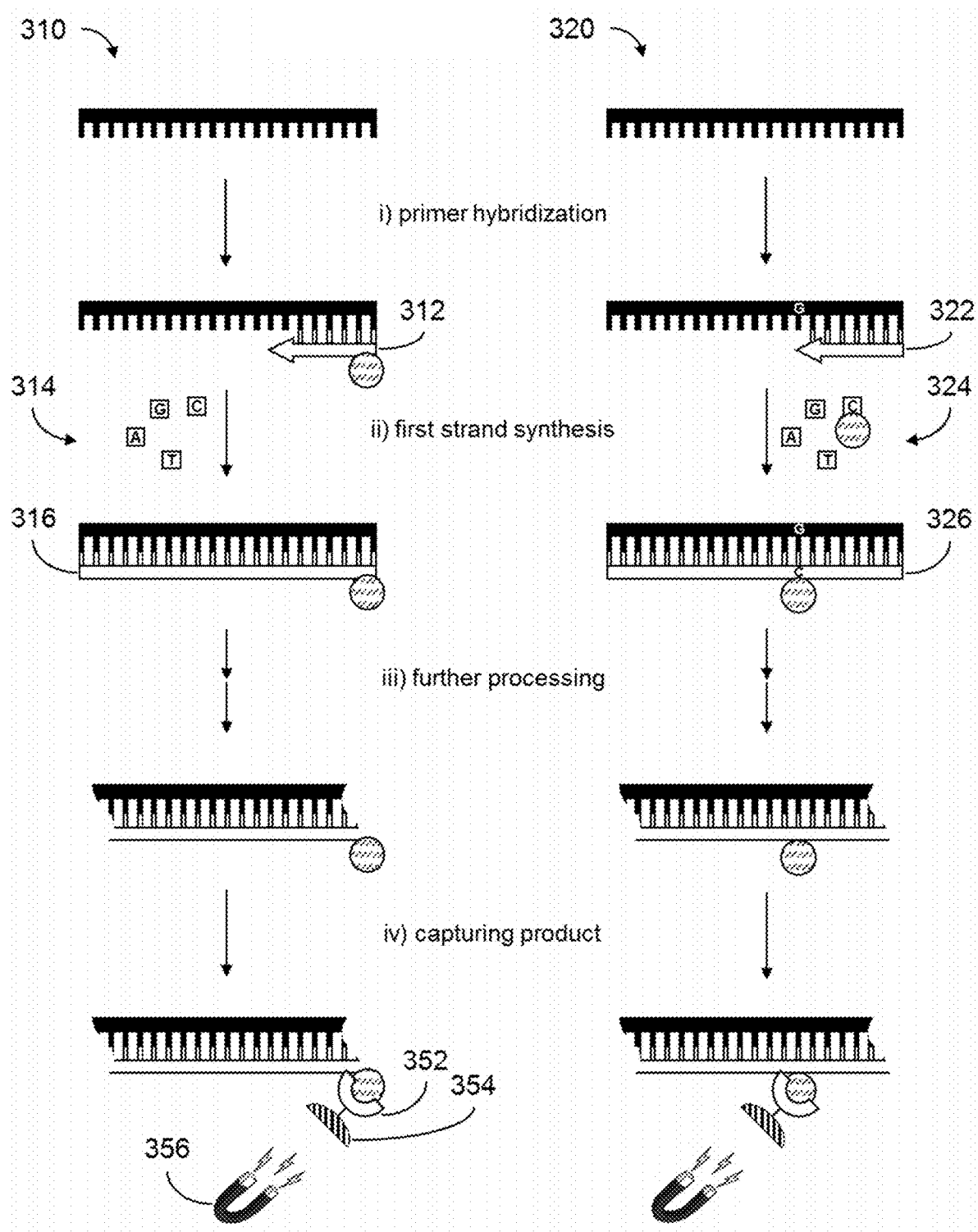
FIG. 3 illustrates a comparison of nucleic acid preparation strategies using either a capture moiety modified primer or capture moiety modified nucleotides.

As described in the foregoing, aspects of the disclosure provide techniques for preparing a nucleic acid molecule for analysis which can involve the use of a capture moiety to capture a nucleic acid product generated during a preparative process. FIG. 3 is an illustration that compares different strategies for nucleic acid preparation using capture moieties. Selected preparation steps are shown for a first process 310 which incorporates a capture moiety into a nucleic acid product using a capture moiety modified primer (e.g., as illustrated in FIG. 1) and for a second process 320 which incorporates a capture moiety into a nucleic acid product using capture moiety modified nucleotides (e.g., as illustrated in FIG. 2). In each of the first process 310 and second process 320, a nucleic acid molecule is exposed to a target specific primer under conditions to promote primer hybridization (step i)). As shown, the target specific primer of the first process 310 is a capture moiety modified primer 312, while the target specific primer of the second process 320 utilizes a first target specific primer 322 that does not include a capture moiety modification.

Following primer hybridization, a first strand synthesis reaction (step ii)) is performed in the first process 310 using a plurality of types of nucleotides 314 for incorporation into a newly synthesized first strand 316 using the nucleic acid molecule as a template. By comparison, a first strand synthesis reaction (step ii)) is performed in the second process 320 using a plurality of types of nucleotides 324, of which at least one of the plurality is a capture moiety modified nucleotide. By way of example and not limitation, a C nucleotide is shown having a capture moiety modification. In this way, during first strand synthesis using the nucleic acid molecule as a template, the capture moiety modified nucleotide is incorporated into the newly synthesized first strand 326 at a position complementary to a G nucleotide in the nucleic acid molecule.

Following first strand synthesis in either of the first process 310 or second process 320, a nucleic acid comprising the capture moiety is optionally subjected to further processing (step iii)) that involves additional modifications to the nucleic acid. Examples of further processing can include, without limitation, second strand synthesis, end-repair, adapter ligation, and other processing steps described elsewhere herein. Following the optional further processing in either of the first process 310 or second process 320, a nucleic acid product comprising the capture moiety is contacted with a binding partner of the capture moiety for the purpose of capturing the nucleic acid product (step iv)) generated from either process. As shown, product capture can be performed using a binding partner 352 of the capture moiety, which is optionally immobilized to a substrate 354. Where the substrate 354 is a paramagnetic substrate, the nucleic acid product can be isolated by exposure to a magnetic field 356.

In some aspects, the disclosure provides a method of preparing a nucleic acid library for analysis of an immune repertoire. For example, in some embodiments, the nucleic acid library is prepared from a sample comprising a nucleic acid sequence encoding an immune receptor (e.g., a TCR), an immunoglobulin (e.g., a BCR), or a mixture thereof.

Immune Repertoire

As the adaptive immune system functions in part by clonal expansion of cells expressing unique antigen binding molecules, accurately measuring the changes in total abundance of each T cell or B cell clone is important to understanding the dynamics of an adaptive immune response. Utilizing advances in high-throughput sequencing, a new field of molecular immunology has recently emerged to profile the vast TCR and BCR repertoires. In some embodiments, techniques described herein are useful for analyzing an immune cell clonotype.

As used herein, a "clonotype" refers to a successfully recombined nucleotide sequence that arises during a rearrangement process for one or more genes that encode an immune receptor chain or a portion thereof. In some embodiments, a "successfully recombined nucleotide sequence" refers to a nucleotide sequence that is comprised by mRNA and has undergone genetic recombination to produce a unique clonotype. Accordingly, in some embodiments, techniques provided in the present disclosure may be useful for detecting a successful rearrangement of an IR loci that is expressed as mRNA, but not an IR rearrangement per se. In some embodiments, a clonotype refers to a nucleotide sequence that corresponds to an mRNA encoding a single receptor chain. In some embodiments, techniques provided in the present disclosure may be useful for detecting one or more somatic hypermutations. In some embodiments, techniques provided in the present disclosure may be useful for detecting TCR and/or BCR isotypes (e.g., A, D, E, G, and M IgH isotypes, and select subclasses thereof). In some embodiments, a clonotype is a recombined nucleotide sequence of a T cell or B cell. In some embodiments, a clonotype encodes a TCR or BCR, or a portion thereof. In some embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, a VD rearrangement of TCR δ, a kappa deleting element (KDE) rearrangement, or the like. In some embodiments, clonotypes have sequences that are sufficiently long to represent or reflect the diversity of the immune molecules from which they are derived. Accordingly, in some embodiments, clonotypes may vary widely in length. In some embodiments, methods of the disclosure are useful for determining a clonotype profile.

As used herein, a "clonotype profile" refers to a listing of distinct clonotypes and their relative abundances that are derived from a population of lymphocytes. In some embodiments, the population of lymphocytes is obtained from a tissue sample. A clonotype profile is related to the immunology concept of "immune repertoire." In some embodiments, a clonotype profile includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise at least $10^3$ distinct clonotypes, at least $10^4$ distinct clonotypes, at least $10^5$ distinct clonotypes, at least $10^6$ distinct clonotypes, or at least $10^7$ distinct clonotypes. In some embodiments, clonotype profiles may comprise between about 1 and 500,000 distinct clonotypes. In some embodiments, clonotypes may comprise between about 1 and 1,000,000 distinct clonotypes (e.g., between about 1 and about 100,000, between about 100,000 and about 200,000, between about 200,000 and about 300,000, between about 300,000 and about 400,000, between about 400,000 and about 500,000, between about 500,000 and about 600,000, between about 600,000 and about 700,000, between about 700,000 and about 800,000, between about 800,000 and about 900,000, between about 900,000 and about 1,000,000 distinct clonotypes). In some embodiments, such clonotype profiles may further comprise abundances or relative frequencies of each of the distinct clonotypes. In one aspect, a clonotype profile is a set of distinct recombined nucleotide sequences (with their abundances) that encode TCRs or BCRs, or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (e.g., the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. In some embodiments, such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In some embodiments, a clonotype profile comprising nucleic acids corresponding to TCR and/or BCR chains or fragments thereof comprises a number of distinct nucleotide sequences in the range of from about 1 to about 25, about 25 to about 50, about 50 to about 100, about 11 to about 250, about 250 to about 500, about 500 to about 1000, about 1000 to about 2500, about 2500 to about 5000, about 5000 to about 7500, about 7500 to about 10000, about 10000 to about 25000, about 25000 to about 50000, about 50000 to about 100000, about 100000 to about 250000, about 250000 to about 500000, about 500000 to about 750000, about 750000 to about 1000000.

In some embodiments, a clonotype profile comprises a set of nucleotide sequences encoding substantially all segments of the V(D)J region of a BCR (e.g., an IgH chain). In one aspect, "substantially all" as used herein means every segment having a relative abundance of 0.0001 percent or higher, 0.0005 percent or higher, 0.001 percent or higher, 0.005 percent or higher, 0.01 percent or higher, 0.05 percent or higher, or 0.1 percent or higher; or in another aspect, "substantially all" as used herein means every segment having a relative abundance of 0.0001 percent or higher. In some embodiments, not all V, D, and J segments are represented. In another embodiment, a clonotype profile comprises a set of nucleotide sequences that encodes substantially all segments of the V(D)J region of a TCR (e.g., TCR β chain, TCR δ chain). In another embodiment, a clonotype profile comprises a set of nucleotide sequences having lengths in the range of from 1-25, 1-50, 1-100, 1-200, 1-300, 1-400, 1-450, 1-500, 25-100, 25-200, 25-300, 25-400, 25-450, 25-500, 100-200, 100-300, 100-400, 100-450, 100-500, 200-300, 200-400, 200-450, 200-500, 300-400, 300-450, 300-500, 400-450, 400-500, 450-500, or more nucleotides and including segments of the V, D, and J regions of a TCR (e.g., TCR β chain, TCR δ chain). In another embodiment, a clonotype profile comprises a set of nucleotide sequences having lengths in the range of from 1-25, 1-50, 1-100, 1-200, 1-300, 1-400, 1-450, 1-500, 25-100, 25-200, 25-300, 25-400, 25-450, 25-500, 100-200, 100-300, 100-400, 100-450, 100-500, 200-300, 200-400, 200-450, 200-500, 300-400, 300-450, 300-500, 400-450, 400-500, 450-500, or more nucleotides and including segments of the V, D, and J regions of a BCR (e.g., an IgH chain). In another embodiment, a clonotype profile comprises a number of distinct nucleotide sequences that is substantially equivalent to the number of lymphocytes expressing a distinct BCR (e.g., IgH chain, IgK chain, IgL chain). In another embodiment, a clonotype profile comprises a number of distinct nucleotide sequences that is substantially equivalent to the number of lymphocytes expressing a distinct TCR (e.g., TCR β chain, TCR δ chain, TCR α chain, TCR γ chain). In still another embodiment, "substantially equivalent" means that with 99 percent probability a clonotype profile will include a nucleotide sequence encoding a BCR (e.g., IgH, IgK, IgL) or TCR (e.g., TCR β, TCR δ, TCR α, TCR γ) or portion thereof carried or expressed by every lymphocyte of a population of an individual. In still another embodiment, "substantially equivalent" means that with 99 percent probability a repertoire of nucleotide sequences will include a nucleotide sequence encoding a BCR (e.g., IgH, IgK, IgL) or TCR (e.g., TCR β, TCR δ, TCR α, TCR γ) or portion thereof carried or expressed by every lymphocyte present in a sample.

In some embodiments, clonotype profiles are obtained from samples of immune cells, which are present in a wide variety of tissues. In some embodiments, immune cells of interest include T cells and/or B cells. In some embodiments, T cells (T lymphocytes) include, for example, cells that express TCRs. In some embodiments, B cells (B lymphocytes) include, for example, cells that express BCRs. In some embodiments, T-cells include helper T cells (effector T cells or Th cells), cytotoxic T cells (CTLs), memory T cells, and regulatory T cells, which may be distinguished by cell surface markers. In some embodiments, a sample of immune cells may also comprise B cells. In some embodiments, B cells include, for example, plasma B cells, memory B cells, B1 cells, B2 cells, marginal-zone B cells, and follicular B cells. B cells can express immunoglobulins (also referred to herein as antibodies or B cell receptors).

T-Cell Receptors

The adaptive immune system employs several strategies to generate a repertoire of T and B cell antigen receptors (e.g., adaptive immune receptors) with sufficient diversity to recognize the universe of potential pathogens. The ability of T cells to recognize the universe of antigens associated with various cancers or infectious organisms is conferred by its TCR, which is a heterodimer of an α (alpha) chain from the TCRA locus and β (beta) chain from the TCRB locus, or a heterodimer of a γ (gamma) chain from the TCRG locus and a δ (delta) chain from the TCRD locus. The proteins which make up these chains are encoded by DNA, which in lymphoid cells employs a unique rearrangement mechanism for generating the tremendous diversity of the TCR. This multi-subunit immune recognition receptor associates with the CD3 complex and binds to peptides presented by either the major histocompatibility complex (MHC) class I or MHC class II proteins on the surface of antigen-presenting cells (APCs). Binding of TCR to the antigenic peptide on the APC is the central event in T cell activation, which occurs at an immunological synapse at the point of contact between the T cell and the APC.

Each TCR peptide contains variable complementarity determining regions (CDRs), as well as framework regions (FRs) and a constant region. The sequence diversity of αβT cells is largely determined by the amino acid sequence of the third complementarity-determining region (CDR3) loops of the α and β chain variable domains, which diversity is a result of recombination between variable (Vβ), diversity (Dβ), and joining (Jβ) gene segments in the β chain locus, and between analogous Jα and Jα gene segments in the α chain locus, respectively. The existence of multiple such gene segments in the TCR α and β chain loci allows for a large number of distinct CDR3 sequences to be encoded. CDR3 sequence diversity is further increased by independent addition and deletion of nucleotides at the Vβ-Dβ, Dβ-Jβ, and Vα-Jα junctions during the process of TCR gene rearrangement. In this respect, immunocompetence is derived from the diversity of TCRs.

The γδ TCR heterodimer is distinctive from the αβTCR in that it encodes a receptor that interacts closely with the innate immune system, and recognizes antigen in a non-HLA-dependent manner. TCR γδ is expressed early in development, and has specialized anatomical distribution, unique pathogen and small-molecule specificities, and a broad spectrum of innate and adaptive cellular interactions. A biased pattern of TCRγ V and J segment expression is established early in ontogeny. Consequently, the diverse TCRγ repertoire in adult tissues is the result of extensive peripheral expansion following stimulation by environmental exposure to pathogens and toxic molecules.

Processes for generating diversity of a TCR are similar to those described for immunoglobulins. The TCR α chain is generated by VJ recombination, while the β chain is generated by V(D)J recombination. Similarly, generation of the TCR γ chain involves VJ recombination, while generation of the TCR δ chain occurs by V(D)J recombination. The intersection of these specific regions (V and J for the α or γ chain, V D and J for the β or δ chain) corresponds to the CDR3 region that is important for antigen-MHC recognition. It is the unique combination of the segments at this region, along with palindromic and random N- and P-nucleotide additions, which accounts for the TCR binding repertoire. Additionally, the CDR3 region begins with the second conserved cysteine in the 3' region of the vβ gene and ends with the conserved phenylalanine encoded by the 5' region of the Iβ gene. Thus, amplified sequences can be informatically translated to locate the conserved cysteine, obtain the intervening peptide sequence, and tabulate counts of each unique clone in the sample.

B-Cell Receptors

Immunoglobulins (Igs), also referred to herein as B cell receptors (BCR), are proteins expressed by B cells consisting of four polypeptide chains, two heavy chains (H chains) from the IGH locus and two light chains (L chains) from either the IGK or the IGL locus, forming an H2L2 structure. H and L chains each contain three CDRs involved in antigen recognition, as well as framework regions and a constant domain, analogous to TCR. The H chains of Igs are initially expressed as membrane-bound isoforms using either the IGM or IGD constant region exons, but after antigen recognition the constant region can class-switch to several additional isotypes, including IGG, IGE and IGA. As with TCR, the diversity of naïve Igs within an individual is mainly determined by the hypervariable CDRs. Similar to TCRB, the CDR3 domain of H chains is created by the combinatorial joining of the VH, DH, and JH gene segments. Hypervariable domain sequence diversity is further increased by independent addition and deletion of nucleotides at the VH-DH, DH-JH, and VH-JH junctions during the process of Ig gene rearrangement. Distinct from TCR, Ig sequence diversity is further augmented by somatic hypermutation (SHM) throughout the rearranged IG gene after a naïve B cell initially recognizes an antigen. The process of SHM is not restricted to CDR3, and therefore can introduce changes to the germline sequence in framework regions, CDR1 and CDR2, as well as in the somatically rearranged CDR3.

In some aspects, the DNA and RNA analyzed in the methods described herein can correspond to sequences encoding heavy chain immunoglobulins (IgH) with constant regions (α, δ, ε, γ, or μ) or light chain immunoglobulins (IgK or IgL) with constant regions (λ or κ). Each antibody has two identical light chains and two identical heavy chains. Each chain is composed of a constant (C) and a variable region. For the heavy chain, the variable region is composed of variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

In some embodiments, antibodies are produced by recombined genomic Ig sequences in B lineage cells. Immunoglobulin light chains are derived from either κ or λ genes. The λ genes are comprised of four constant (C) genes and approximately thirty variable (V) genes. In contrast, the κ genes are comprised of one C gene and 250 V genes. The heavy chain gene family is comprised of several hundred V genes, fifteen D genes, and four joining (J) genes. Somatic recombination during B cell differentiation randomly chooses one V-D-J combination in the heavy chain and one V-J combination in either κ or λ light chain. Because there are so many genes, millions of unique combinations are possible. The V genes also undergo somatic hypermutation after recombination, generating further diversity. Despite this underlying complexity, it is possible to use dozens of primers targeting conserved sequences to sequence the full heavy and light chain complement in several multiplexed reactions.

Immune Repertoire Analysis

In some aspects, techniques described herein may be used to determine the presence of a condition of interest. In some embodiments, determination of the presence of a condition of interest can relate to diagnostic applications, where a subject has or is suspected of having the condition. In some embodiments, determination of the presence of a condition of interest can be useful for predictive measures for the purpose of preventative treatment. In some embodiments, analysis of an immune repertoire can indicate the presence of a condition of interest. For example, in some embodiments, a history of cancer may be reflected in the presence of immune receptor sequences that bind to one or more cancer antigens. In some embodiments, the presence of autoimmune disease may be reflected in the presence of immune receptor sequences that bind to autoantigens. In some embodiments, conditions related to autoimmunity may be evaluated at a particular point in time or tracked over a period of time using techniques described herein. In some embodiments, conditions related to autoimmunity include multiple sclerosis (MS), celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM). Accordingly, in some embodiments, methods described herein may be used to determine whether treatment of a condition is appropriate. For example, in some embodiments, the abundance of malignant T cell and B cell may be tracked over time via specific CDR3 sequences.

In some aspects, methods provided by the disclosure may be used to determine an optimal therapeutic treatment. In some embodiments, an optimal therapeutic treatment can be determined by analyzing the immune repertoire in a sample, and based on that information, selecting an appropriate therapy, dose, or treatment modality that is optimal for stimulating or suppressing a targeted immune response while minimizing undesirable toxicity. In some embodiments, a treatment is optimized by selection for a treatment that minimizes undesirable toxicity while providing for effective activity. For example, in some embodiments, a subject (e.g., a patient) may be assessed for the immune repertoire relevant to an autoimmune disease, and a systemic or targeted immunosuppressive regimen may be selected based on that information.

In some aspects, techniques provided by the disclosure may be used to assess the progression of a condition in a subject. For example, in some embodiments, analysis of an immune repertoire can be used to assess the progression, stagnation, or regression of a condition. In such embodiments, the immune repertoire can be advantageously assessed before, during, and/or after treatment with a therapeutic to assess the effectiveness of the therapeutic in treating the condition. For example, in some embodiments, methods described herein can be useful for detecting the earliest changes along a disease pathway (e.g., a carcinogenesis pathway, inflammatory pathway, etc.), and/or to monitor the efficacy of various therapies and preventive interventions.

In some aspects, the methods disclosed herein can also be utilized to analyze the effects of agents on cells of the immune system. For example, in some embodiments, analysis of changes in immune repertoire following exposure to one or more test compounds can performed to analyze the effect(s) of the test compounds on an individual. In such embodiments, these analyses can be useful for multiple purposes, for example in the development of immunosuppressive or immune enhancing therapies. In some embodiments, agents to be analyzed for potential therapeutic value can be any compound, small molecule, protein, lipid, carbohydrate, nucleic acid, or other agent appropriate for therapeutic use. In some embodiments, tests are performed in vivo, e.g. using an animal model, to determine effects on the immune repertoire.

In some embodiments, analysis of an immune repertoire can be used to determine the effects of an antigen challenge in an organism. In some embodiments, nucleic acids are obtained from an organism after the organism has been challenged with an antigen (e.g., following vaccination). In some embodiments, nucleic acids are obtained from an organism before the organism has been challenged with an antigen. In some embodiments, comparing the diversity of the immune repertoire present before and after challenge may assist the analysis of the organism's response to the challenge.

Capture Moiety

Aspects of the techniques described herein relate to the use of a capture moiety to isolate a molecule of interest (e.g., a nucleic acid, a ligation product, etc.). As used herein, a "capture moiety" refers to a moiety that is configured to selectively interact with a binding partner for the purpose of capturing (e.g., isolating/purifying) the molecule of interest.

A capture moiety and a binding partner of the capture moiety may comprise any suitable binding pair. In some embodiments, a binding pair can selectively interact through covalent or non-covalent binding. In some embodiments, a binding pair can selectively interact by hybridization, ionic bonding, hydrogen bonding, van der Waals interactions, or any combination of these forces. In some embodiments, a capture moiety and/or binding partner can comprise, for example, biotin, avidin, streptavidin, digoxigenin, inosine, avidin, GST sequences, modified GST sequences, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

In some embodiments, a capture moiety comprises a biotin moiety. In some embodiments, techniques described herein are useful in preparing nucleic acid samples for analysis. Accordingly, in some embodiments, a nucleic acid molecule comprises a biotin capture moiety. In some embodiments, the nucleic acid molecule comprises at least one capture moiety modified nucleotide comprising a biotin moiety. In some embodiments, the capture moiety modified nucleotide comprises the general structure of formula (I):

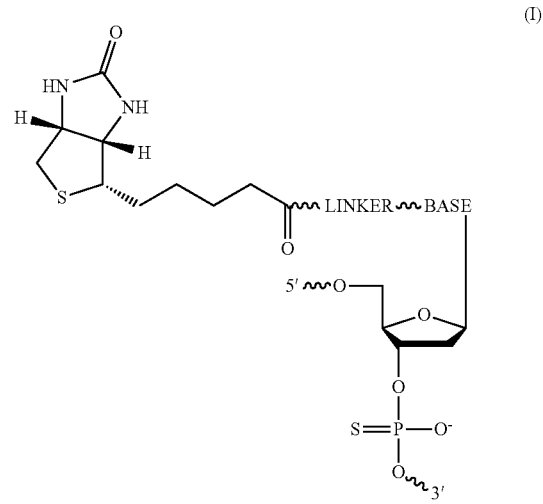

As shown in formula (I), a capture moiety modified nucleotide may comprise a biotin moiety attached to a nucleobase of a nucleotide. For example, in some embodiments, the biotin moiety comprises biotin-triethylene glycol, bis-biotin, photocleavable biotin, desthiobiotin, desthiobiotin-triethylene glycol, or biotin azide. Non-limiting examples of capture moiety modified nucleotides are shown in Table 1.

TABLE 1
Example structures of capture moiety modified nucleotides
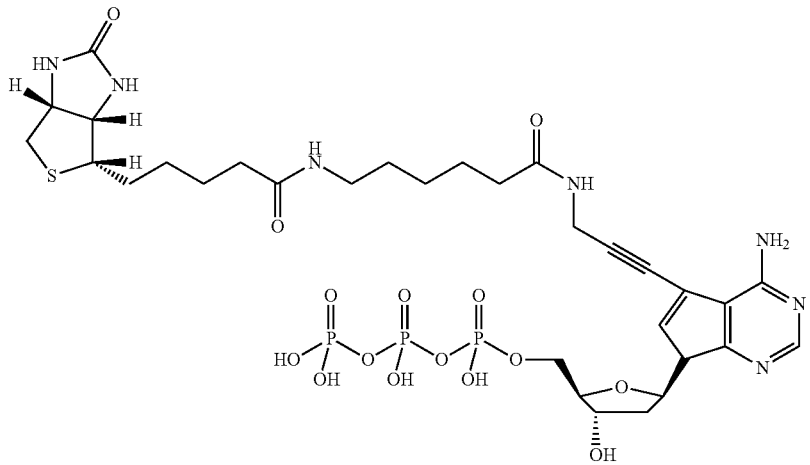 [SMILES: Nc1ncnc2c1C(C#CCNC(=O)CCCCCNC(=O)CCCC[C@@H]1SC[C@@H]3NC(=O)N[C@@H]31)=CC2[C@H]1C[C@H](O)[C@@H](COP(=O)(O)OP(=O)(O)OP(=O)(O)O)O1]
Biotin-11-dATP
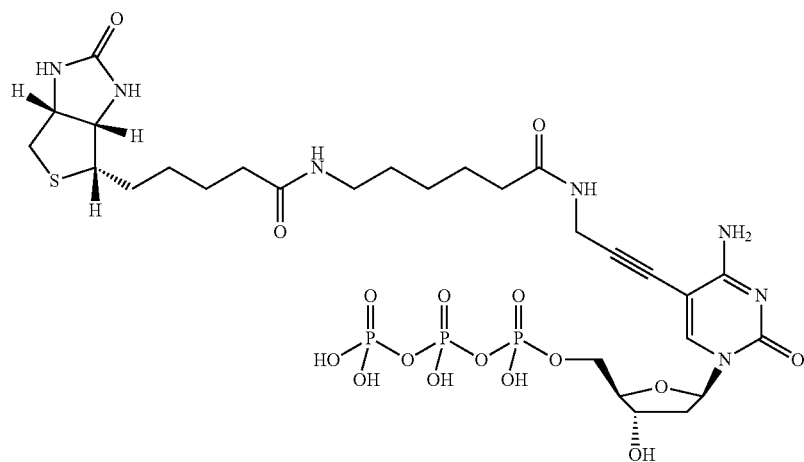 [SMILES: Nc1nc(=O)n([C@H]2C[C@H](O)[C@@H](COP(=O)(O)OP(=O)(O)OP(=O)(O)O)O2)cc1C#CCNC(=O)CCCCCNC(=O)CCCC[C@@H]1SC[C@@H]2NC(=O)N[C@@H]21]
Biotin-11-dCTP TABLE 1-continued
Example structures of capture moiety modified nucleotides
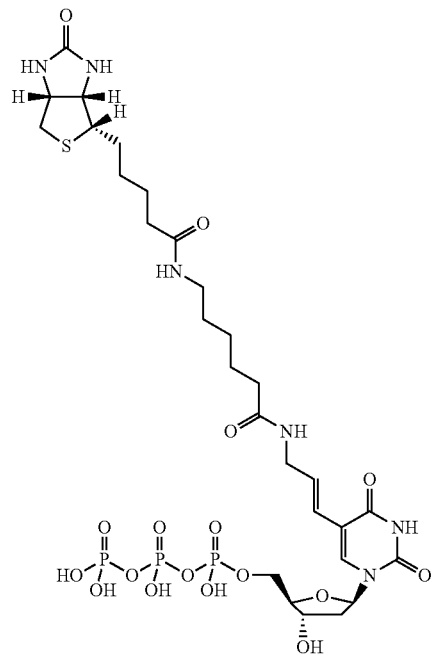 [SMILES: O=C(CCCCCNC(=O)CCCC[C@@H]1SC[C@@H]2NC(=O)N[C@@H]21)NC/C=C/c1cn([C@H]2C[C@H](O)[C@@H](COP(=O)(O)OP(=O)(O)OP(=O)(O)O)O2)c(=O)[nH]c1=O]
Biotin-11-dUTP
$C_{30}H_{45}N_8O_{16}P_3S$
898
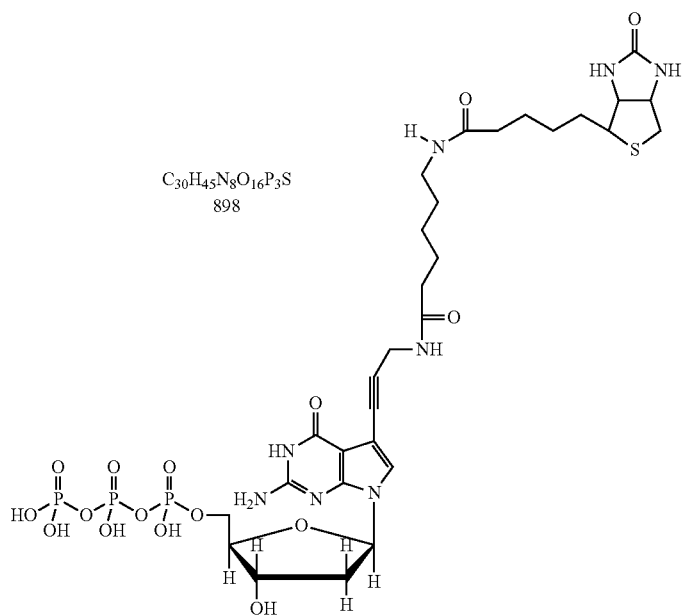
Biotin-11-dGTP TABLE 1-continued
Example structures of capture moiety modified nucleotides
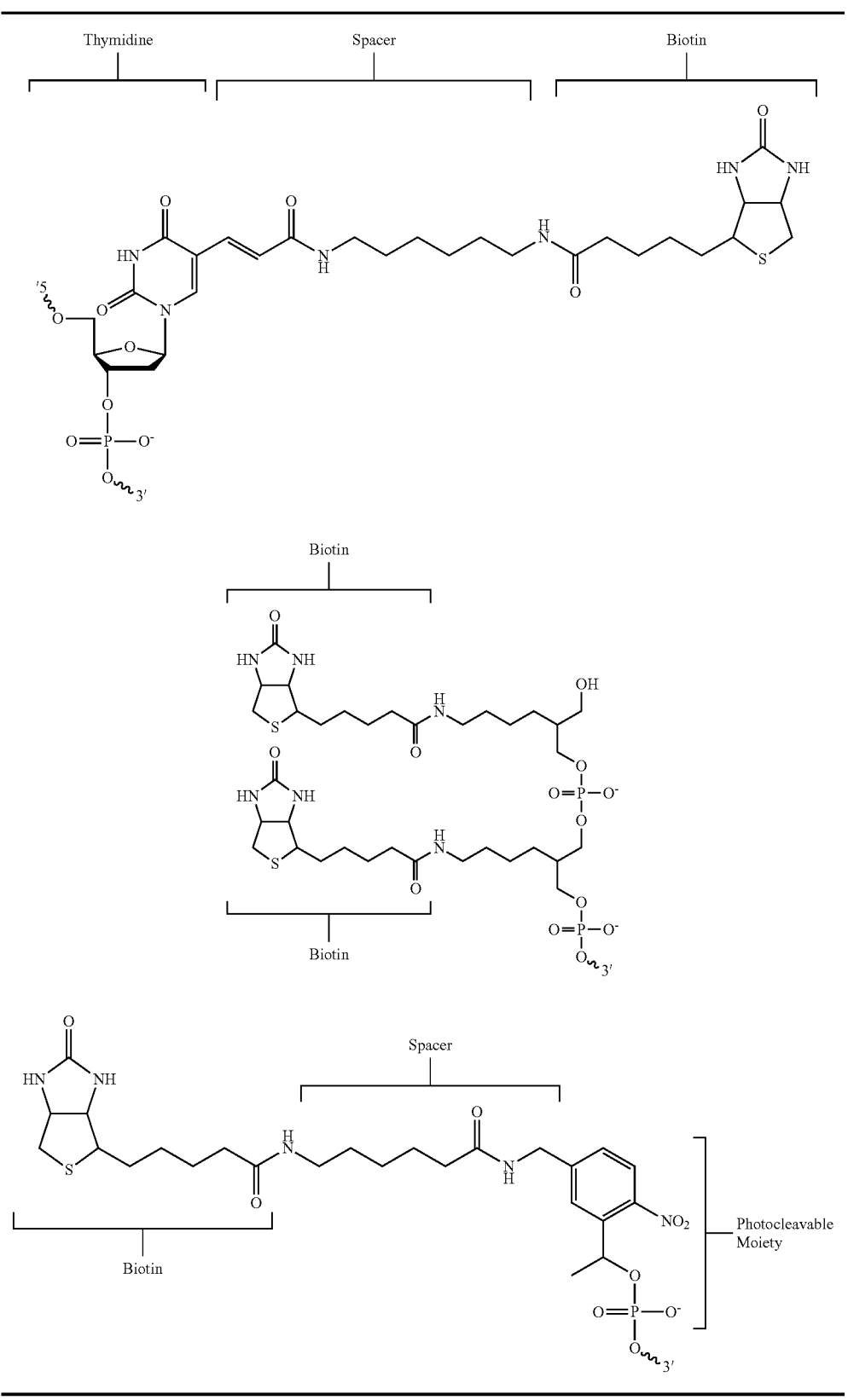

In some embodiments, a capture moiety modified nucleotide comprises a linker between the capture moiety and a nucleobase of the nucleotide. In some embodiments, the capture moiety is covalently linked to the nucleobase via a linker of any suitable length. In some embodiments, the capture moiety is covalently linked to the nucleobase via a linker of 5 to 20 atoms in length. In some embodiments, the linker comprises an aliphatic chain. In some embodiments a linker comprises —(CH$_2$)n-, wherein n is an integer from 1 to 20, inclusive. In some embodiments, n is an integer from 1 to 10, inclusive. In certain embodiments, a linker comprises a heteroaliphatic chain. In some embodiments, a linker comprises a polyethylene glycol moiety. In some embodiments, a linker comprises a polypropylene glycol moiety. In some embodiments, a linker comprises —(CH$_2$CH$_2$O)n-, wherein n is an integer from 1 to 20, inclusive. In some embodiments, a linker comprises —(CH$_2$CH$_2$O)n-, wherein n is an integer from 1 to 10, inclusive. In certain embodiments, a linker comprises one or more arylenes. In some embodiments, a linker comprises one or more phenylenes (e.g., para-substituted phenylene). In certain embodiments, a linker comprises a chiral center. In certain embodiments, a linker comprises one or more phosphates, an aliphatic chain, a heteroaliphatic chain, and one or more amides (e.g., —C(=O)NH—).

In some embodiments, a capture moiety modified nucleotide is biotin-n-dNTP, wherein n is an integer from 5 to 20 representing the number of linker atoms between a carbonyl-group of the biotin moiety and the position of attachment on a nucleobase of the NTP.

In some embodiments, a binding partner is attached to an insoluble support. Thus, in some embodiments, the molecule of interest may be immobilized on an insoluble support through a selective binding interaction formed between a capture moiety and a binding partner of the capture moiety attached to the insoluble support.

In some embodiments, the insoluble support comprises a bead or other solid surface. For example, in some embodiments, the bead is a paramagnetic bead. The use of beads for isolation is well known in the art, and any suitable bead isolation method can be used with the techniques described herein. In some embodiments, beads can be useful for isolation in that molecules of interest can be attached to the beads, and the beads can be washed to remove solution components not attached to the beads, allowing for purification and isolation. In some embodiments, the beads can be separated from other components in the solution based on properties such as size, density, or dielectric, ionic, and magnetic properties.

In some embodiments, the insoluble support is a magnetic bead. Use of beads allows the derivatized nucleic acid capture moiety to be separated from a reaction mixture by centrifugation or filtration, or, in the case of magnetic beads, by application of a magnetic field. In some embodiments, magnetic beads can be introduced, mixed, removed, and released into solution using magnetic fields. In some embodiments, processes utilizing magnetic beads may be automated. In some embodiments, the beads can be functionalized using well-known chemistry to provide a surface having suitable functionalization for attaching a binding partner of a capture moiety. Derivatization of surfaces to allow binding of the capture moiety is conventional in the art. For example, coating of surfaces with streptavidin allows binding of a biotinylated capture moiety. Coating of surfaces with streptavidin has been described in, for example, U.S. Pat. No. 5,374,524 to Miller. In some embodiments, solid surfaces other than beads may be used. In some embodiments, the solid surfaces can be planar surfaces, such as those used for hybridization microarrays, or the solid surfaces can be the packing of a separation column.

In some embodiments, a binding partner of a capture moiety may be attached to an insoluble support before, simultaneous with, or after binding the capture moiety. In some embodiments, it may be preferable to contact a capture moiety with a binding partner of the capture moiety while both are in solution. In such embodiments, the capture moiety:binding partner complex can then be immobilized on an insoluble support by contacting the complex with an appropriately derivatized surface. Thus, in some embodiments, the molecule of interest may be isolated through a complex formed between a capture moiety attached to the molecule of interest and a binding partner of the capture moiety.

In some embodiments, it may be desirable to attach the capture moiety to a nucleobase of a nucleotide. In this manner, the 3' end remains free to be optionally ligated to an adapter nucleic acid while the capture moiety is available to be captured by a binding partner. In some embodiments, the capture moiety modified nucleotide comprises a nucleobase selected from the group consisting of adenine, guanine, thymine, uracil, and cytosine, or a derivative thereof. For example, in some embodiments, the capture moiety modified nucleotide comprises an adenine nucleobase or derivative thereof. In some embodiments, the capture moiety is covalently linked to the adenine nucleobase or derivative thereof at position 5, 6, 7 or 8. In some embodiments, the capture moiety is covalently linked to the adenine nucleobase at position 7. A numbering scheme for an adenine ring is depicted in formula (II):

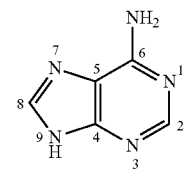

(II)

In some embodiments, it may be desirable to modify one or more positions on a nucleobase that is attached to a capture moiety. For example, in some embodiments, position 7 of the adenine nucleobase is a carbon atom. However, it should be appreciated that any atom capable of forming an additional covalent bond (e.g., C, O, N, S, etc.) may be substituted into a position on a nucleobase suitable for attachment of a capture moiety. In some embodiments, following capturing the adapter-ligated fragments, the library is subjected to amplification to enrich target nucleotide sequences.

Preparation of Nucleic Acids for Analysis

Aspects of the disclosure provide improved methods of determining the nucleotide sequence contiguous to a known target nucleotide sequence (e.g., a known target nucleotide sequence of an immune receptor). Traditional sequencing methods generate sequence information randomly (e.g., "shotgun" sequencing) or between two known sequences which are used to design primers. In contrast, certain of the methods described herein, in some embodiments, allow for determining the nucleotide sequence (e.g., sequencing) upstream or downstream of a single region of known sequence with a high level of specificity and sensitivity.

In some embodiments, the techniques described herein allow for the enrichment of target nucleotide sequences from a nucleic acid sample. In some embodiments, the nucleic acid sample comprises genomic DNA. In some embodiments, the nucleic acid sample comprises cDNA. In some embodiments, cDNA may be prepared by conducting a first strand synthesis reaction using a capture moiety modified primer that anneals to a target nucleic acid and conducting a second strand synthesis reaction using a fragment of the target nucleic acid as a primer.

Sample Purification

In some embodiments, target nucleic acids and/or amplification products thereof can be isolated from enzymes, primers, or buffer components before and/or after any appropriate step of a method. Any suitable methods for isolating nucleic acids may be used. In some embodiments, the isolation can comprise Solid Phase Reversible Immobilization (SPRI) cleanup. Methods for SPRI cleanup are well known in the art, e.g., Agencourt AMPure XP-PCR Purification (Cat No. A63880, Beckman Coulter; Brea, Calif.). In some embodiments, enzymes can be inactivated by heat treatment. In some embodiments, unlabeled dNTPs are removed by enzymatic treatment. In some embodiments, a cleanup step (e.g., an SPRI cleanup) is conducted to remove unextended or excess primers (e.g., capture moiety modified primers, target-specific primers, adapter primers, etc.).

In some embodiments, SPRI cleanup relates to the use of paramagnetic beads that bind DNA. For example, in some embodiments, SPRI cleanup utilizes beads having a polystyrene core surround by a thin layer of magnetite, which makes the beads paramagnetic (i.e., beads aggregate only when exposed to a magnetic field). In some embodiments, the bead is coated by molecules comprising carboxyl groups that provide charged groups for DNA binding. In some embodiments, SPRI cleanup is conducted in the presence of polyethylene glycol (PEG) and salt, which work together as crowding agents to activate the beads to reversibly bind DNA. In some embodiments, an SPRI comprises mixing a DNA sample with paramagnetic beads and allowing the beads to bind the DNA, applying a magnetic field to aggregate the DNA-bound beads, rinsing the beads with ethanol (e.g., 70% ethanol), and eluting the DNA from the paramagnetic beads.

In some embodiments, unhybridized primers can be removed from a nucleic acid preparation using appropriate methods (e.g., purification, digestion, etc.). In some embodiments, a nuclease (e.g., exonuclease I) is used to remove primers from a preparation. In some embodiments, such nucleases are heat inactivated subsequent to primer digestion. Once the nucleases are inactivated, a further set of primers may be added together with other appropriate components (e.g., enzymes, buffers) to perform a further amplification reaction.

In some embodiments, steps of the methods provided herein optionally comprise an intervening sample purification step. In some embodiments, a sample purification step comprises a wash step. In some embodiments, a sample purification step comprises SPRI cleanup (e.g., AMPure). For example, a method of preparing nucleic acids for analysis can comprise: (i) washing a substrate immobilized nucleic acid; and (ii) releasing the washed immobilized nucleic acid from the paramagnetic substrate or surface.

Nucleic Acid Adapter

As used herein, the term "adapter nucleic acid," "nucleic acid adapter," or "adapter" refers to a nucleic acid molecule that may be ligated to a nucleic acid comprising a target nucleotide sequence to provide one or more elements useful during amplification and/or sequencing of the target nucleotide sequence. In some embodiments, an adapter is single-stranded. In some embodiments, an adapter is double-stranded. In some embodiments, a double-stranded adapter comprises a first ligatable duplex end and a second unpaired end. In some embodiments, an adapter comprises an amplification strand and a blocking strand. In some embodiments, the amplification strand comprises a 5' unpaired portion and a 3' duplex portion. In some embodiments, the amplification strand further comprises a 3' overhang. In some embodiments, the 3' overhang is a 3' T overhang. In some embodiments, the amplification strand comprises nucleotide sequences identical to a first and second adapter primer. In some embodiments, the blocking strand of the adapter comprises a 5' duplex portion and a non-extendable 3' portion. In some embodiments, the blocking strand further comprises a 3' unpaired portion. In some embodiments, the duplex portions of the amplification strand and the blocking strand are substantially complementary and the duplex portion is of sufficient length to remain in duplex form at the ligation temperature.

In some embodiments, the portion of the amplification strand that comprises a nucleotide sequence identical to a first and second adapter primer can be comprised, at least in part, by the 5' unpaired portion of the amplification strand.

In some embodiments, the adapter can have a "Y" shape, i.e., the second unpaired end comprises a 5' unpaired portion of an amplification strand and a 3' portion of a blocking strand. The 3' unpaired portion of the blocking strand can be shorter than, longer than, or equal in length to the 5' unpaired portion of the amplification strand. In some embodiments, the 3' unpaired portion of the blocking strand can be shorter than the 5' unpaired portion of the amplification strand. Y-shaped adapters have the advantage that the unpaired portion of the blocking strand will not be subject to 3' extension during a PCR regimen.

In some embodiments, the blocking strand of the adapter can further comprise a 3' unpaired portion that is not substantially complementary to the 5' unpaired portion of the amplification strand, wherein the 3' unpaired portion of the blocking strand is not substantially complementary to or substantially identical to any of the primers. In some embodiments, the blocking strand can further comprise a 3' unpaired portion that does not specifically anneal to the 5' unpaired portion of the amplification strand at the annealing temperature, wherein the 3' unpaired portion of the blocking strand will not specifically anneal to any of the primers or the complements thereof at the annealing temperature. In some embodiments, an adapter nucleic acid comprises, at a minimum, a sample index sequence for multiplexing. However, in some embodiments, the adapter nucleic further comprises a random molecular barcode.

Extension and Amplification

Aspects of the present disclosure relate to techniques that may comprise one or more extension reactions (e.g., first strand synthesis, second strand synthesis) and/or one or more rounds of amplification. As described herein, extension reactions and amplification may be conducted using one or more target-specific primers.

As used herein, a "target-specific primer" refers to a primer comprising a sequence that is complementary to a target nucleotide sequence. In some embodiments, a target-specific primer is used to prime a first strand synthesis reaction. For example, in some embodiments, the target-specific primer is a reverse transcriptase primer that anneals to an mRNA molecule comprising a target nucleotide sequence. In some embodiments, as described herein, a capture moiety modified primer is a target-specific primer that may be used to prime a first strand synthesis reaction. In some embodiments, a target-specific primer is used to prime an amplification reaction. For example, in some embodiments, methods described herein may include a step of amplification that uses a target-specific primer that comprises a 3' portion that specifically anneals to the target nucleotide sequence. In some embodiments, the disclosure provides methods that may include the use of target-specific primers (e.g., identical or different target-specific primers) in more than one step.

Accordingly, in some embodiments of the methods described herein, where the term target-specific primer appears in more than one step and refers to separate primers, additional terminology may be included for clarification. For example, in some embodiments, an initial target-specific primer may be used in a first strand synthesis reaction to generate a cDNA that is subsequently amplified using a disparate target-specific primer. In such embodiments, the initial target-specific primer may be referred to as a "capture moiety modified primer" while the latter target-specific primer may be referred to as a "target-specific primer." Alternatively, in some embodiments, the initial target-specific primer and the latter target-specific primer may be referred to as a "first" and "second" target-specific primer, respectively.

It should be appreciated that, in some embodiments, use of the terms "first," "second," "third," etc. may be used relatively, such that these terms may be refer to different classes of primers depending on the context of the technique being described. For example, in some embodiments, a target-specific reverse transcriptase primer is used with an mRNA molecule to generate a cDNA, which is further subjected to PCR reactions using additional target-specific primers. In such embodiments, the target-specific reverse transcriptase primer may be referred to as a "first target-specific primer" with subsequent PCR primers binding to a known target sequence referred to as a "second target-specific primer," "third target-specific primer," etc. In some embodiments, a plurality of random reverse transcriptase primers are used with an mRNA molecule to generate a cDNA, which is further subjected to PCR reactions using target-specific primers. In such embodiments, the plurality of random primers are not referred to as being "target-specific"; accordingly, if subsequent PCR reactions utilize target-specific primers, the terms "first target-specific primer," "second target-specific primer," etc. may be used according to distinct reactions (e.g., in a method of preparing nucleic acids for sequencing).

In some aspects, the disclosure provides methods that may include conducting a first strand synthesis reaction using a first target-specific primer (e.g., a capture moiety modified primer). In some embodiments, a first round of amplification is conducted using a second target-specific primer (e.g., a target-specific primer) and a first adapter primer.

In some embodiments, a "target-specific primer" is an oligonucleotide comprising a nucleic acid sequence that can specifically anneal, under suitable annealing conditions, to a target nucleotide sequence of a nucleic acid molecule (e.g., a template nucleic acid). In some embodiments, ordinal terms (e.g., first, second, third) may be used to distinguish one target-specific primer from another used in different steps of a multi-step method. For example, in some embodiments, a second target-specific primer is a target specific primer for use in an amplification reaction in a process comprising a prior first strand synthesis involving use of a first target-specific primer. In such embodiments, during amplification, the second target-specific primer generates a strand that is complementary to its template, and this complementary strand is capable of being hybridized with a first adapter primer.

As used herein, an "adapter primer" is an oligonucleotide comprising a nucleic acid sequence that can specifically anneal, under suitable annealing conditions, to a complementary sequence of an adapter nucleic acid. In some embodiments, an adapter primer (e.g., a first adapter primer) is identical to at least a portion of the adapter, and it anneals to the complementary strand generated by a target-specific primer (e.g., a second target-specific primer) to allow amplification to proceed.

In some embodiments, in the first PCR amplification cycle of the first amplification step, a second target-specific primer can specifically anneal to a template strand of a nucleic acid comprising a target nucleotide sequence. In some embodiments, depending upon the orientation with which the second target-specific primer was designed, a sequence upstream or downstream of the target nucleotide sequence will be synthesized as a strand complementary to the template strand. In some embodiments, if, during the extension phase of PCR, the 5' end of a template strand terminates in a ligated adapter, the 3' end of the newly synthesized complementary strand will comprise sequence capable of hybridizing with a first adapter primer. In subsequent PCR amplification cycles, both the second target-specific primer and the first adapter primer will be able to specifically anneal to the appropriate strands of the target nucleic acid sequence and the sequence between the known nucleotide target sequence and the adapter can be amplified. In some embodiments, a second target-specific primer comprises a 5' tail portion that does not specifically anneal to the target nucleotide sequence. For example, in some embodiments, a 5' tail portion may comprise a region that provides a primer-binding site for subsequent extension reactions (e.g., during amplification). In some embodiments, a second round of amplification is conducted using a tail primer and a second adapter primer.

As used herein, a "tail primer" is an oligonucleotide comprising a nucleic acid sequence that comprises a 3' portion that can specifically anneal, under suitable annealing conditions, to a complementary sequence of the 5' tail portion of a target-specific primer (e.g., second target-specific primer) comprised by the amplicon resulting from a preceding amplification step. In some embodiments, a tail primer comprises a 5' portion that does not specifically anneal to the complementary sequence of the 5' tail portion of the target-specific primer. In some embodiments, the 5' portion of the tail primer comprises at least one of a sample index region, a PCR primer-binding region, a molecular barcode region, and a sequencing primer site region. Although a tail primer, as used herein, generally relates to a primer that is used in a second round of PCR, it should be appreciated that the term may be used to refer to any primer that hybridizes with a sequence that is complementary to a 5' tail portion of a primer used in a preceding reaction.

In some embodiments, an adapter primer (e.g., a second adapter primer) is identical to at least a portion of the adapter, and it anneals to the complementary strand generated by the tail primer to allow amplification to proceed.

In some embodiments, a second adapter primer is nested relative to a first adapter primer. In some embodiments, the use of nested adapter primers eliminates the possibility of producing final amplicons that are amplifiable (e.g., during bridge PCR or emulsion PCR) but cannot be sequenced, a situation that can arise during hemi-nested methods. In other situations, hemi-nested approaches using a primer identical to a sequencing primer can result in the carry-over of undesired amplification products from the first PCR step to the second PCR step and would ultimately yield artificial sequencing reads. In some embodiments, a second adapter primer is nested with respect to a first adapter primer by at least 1 nucleotide, e.g., by 1, 2, 3, 4, 5, 6, 7, 8, 9, 10, or more nucleotides. In some embodiments, a second adapter primer is nested with respect to a first adapter primer by about 5 nucleotides to about 10 nucleotides, by about 10 nucleotides to about 15 nucleotides, by about 15 nucleotides to about 20 nucleotides, or by about 20 nucleotides or more.

Among other aspects, techniques described herein may involve the use of one or more nested primers. In some embodiments, the use of nested primers may reduce non-specific binding in PCR products due to the amplification of unexpected primer binding sites. As used herein, the term "nested" is used to describe a positional relationship between the annealing site of a primer of a primer pair and the annealing site of another primer of another primer pair. For example, in some embodiments, a second primer is nested by 1, 2, 3 or more nucleotides relative to a first primer, meaning that it binds to a site on the template strand that is frame-shifted by 1, 2, 3 or more nucleotides.

In some embodiments, a target-specific primer (e.g., a second target-specific primer) comprises a 3' portion that specifically anneals to a target nucleotide sequence and a 5' tail that does not anneal to the target nucleotide sequence. In some embodiments, the 5' tail comprises a nucleic acid sequence that is identical to a 3' portion of a tail primer. In some embodiments, multiple primers (e.g., one or more target specific primers and/or one or more adapter primers) present in a reaction can comprise identical 5' tail sequence portions.

In some embodiments, a 5' tail can be a GC-rich sequence. In some embodiments, a 5' tail sequence may comprise at least 50% GC content, at least 55% GC content, at least 60% GC content, at least 65% GC content, at least 70% GC content, at least 75% GC content, at least 80% GC content, or higher GC content. In some embodiments, a 5' tail sequence may comprise at least 60% GC content. In some embodiments, a 5' tail sequence may comprise at least 65% GC content.

In some embodiments, a first round of amplification includes a second target-specific primer comprising a 5' tail, a first adapter primer, and an additional primer. In some embodiments, the additional primer comprises a 3' portion that is identical to the 5' tail of the second target-specific primer. In some embodiments, the additional primer may comprise additional sequences 5' to the hybridization sequence that may include barcode, index, adapter sequences, or sequencing primer sites. In some embodiments, the additional primer is a generic sequencing adapter/index primer.

In some embodiments, two target-specific primers (e.g., first and second target-specific primers) are substantially complementary to the same strand of the target nucleic acid. In some embodiments, the portions of the first and second target-specific primers that specifically anneal to the known target sequence can comprise a total of at least 20 unique bases of the known target nucleotide sequence, e.g., 20 or more unique bases, 25 or more unique bases, 30 or more unique bases, 35 or more unique bases, 40 or more unique bases, or 50 or more unique bases. In some embodiments, the portions of the first and second target-specific primers that specifically anneal to the known target sequence can comprise a total of at least 30 unique bases of the known target nucleotide sequence.

In some embodiments, the first adapter primer can comprise a nucleic acid sequence identical to about the 20 5'-most bases of the amplification strand of the adapter and the second adapter primer can comprise a nucleic acid sequence identical to about 30 bases of the amplification strand of the adapter, with a 5' base that is at least 1 nucleotide 3' of the 5' terminus of the amplification strand.

In some embodiments, an adapter ligated nucleic acid (e.g., a ligation product) is minimal. In such embodiments, a first adapter primer may be used that contains a portion of the adapter nucleic sequence at its 3' end and then additional sequencer-important information at its 5' end. In such embodiments, a second adapter primer may be used that contains, at its 3' end, the 5' end of the first adapter primer. In such embodiments, the second adapter primer may also have a nucleotide sequence that permits sequencing at its 5' end. In such embodiments, it is possible to produce, using PCR, a library that is sequencer compatible.

Primers

In general, a primer comprising a sequence that is complementary to a sequence of interest (e.g., a target sequence or an adapter sequence) can either consist of only a complementary sequence or also can include an additional sequence that is not complementary to the sequence of interest (e.g., a tail sequence, an adapter sequence, an index sequence, etc.). In some embodiments, a primer can also include non-nucleotide moieties (e.g., capture moieties, etc.).

In some embodiments, primers (e.g., first and second target-specific primers, first and second adapter primers, tail primers, capture moiety modified primers) are designed such that they will specifically anneal to their complementary sequences at an annealing temperature of from about 61 to 72° C., e.g., from about 61 to 69° C., from about 63 to 69° C., from about 63 to 67° C., from about 64 to 66° C. In some embodiments, primers are designed such that they will specifically anneal to their complementary sequences at an annealing temperature of less than 72° C. In some embodiments, primers are designed such that they will specifically anneal to their complementary sequences at an annealing temperature of less than 70° C. In some embodiments, primers are designed such that they will specifically anneal to their complementary sequences at an annealing temperature of less than 68° C. In some embodiments, primers are designed such that they will specifically anneal to their complementary sequences at an annealing temperature of about 65° C. In some embodiments, systems provided herein are configured to alter vessel temperature (e.g., by cycling between different temperature ranges) to facilitate primer annealing.

In some embodiments, the portions of the target-specific primers that specifically anneal to the target nucleotide sequence (e.g., known target nucleotide sequence) will anneal specifically at a temperature of about 61 to 72° C., e.g., from about 61 to 69° C., from about 63 to 69° C., from about 63 to 67° C., from about 64 to 66° C. In some embodiments, the portions of the target-specific primers that specifically anneal to the known target nucleotide sequence will anneal specifically at a temperature of about 65° C. in a PCR buffer.

In some embodiments, primers (e.g., random primers, target-specific primers) described herein comprise reverse transcriptase primers. In some embodiments, reverse transcriptase primers specifically anneal to an mRNA molecule at a temperature of about 50 to 52° C., from about 51 to 53°

C., from about 52 to 54° C., from about 53 to 55° C., from about 54 to 56° C., from about 55 to 57° C., from about 56-58° C., from about 57 to 59° C., from about 58 to 60° C. For example, in some embodiments, reverse transcriptase primers have an annealing temperature of about 53° C., about 53.5° C., about 54° C., about 54.5° C., about 56° C. In some embodiments, reverse transcriptase primers comprise one or more capture moieties (e.g., as described herein). In some embodiments, the one or more capture moieties may be attached to a reverse transcriptase primer at the 5' end of the primer nucleic acid. In some embodiments, reverse transcriptase primers comprise a phosphorothioate bond linking the 5'-most base to the adjacent 5'-penultimate base.

Nucleic Acid Extension, Amplification, and PCR in some embodiments, methods described herein comprise an extension regimen or step. In such embodiments, extension may proceed from one or more hybridized random primers, using the nucleic acid molecules which the primers are hybridized to as templates. Extension steps are described herein. In some embodiments, one or more random primers can hybridize to substantially all of the nucleic acids in a sample, many of which may not comprise a target nucleotide sequence. Accordingly, in some embodiments, extension of random primers may occur due to hybridization with templates that do not comprise a target nucleotide sequence.

In some embodiments, methods described herein may involve a polymerase chain reaction (PCR) amplification regimen, involving one or more amplification cycles. Amplification steps of the methods described herein can each comprise a PCR amplification regimen, i.e., a set of polymerase chain reaction (PCR) amplification cycles. As used herein, the term "amplification regimen" refers to a process of specifically amplifying (increasing the abundance of) a nucleic acid of interest. In some embodiments, exponential amplification occurs when products of a previous polymerase extension serve as templates for successive rounds of extension. In some embodiments, a PCR amplification regimen according to methods disclosed herein may comprise at least one, and in some cases at least 5 or more iterative cycles. In some embodiments, each iterative cycle comprises steps of: 1) strand separation (e.g., thermal denaturation); 2) oligonucleotide primer annealing to template molecules; and 3) nucleic acid polymerase extension of the annealed primers. It should be appreciated that any suitable conditions and times involved in each of these steps may be used. In some embodiments, conditions and times selected may depend on the length, sequence content, melting temperature, secondary structural features, or other factors relating to the nucleic acid template and/or primers used in the reaction. In some embodiments, an amplification regimen according to methods described herein is performed in a thermal cycler, many of which are commercially available. In some embodiments, methods described herein can comprise linear amplification. For example, in some embodiments, amplification steps performed using nested primers may be performed using linear amplification. In some embodiments, amplification may be conducted using nucleic acid sequence-based amplification (NASBA). For example, in some embodiments, amplification comprises a T7-mediated NASBA reaction.

In some embodiments, a nucleic acid extension reaction involves the use of a nucleic acid polymerase. As used herein, the phrase "nucleic acid polymerase" refers to an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and are commercially available. One group of nucleic acid polymerases are thermostable, i.e., they retain function after being subjected to temperatures sufficient to denature annealed strands of complementary nucleic acids, e.g., 94° C., or sometimes higher. A non-limiting example of a protocol for amplification involves using a polymerase (e.g., Phoenix Taq, VeraSeq) under the following conditions: 98° C. for 30 s, followed by 14-22 cycles comprising melting at 98° C. for 10 s, followed by annealing at 68° C. for 30 s, followed by extension at 72° C. for 3 min, followed by holding of the reaction at 4° C. However, other appropriate reaction conditions may be used. In some embodiments, annealing/extension temperatures may be adjusted to account for differences in salt concentration (e.g., 3° C. higher to higher salt concentrations). In some embodiments, slowing the ramp rate (e.g., 1° C./s, 0.5° C./s, 0.28° C./s, 0.1° C./s or slower), for example, from 98° C. to 65° C., improves primer performance and coverage uniformity in highly multiplexed samples. In some embodiments, systems provided herein are configured to alter vessel temperature (e.g., by cycling between different temperature ranges, having controlled ramp up or down rates) to facilitate amplification.

In some embodiments, a nucleic acid polymerase is used under conditions in which the enzyme performs a template-dependent extension. In some embodiments, the nucleic acid polymerase is DNA polymerase I, Taq polymerase, Phoenix Taq polymerase, Phusion polymerase, T4 polymerase, T7 polymerase, Klenow fragment, Klenow exo-, phi29 polymerase, AMV reverse transcriptase, M-MuLV reverse transcriptase, HIV-1 reverse transcriptase, VeraSeq Ultra polymerase, VeraSeq HF 2.0 polymerase, EnzScript, or another appropriate polymerase. In some embodiments, a nucleic acid polymerase is not a reverse transcriptase. In some embodiments, a nucleic acid polymerase acts on a DNA template. In some embodiments, the nucleic acid polymerase acts on an RNA template. In some embodiments, an extension reaction involves reverse transcription performed on an RNA to produce a complementary DNA molecule (RNA-dependent DNA polymerase activity). In some embodiments, a reverse transcriptase is a mouse moloney murine leukemia virus (M-MLV) polymerase, AMV reverse transcriptase, RSV reverse transcriptase, HIV-1 reverse transcriptase, HIV-2 reverse transcriptase, or another appropriate reverse transcriptase.

In some embodiments, a nucleic acid amplification reaction involves cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. In some embodiments, strand separation according to methods described herein is achieved by heating the nucleic acid sample above its melting temperature ($T_m$). In some embodiments, for a sample containing nucleic acid molecules in a reaction preparation suitable for a nucleic acid polymerase, heating to 94° C. is sufficient to achieve strand separation. In some embodiments, a suitable reaction preparation contains one or more salts (e.g., 1 to 100 mM KCl, 0.1 to 10 mM $MgCl_2$), at least one buffering agent (e.g., 1 to 20 mM Tris-HCl), and a carrier (e.g., 0.01 to 0.5% BSA). A non-limiting example of a suitable buffer comprises 50 mM KCl, 10 mM Tris-HCl (pH 8.8 at 25° C.), 0.5 to 3 mM MgCl$_2$, and 0.1% BSA. A further non-limiting example of a suitable buffer comprises 50 mM KCl, 10 mM Tris-HCl (pH 8.8 at 25° C.), 0.5 to 5 mM (e.g., approximately 0.5 mM, approximately 1 mM, approximately 2 mM, approximately 3 mM, approximately 4 mM, approximately 5 mM) MgCl$_2$, and 0.1% BSA.

In some embodiments, a nucleic acid amplification involves annealing primers to nucleic acid templates having a strands characteristic of a target nucleic acid. In some embodiments, a strand of a target nucleic acid can serve as a template nucleic acid. As used herein, the term "anneal" refers to the formation of one or more complementary base pairs between two nucleic acids. In some embodiments, annealing involves two complementary or substantially complementary nucleic acid strands hybridizing together. In some embodiments, in the context of an extension reaction, annealing involves the hybridization of primer to a template such that a primer extension substrate for a template-dependent polymerase enzyme is formed. In some embodiments, conditions for annealing (e.g., between a primer and nucleic acid template) may vary based of the length and sequence of a primer. In some embodiments, conditions for annealing are based upon a $T_m$ (e.g., a calculated $T_m$) of a primer. In some embodiments, an annealing step of an extension regimen involves reducing the temperature following a strand separation step to a temperature based on the $T_m$ (e.g., a calculated $T_m$) for a primer, for a time sufficient to permit such annealing. In some embodiments, a $T_m$ can be determined using any of a number of algorithms (e.g., OLIGO™ (Molecular Biology Insights Inc. Colorado) primer design software and VENTRO NTI™ (Invitrogen, Inc. California) primer design software and programs available on the internet, including Primer3, Oligo Calculator, and NetPrimer (Premier Biosoft; Palo Alto, Calif.; and freely available on the world wide web (e.g., at premierbiosoft-.com/netprimer/netprlaunch/Help/xnetprlaunch.html)). In some embodiments, the $T_m$ of a primer can be calculated using the following formula, which is used by NetPrimer software and is described in more detail in Frieir, et al. PNAS 1986 83:9373-9377 which is incorporated by reference herein in its entirety.

$$T_m = \Delta H/(\Delta S + R^* \ln(C/4)) + 16.6 \log([K^+]/(1+0.7[K^+])) - 273.15$$

wherein: $\Delta H$ is enthalpy for helix formation; $\Delta S$ is entropy for helix formation; $R$ is molar gas constant (1.987 cal/° C.*mol); $C$ is the nucleic acid concentration; and $[K^+]$ is salt concentration. For most amplification regimens, the annealing temperature is selected to be about 5° C. below the predicted $T_m$, although temperatures closer to and above the $T_m$ (e.g., between 1° C. and 5° C. below the predicted $T_m$ or between 1° C. and 5° C. above the predicted $T_m$) can be used, as can, for example, temperatures more than 5° C. below the predicted $T_m$ (e.g., 6° C. below, 8° C. below, 10° C. below or lower). In some embodiments, the closer an annealing temperature is to the $T_m$, the more specific is the annealing. In some embodiments, the time used for primer annealing during an extension reaction (e.g., within the context of a PCR amplification regimen) is determined based, at least in part, upon the volume of the reaction (e.g., with larger volumes involving longer times). In some embodiments, the time used for primer annealing during an extension reaction (e.g., within the context of a PCR amplification regimen) is determined based, at least in part, upon primer and template concentrations (e.g., with higher relative concentrations of primer to template involving less time than lower relative concentrations). In some embodiments, depending upon volume and relative primer/template concentration, primer annealing steps in an extension reaction (e.g., within the context of an amplification regimen) can be in the range of 1 second to 5 minutes, 10 seconds to 2 minutes, or 30 seconds to 2 minutes. As used herein, "substantially anneal" refers to an extent to which complementary base pairs form between two nucleic acids that, when used in the context of a PCR amplification regimen, is sufficient to produce a detectable level of a specifically amplified product.

As used herein, the term "polymerase extension" refers to template-dependent addition of at least one complementary nucleotide, by a nucleic acid polymerase, to the 3' end of a primer that is annealed to a nucleic acid template. In some embodiments, polymerase extension adds more than one nucleotide, e.g., up to and including nucleotides corresponding to the full length of the template. In some embodiments, conditions for polymerase extension are based, at least in part, on the identity of the polymerase used. In some embodiments, the temperature used for polymerase extension is based upon the known activity properties of the enzyme. In some embodiments, in which annealing temperatures are below the optimal temperatures for the enzyme, it may be acceptable to use a lower extension temperature. In some embodiments, enzymes may retain at least partial activity below their optimal extension temperatures. In some embodiments, a polymerase extension (e.g., performed with thermostable polymerases such as Taq polymerase and variants thereof) is performed at 65° C. to 75° C. or 68° C. to 72° C. In some embodiments, methods provided herein involve polymerase extension of primers that are annealed to nucleic acid templates at each cycle of a PCR amplification regimen. In some embodiments, a polymerase extension is performed using a polymerase that has relatively strong strand displacement activity. In some embodiments, polymerases having strong strand displacement are useful for preparing nucleic acids for purposes of detecting fusions (e.g., 5' fusions). In some embodiments, polymerases having 5'→3' exonuclease activity (e.g., Taq polymerase) are useful for producing long library fragments.

In some embodiments, primer extension is performed under conditions that permit the extension of annealed oligonucleotide primers. As used herein, the term "conditions that permit the extension of an annealed oligonucleotide such that extension products are generated" refers to the set of conditions (e.g., temperature, salt and co-factor concentrations, pH, and enzyme concentration) under which a nucleic acid polymerase catalyzes primer extension. In some embodiments, such conditions are based, at least in part, on the nucleic acid polymerase being used. In some embodiments, a polymerase may perform a primer extension reaction in a suitable reaction preparation.

In some embodiments, a suitable reaction preparation contains one or more salts (e.g., 1 to 100 mM KCl, 0.1 to 10 mM MgCl$_2$), at least one buffering agent (e.g., 1 to 20 mM Tris-HCl), a carrier (e.g., 0.01 to 0.5% BSA), and one or more NTPs (e.g, 10 to 200 µM of each of dATP, dTTP, dCTP, and dGTP). A non-limiting set of conditions is 50 mM KCl, 10 mM Tris-HCl (pH 8.8 at 25° C.), 0.5 to 3 mM MgCl$_2$, 200 µM each dNTP, and 0.1% BSA at 72° C., under which a polymerase (e.g., Taq polymerase) catalyzes primer extension.

In some embodiments, a suitable reaction preparation contains one or more salts (e.g., 1 to 100 mM KCl, 0.5 to 5 mM MgCl$_2$), at least one buffering agent (e.g., 1 to 20 mM Tris-HCl), a carrier (e.g., 0.01 to 0.5% BSA), and one or more NTPs (e.g, 50 to 350 µM of each of dATP, dTTP, dCTP, and dGTP). A non-limiting set of conditions is 50 mM KCl, 10 mM Tris-HCl (pH 8.8 at 25° C.), 3 mM MgCl$_2$, 200 µM each dNTP, and 0.1% BSA at 72° C., under which a polymerase (e.g., Taq polymerase) catalyzes primer extension. A further non-limiting set of conditions is 50 mM KCl, 10 mM Tris-HCl (pH 8.8 at 25° C.), 3 mM MgCl$_2$, 266 µM dATP, 200 µM dCTP, 133 µM dGTP, 200 µM dTTP, and 0.1% BSA at 72° C., under which a polymerase (e.g., Taq polymerase) catalyzes primer extension.

In some embodiments, conditions for initiation and extension may include the presence of one, two, three or four different deoxyribonucleoside triphosphates (e.g., selected from dATP, dTTP, dCTP, and dGTP) and a polymerization-inducing agent such as DNA polymerase or reverse transcriptase, in a suitable buffer. In some embodiments, a "buffer" may include solvents (e.g., aqueous solvents) plus appropriate cofactors and reagents which affect pH, ionic strength, etc. In some embodiments, the two, three or four different deoxyribonucleoside triphosphates are present in equimolar, or approximately equimolar, concentrations. In some embodiments, the two, three or four different deoxyribonucleoside triphosphates are present in different concentrations, which have been experimentally determined to be suitable to a particular implementation of the technology.

In some embodiments, nucleic acid amplification involves up to 5, up to 10, up to 20, up to 30, up to 40 or more rounds (cycles) of amplification. In some embodiments, nucleic acid amplification may comprise a set of cycles of a PCR amplification regimen from 5 cycles to 20 cycles in length. In some embodiments, an amplification step may comprise a set of cycles of a PCR amplification regimen from 10 cycles to 20 cycles in length. In some embodiments, each amplification step can comprise a set of cycles of a PCR amplification regimen from 12 cycles to 16 cycles in length. In some embodiments, an annealing temperature can be less than 70° C. In some embodiments, an annealing temperature can be less than 72° C. In some embodiments, an annealing temperature can be about 65° C. In some embodiments, an annealing temperature can be from about 61 to about 72° C.

In various embodiments, methods and compositions described herein relate to performing a PCR amplification regimen with one or more of the types of primers described herein. As used herein, "primer" refers to an oligonucleotide capable of specifically annealing to a nucleic acid template and providing a 3' end that serves as a substrate for a template-dependent polymerase to produce an extension product which is complementary to the template. In some embodiments, a primer is single-stranded, such that the primer and its complement can anneal to form two strands. Primers according to methods and compositions described herein may comprise a hybridization sequence (e.g., a sequence that anneals with a nucleic acid template) that is less than or equal to 300 nucleotides in length, e.g., less than or equal to 300, or 250, or 200, or 150, or 100, or 90, or 80, or 70, or 60, or 50, or 40, or 30 or fewer, or 20 or fewer, or 15 or fewer, but at least 6 nucleotides in length. In some embodiments, a hybridization sequence of a primer may be 6 to 50 nucleotides in length, 6 to 35 nucleotides in length, 6 to 20 nucleotides in length, 10 to 25 nucleotides in length.

Any suitable method may be used for synthesizing oligonucleotides and primers. In some embodiments, commercial sources offer oligonucleotide synthesis services suitable for providing primers for use in methods and compositions described herein (e.g., INVITROGEN™ Custom DNA Oligos (Life Technologies, Grand Island, N.Y.) or custom DNA Oligos from Integrated DNA Technologies (Coralville, Iowa)).

Target Nucleic Acid

As used herein, the terms "target nucleic acid," "nucleic acid molecule comprising a target nucleotide sequence," and "nucleic acid comprising a target nucleotide sequence" refer to a nucleic acid molecule of interest (e.g., a nucleic acid to be prepared for analysis). In some embodiments, a target nucleic acid comprises both a target nucleotide sequence (e.g., a known or predetermined nucleotide sequence) and an adjacent nucleotide sequence that is to be determined (which may be referred to as an unknown sequence). A target nucleic acid can be of any appropriate length. In some embodiments, a target nucleic acid is double-stranded. In some embodiments, a target nucleic acid is DNA. In some embodiments, a target nucleic acid comprises genomic or chromosomal DNA (gDNA). In some embodiments, a target nucleic acid comprises complementary DNA (cDNA). In some embodiments, a target nucleic acid is single-stranded. In some embodiments, a target nucleic acid comprises RNA (e.g., mRNA, rRNA, tRNA, cfDNA, cfRNA, long non-coding RNA, microRNA).

Many of the sequencing methods suitable for use in the methods described herein provide sequencing runs with optimal read lengths of tens to hundreds of nucleotide bases (e.g., Ion Torrent technology can produce read lengths of 200-400 bp). Target nucleic acids comprised, for example, by genomic DNA or mRNA, can be comprised by nucleic acid molecules which are substantially longer than this optimal read length. In order for the amplified nucleic acid portion resulting from the second amplification step to be of a suitable length (e.g., up to 100 bp, 200 bp, 300 bp, 400 bp, 500 bp, 1 kb, 2 kb) for use in a particular sequencing technology, the average distance between the known target nucleotide sequence and an end of the target nucleic acid to which the adapter can be ligated should be as close to the optimal read length of the selected technology as possible. For example, if the optimal read-length of a given sequencing technology is 200 bp, then the nucleic acid molecules amplified in accordance with the methods described herein should have an average length of about 400 bp or less. However, it should be appreciated that, in some embodiments, techniques described herein may be implemented when nucleic acid molecules exceed 400 bp in length. For example, in some embodiments, nucleic acid fragments can be approximately 400 or more nucleotides, 500 or more nucleotides, 600 or more nucleotides, 700 or more nucleotides, 800 or more nucleotides, 900 or more nucleotides, 1000 or more nucleotides, 1500 or more nucleotides, 2000 or more nucleotides, 2500 or more nucleotides, 3000 or more nucleotides, 4000 or more nucleotides, 5000 or more nucleotides, 10000 or more nucleotides.

Target nucleic acids comprised by, e.g., genomic DNA or mRNA, can be sheared, e.g., mechanically or enzymatically sheared, to generate fragments of any desired size. Non-limiting examples of mechanical shearing processes include sonication, nebulization, and AFA™ shearing technology available from Covaris (Woburn, Mass.). In some embodiments, a target nucleic acid comprised by genomic DNA can be mechanically sheared by sonication.

In some embodiments, when the target nucleic acid is comprised by RNA, the sample can be subjected to a reverse transcriptase regimen to generate a DNA template. In some embodiments, the DNA template can then be sheared. In some embodiments, the DNA template is not sheared. For example, in some embodiments, the concentration of primers used during a reverse transcriptase regimen can be adjusted such that the product cDNA is of an appropriate "fragmented" length. In some embodiments, target RNA can be sheared before performing the reverse transcriptase regimen. In some embodiments, a sample comprising target RNA can be used in the methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers; and by subjecting the nucleic acid to end-repair, phosphorylation, and adenylation.

In some embodiments, a target nucleotide sequence can be comprised by a gene rearrangement. The methods described herein are suited for determining the presence and/or identity of a gene rearrangement as the identity of only one half of the gene rearrangement must be previously known (i.e., the half of the gene rearrangement which is to be targeted by the gene-specific primers). In some embodiments, the gene rearrangement can comprise an oncogene. In some embodiments, the gene rearrangement can comprise a fusion oncogene. In some embodiments, the gene rearrangement can comprise a V(D)J recombination product.

As used herein, the term "known target nucleotide sequence" or "target nucleotide sequence" refers to a portion of a target nucleic acid for which the sequence (e.g., the identity and order of the nucleotide bases of the nucleic acid) is known. For example, in some embodiments, a known target nucleotide sequence is a nucleotide sequence of a nucleic acid that is known or that has been determined in advance of an interrogation of an adjacent unknown sequence of the nucleic acid. A known target nucleotide sequence can be of any appropriate length.

In some embodiments, a target nucleotide sequence (e.g., a known target nucleotide sequence) has a length of 10 or more nucleotides, 30 or more nucleotides, 40 or more nucleotides, 50 or more nucleotides, 100 or more nucleotides, 200 or more nucleotides, 300 or more nucleotides, 400 or more nucleotides, 500 or more nucleotides, 600 or more nucleotides, 700 or more nucleotides, 800 or more nucleotides, 900 or more nucleotides, 1000 or more nucleotides, 1500 or more nucleotides, 2000 or more nucleotides, 2500 or more nucleotides, 3000 or more nucleotides, 4000 or more nucleotides, 5000 or more nucleotides, 10000 or more nucleotides. In some embodiments, a target nucleotide sequence (e.g., a known target nucleotide sequence) has a length in the range of 10 to 100 nucleotides, 10 to 500 nucleotides, 10 to 1000 nucleotides, 100 to 500 nucleotides, 100 to 1000 nucleotides, 500 to 1000 nucleotides, 500 to 5000 nucleotides.

In some embodiments, methods are provided herein for determining sequences of contiguous (or adjacent) portions of a nucleic acid. As used herein, the term "nucleotide sequence contiguous to" refers to a nucleotide sequence of a nucleic acid molecule (e.g., a target nucleic acid) that is immediately upstream or downstream of another nucleotide sequence (e.g., a known nucleotide sequence). In some embodiments, a nucleotide sequence contiguous to a known target nucleotide sequence may be of any appropriate length. In some embodiments, a nucleotide sequence contiguous to a known target nucleotide sequence comprises 1 kb or less of nucleotide sequence, e.g., 1 kb or less of nucleotide sequence, 750 bp or less of nucleotide sequence, 500 bp or less of nucleotide sequence, 400 bp or less of nucleotide sequence, 300 bp or less of nucleotide sequence, 200 bp or less of nucleotide sequence, 100 bp or less of nucleotide sequence. In some embodiments, in which a sample comprises different target nucleic acids comprising a known target nucleotide sequence (e.g., a cell in which a known target nucleotide sequence occurs multiple times in its genome, or on separate, non-identical chromosomes), there may be multiple sequences which comprise "a nucleotide sequence contiguous to" the known target nucleotide sequence. As used herein, the term "determining a (or the) nucleotide sequence," refers to determining the identity and relative positions of the nucleotide bases of a nucleic acid.

In some embodiments, a known target nucleic acid can contain a fusion sequence resulting from a gene rearrangement. In some embodiments, methods described herein are suited for determining the presence and/or identity of a gene rearrangement. In some embodiments, the identity of one portion of a gene rearrangement is previously known (e.g., the portion of a gene rearrangement that is to be targeted by the gene-specific primers) and the sequence of the other portion may be determined using methods disclosed herein. In some embodiments, a gene rearrangement can involve an oncogene. In some embodiments, a gene rearrangement can comprise a fusion oncogene.

Molecular Barcodes and Index Sequences

In some embodiments, primers and/or adapters may contain additional sequences such as an identifier sequence (e.g., a barcode, an index), sequencing primer hybridization sequences (e.g., Rd1), and adapter sequences. In some embodiments the adapter sequences are sequences used with a next generation sequencing system. In some embodiments, the adapter sequences are P5 and P7 sequences for Illumina-based sequencing technology. In some embodiments, the adapter sequence are P1 and A compatible with Ion Torrent sequencing technology.

In some embodiments, as used herein, "barcode," "molecular barcode," and "molecular barcode tag" may be used interchangeably, and generally refer to a region of an adapter nucleic acid that is useful as an identifier for the specific nucleic acid to which it is ligated. In some embodiments, a molecular barcode comprises a randomized nucleic acid sequence that provides a unique identifier for the nucleic acid to which it is ligated. In some embodiments, a molecular barcode may be used to identify unique fragments and "de-duplicate" the sequencing reads from a sample. In some embodiments, a molecular barcode may be used to identify and remove PCR duplicates. In some embodiments, a molecular barcode may be 2 to 25 nucleotides in length, 2 to 15 nucleotides in length, 2 to 10 nucleotides in length, 2 to 6 nucleotides in length. In some embodiments, a molecular barcode comprises at least 2, 3, 4, 5, 6, 7, 8, 9, 10, 11, 12, 13, 14, 15, 16, 17, 18, 19, 20, 21, 22, 23, 24, or at least 25 nucleotides. In some embodiments, a molecular barcode comprises 8 nucleotides.

In some embodiments, as used herein, "index," "index sequence," "index region," and "sample index" may be used interchangeably, and generally refer to a region of an adapter nucleic acid that is useful as an identifier for the population to which the ligated nucleic acid belongs. In some embodiments, an index comprises a fixed nucleic acid sequence that may be used to identify a collection of sequences belonging to a common library. For example, an index may be used to identify a sample that corresponds to a nucleic acid. In some embodiments, an index may be used, for example, as a source identifier, location identifier, date or time identifier (e.g., date or time of sampling or processing), or other identifier of a nucleic acid relating to a shared or common property (e.g., common among other nucleic acids of a library). In some embodiments, such index sequences are useful for identifying different aspects of a nucleic acid that are present in a population of nucleic acids. In some embodiments, index sequences may provide a source or location identifier for a target nucleic acid. For example, an index sequence may serve to identify a patient from whom a nucleic acid is obtained. In some embodiments, index sequences enable sequencing of multiple different samples on a single reaction (e.g., performed in a single flow cell). In some embodiments, an index sequence can be used to orientate a sequence imager for purposes of detecting individual sequencing reactions. In some embodiments, an index sequence may be 2 to 25 nucleotides in length, 2 to 15 nucleotides in length, 2 to 10 nucleotides in length, 2 to 6 nucleotides in length. In some embodiments, an index comprises at least 2, 3, 4, 5, 6, 7, 8, 9, 10, 11, 12, 13, 14, 15, 16, 17, 18, 19, 20, 21, 22, 23, 24, or at least 25 nucleotides.

In some embodiments, when a population of tailed random primers is used in accordance with methods described herein, multiple distinguishable amplification products can be present after amplification. In some embodiments, because tailed random primers hybridize at various positions throughout nucleic acid molecules of a sample, a set of target-specific primers can hybridize (and amplify) the extension products created by more than 1 hybridization event, e.g., one tailed random primer may hybridize at a first distance (e.g., 100 nucleotides) from a target-specific primer hybridization site, and another tailed random primer can hybridize at a second distance (e.g., 200 nucleotides) from a target-specific primer hybridization site, thereby resulting in two amplification products (e.g., a first amplification product comprising about 100 bp and a second amplification product comprising about 200 bp). In some embodiments, these multiple amplification products can each be sequenced using next generation sequencing technology. In some embodiments, sequencing of these multiple amplification products is advantageous because it provides multiple overlapping sequence reads that can be compared with one another to detect sequence errors introduced during amplification or sequencing processes. In some embodiments, individual amplification products (e.g., derived from a single molecule) can be aligned and where they differ in the sequence present at a particular base, an artifact or error of PCR and/or sequencing may be present.

DNA Shearing/Fragmentation

The nucleic acid molecules described herein can be sheared (e.g., mechanically or enzymatically sheared, sheared via nebulizer) to generate fragments of any desired size. Non-limiting examples of mechanical shearing processes include sonication, nebulization, and AFA™ shearing technology available from Covaris (Woburn, Mass.). In some embodiments, a nucleic acid can be mechanically sheared by sonication. In some embodiments, a target nucleic acid is not sheared or digested. In some embodiments, nucleic acid products of preparative steps (e.g., extension products, amplification products) are not sheared or enzymatically digested.

In some embodiments, when a target nucleotide sequence comprises RNA, the sample can be subjected to a reverse transcriptase regimen to generate a DNA template and the DNA template can then be sheared. In some embodiments, target RNA can be sheared before performing a reverse transcriptase regimen. In some embodiments, a sample comprising target RNA can be used in methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers.

Sequencing

In some aspects, the technology described herein relates to methods of enriching nucleic acid samples for oligonucleotide sequencing. In some embodiments, the sequencing can be performed by a next-generation sequencing method. As used herein, "next-generation sequencing" refers to oligonucleotide sequencing technologies that have the capacity to sequence oligonucleotides at speeds above those possible with conventional sequencing methods (e.g., Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ION Torrent); DNA nanoball sequencing (Complete Genomics); and technologies available from Pacific Biosciences, Intelligen Biosystems, and Oxford Nanopore Technologies. In some embodiments, the sequencing primers can comprise portions compatible with the selected next-generation sequencing method. Next-generation sequencing technologies and the constraints and design parameters of associated sequencing primers are well known in the art (see, e.g., Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/0252077; 2007/0070349; and 20070070349; which are incorporated by reference herein in their entireties).

In some embodiments, the sequencing step relies upon the use of a first and second sequencing primer. In some embodiments, the first and second sequencing primers are selected to be compatible with a next-generation sequencing method as described herein.

Methods of aligning sequencing reads to known sequence databases of genomic and/or cDNA sequences are well known in the art, and software is commercially available for this process. In some embodiments, reads (less the sequencing primer and/or adapter nucleotide sequence) which do not map, in their entirety, to wild-type sequence databases can be genomic rearrangements or large indel mutations. In some embodiments, reads (less the sequencing primer and/or adapter nucleotide sequence) comprising sequences which map to multiple locations in the genome can be genomic rearrangements. In some embodiments, a de novo assembly of reads overlapping into contiguous sequences, or "contigs," may be built and utilized in the alignment of sequencing reads. In some embodiments, a hot spot reference may be utilized that does not rely on a publicly accessible genomics database.

Samples

In some embodiments, a nucleic acid (e.g., target nucleic acid, nucleic acid comprising a target nucleotide sequence) is present in or obtained from an appropriate sample (e.g., a food sample, environmental sample, biological sample e.g., blood sample, etc.). In some embodiments, the target nucleic acid is a biological sample obtained from a subject. In some embodiments a sample can be a diagnostic sample obtained from a subject. In some embodiments, a sample can further comprise proteins, cells, fluids, biological fluids, preservatives, and/or other substances. By way of non-limiting example, a sample can be a cheek swab, blood, serum, plasma, sputum, cerebrospinal fluid, urine, tears, alveolar isolates, pleural fluid, pericardial fluid, cyst fluid, tumor tissue, tissue, a biopsy, saliva, an aspirate, or combinations thereof. In some embodiments, a sample can be obtained by resection or biopsy.

In some embodiments, the sample can be obtained from a subject in need of treatment for a disease associated with a genetic alteration, e.g., cancer or a hereditary disease. In some embodiments, a known target sequence is present in a disease-associated gene.

In some embodiments, a sample is obtained from a subject in need of treatment for cancer. In some embodiments, the sample comprises a population of tumor cells, e.g., at least one tumor cell. In some embodiments, the sample comprises a tumor biopsy, including but not limited to, untreated biopsy tissue or treated biopsy tissue (e.g., formalin-fixed and/or paraffin-embedded biopsy tissue).

In some embodiments, the sample is freshly collected. In some embodiments, the sample is stored prior to being used in methods and compositions described herein. In some embodiments, the sample is an untreated sample. As used herein, "untreated sample" refers to a biological sample that has not had any prior sample pre-treatment except for dilution and/or suspension in a solution. In some embodiments, a sample is obtained from a subject and preserved or processed prior to being utilized in methods and compositions described herein. By way of non-limiting example, a sample can be embedded in paraffin wax, refrigerated, or frozen. A frozen sample can be thawed before determining the presence of a nucleic acid according to methods and compositions described herein. In some embodiments, the sample can be a processed or treated sample. Exemplary methods for treating or processing a sample include, but are not limited to, centrifugation, filtration, sonication, homogenization, heating, freezing and thawing, contacting with a preservative (e.g., anti-coagulant or nuclease inhibitor) and any combination thereof. In some embodiments, a sample can be treated with a chemical and/or biological reagent. Chemical and/or biological reagents can be employed to protect and/or maintain the stability of the sample or nucleic acid comprised by the sample during processing and/or storage. In addition, or alternatively, chemical and/or biological reagents can be employed to release nucleic acids from other components of the sample. By way of non-limiting example, a blood sample can be treated with an anti-coagulant prior to being utilized in methods and compositions described herein.

Suitable methods and processes for processing, preservation, or treatment of samples for nucleic acid analysis may be used in the method disclosed herein. In some embodiments, a sample can be a clarified fluid sample. In some embodiments, a sample can be clarified by low-speed centrifugation (e.g., 3,000×g or less) and collection of the supernatant comprising the clarified fluid sample.

In some embodiments, a nucleic acid present in a sample can be isolated, enriched, or purified prior to being utilized in methods and compositions described herein. Suitable methods of isolating, enriching, or purifying nucleic acids from a sample may be used. For example, kits for isolation of genomic DNA from various sample types are commercially available (e.g., Catalog Nos. 51104, 51304, 56504, and 56404; Qiagen; Germantown, Md.).

In some embodiments, methods described herein relate to methods of enriching for target nucleic acids, e.g., prior to a sequencing of the target nucleic acids. In some embodiments, a sequence of one end of the target nucleic acid to be enriched is not known prior to sequencing. In some embodiments, methods described herein relate to methods of enriching specific nucleotide sequences prior to determining the nucleotide sequence using a next-generation sequencing technology. In some embodiments, methods of enriching specific nucleotide sequences do not comprise hybridization enrichment.

Target genes and Therapeutic Applications

Aspects of the disclosure may be useful in the genetic analysis of an immune system. However, it should be appreciated that the techniques described herein may be applied to any target gene or nucleic acid of interest. In some embodiments of techniques described herein, a determination of the sequence contiguous to a known oligonucleotide target sequence can provide information relevant to treatment of disease. Thus, in some embodiments, methods disclosed herein can be used to aid in treating disease. In some embodiments, a sample can be from a subject in need of treatment for a disease associated with a genetic alteration. In some embodiments, a known target sequence is a sequence of a disease-associated gene, e.g., an oncogene. In some embodiments, a sequence contiguous to a known oligonucleotide target sequence and/or the known oligonucleotide target sequence can comprise a mutation or genetic abnormality which is disease-associated, e.g., a SNP, an insertion, a deletion, and/or a gene rearrangement. In some embodiments, a sequence contiguous to a known target sequence and/or a known target sequence present in a sample comprised sequence of a gene rearrangement product. In some embodiments, a gene rearrangement can be an oncogene, e.g., a fusion oncogene.

Certain treatments for cancer are particularly effective against tumors comprising certain oncogenes, e.g., a treatment agent which targets the action or expression of a given fusion oncogene can be effective against tumors comprising that fusion oncogene but not against tumors lacking the fusion oncogene. Methods described herein can facilitate a determination of specific sequences that reveal oncogene status (e.g., mutations, SNPs, and/or rearrangements). In some embodiments, methods described herein can further allow the determination of specific sequences when the sequence of a flanking region is known, e.g., methods described herein can determine the presence and identity of gene rearrangements involving known genes (e.g., oncogenes) in which the precise location and/or rearrangement partner are not known before methods described herein are performed.

In some embodiments, a subject is in need of treatment for lung cancer (e.g., with EGFR-TKI, a targeted cancer therapy). In some embodiments, e.g., when the sample is obtained from a subject in need of treatment for lung cancer, the known target sequence can comprise a sequence from a gene selected from the group of ALK, ROS1, and RET. Accordingly, in some embodiments, gene rearrangements result in fusions involving the ALK, ROS1, or RET. Non-limiting examples of gene arrangements involving ALK, ROS1, or RET are described in, e.g., Soda et al. Nature 2007 448561-6: Rikova et al. Cell 2007 131:1190-1203; Kohno et al. Nature Medicine 2012 18:375-7; Takouchi et al. Nature Medicine 2012 18:378-81; which are incorporated by reference herein in their entireties. However, it should be appreciated that the precise location of a gene rearrangement and the identity of the second gene involved in the rearrangement may not be known in advance. Accordingly, in methods described herein, the presence and identity of such rearrangements can be detected without having to know the location of the rearrangement or the identity of the second gene involved in the gene rearrangement.

In some embodiments, the known target sequence can comprise sequence from a gene selected from the group of: ALK, ROS1, and RET.

In some embodiments, the presence of a gene rearrangement of ALK in a sample obtained from a tumor in a subject can indicate that the tumor is susceptible to treatment with a treatment selected from the group consisting of: an ALK inhibitor; EGFR; crizotinib (PF-02341066); AP26113; LDK378; 3-39; AF802; IPI-504; ASP3026; AP-26113; X-396; GSK-1838705A; CH5424802; diamino and aminopyrimidine inhibitors of ALK kinase activity such as NVP-TAE684 and PF-02341066 (see, e.g., Galkin et al., Proc Natl Acad Sci USA, 2007, 104:270-275; Zou et al., Cancer Res, 2007, 67:4408-4417; Hallberg and Palmer F1000 Med Reports 2011 3:21; Sakamoto et al., Cancer Cell 2011 19:679-690; and molecules disclosed in WO 04/079326). All of the foregoing references are incorporated by reference herein in their entireties. An ALK inhibitor can include any agent that reduces the expression and/or kinase activity of ALK or a portion thereof, including, e.g., oligonucleotides, small molecules, and/or peptides that reduce the expression and/or activity of ALK or a portion thereof. As used herein "anaplastic lymphoma kinase" or "ALK" refers to a transmembrane tyROS line kinase typically involved in neuronal regulation in the wildtype form. The nucleotide sequence of the ALK gene and mRNA are known for a number of species, including human (e.g., as annotated under NCBI Gene ID: 238).

In some embodiments, the presence of a gene rearrangement of ROS1 in a sample obtained from a tumor in a subject can indicate that the tumor is susceptible to treatment with a treatment selected from the group consisting of: a ROS1 inhibitor and an ALK inhibitor as described herein above (e.g., crizotinib). A ROS1 inhibitor can include any agent that reduces the expression and/or kinase activity of ROS1 or a portion thereof, including, e.g., oligonucleotides, small molecules, and/or peptides that reduce the expression and/or activity of ROS1 or a portion thereof. As used herein "c-ros oncogene 1" or "ROS1" (also referred to in the art as ros-1) refers to a transmembrane tyrosine kinase of the sevenless subfamily and which interacts with PTPN6. Nucleotide sequences of the ROS1 gene and mRNA are known for a number of species, including human (e.g., as annotated under NCBI Gene ID: 6098).

In some embodiments, the presence of a gene rearrangement of RET in a sample obtained from a tumor in a subject can indicate that the tumor is susceptible to treatment with a treatment selected from the group consisting of: a RET inhibitor; DP-2490, DP-3636, SU5416; BAY 43-9006, BAY 73-4506 (regorafenib), ZD6474, NVP-AST487, sorafenib, RPI-1, XL184, vandetanib, sunitinib, imatinib, pazopanib, axitinib, motesanib, gefitinib, and withaferin A (see, e.g., Samadi et al., Surgery 2010 148:1228-36; Cuccuru et al., JNCI 2004 13:1006-1014; Akeno-Stuart et al., Cancer Research 2007 67:6956; Grazma et al., J Clin Oncol 2010 28:15s 5559; Mologni et al., J Mol Endocrinol 2006 37:199-212; Calmomagno et al., Journal NCI 2006 98:326-334; Mologni, Curr Med Chem 2011 18:162-175; and the compounds disclosed in WO 06/034833; US Patent Publication 2011/0201598 and U.S. Pat. No. 8,067,434). All of the foregoing references are incorporated by reference herein in their entireties. A RET inhibitor can include any agent that reduces the expression and/or kinase activity of RET or a portion thereof, including, e.g., oligonucleotides, small molecules, and/or peptides that reduce the expression and/or activity of RET or a portion thereof. As used herein, "rearranged during transfection" or "RET" refers to a receptor tyrosine kinase of the cadherin superfamily which is involved in neural crest development and recognizes glial cell line-derived neurotrophic factor family signaling molecules. Nucleotide sequences of the RET gene and mRNA are known for a number of species, including human (e.g., as annotated under NCBI Gene ID: 5979).

In some embodiments, the known target sequence can comprise a gene selected from Table 2.

TABLE 2

| | | Known target sequences | | |
|---|---|---|---|---|
| GENE | TRANSCRIPT NCBI Reference Sequences (RefSeq) | EXONS | DIRECTION | TYPE |
| AKT3 | NM_005465 | 1, 2, 3 | 5' | Fusion |
| ALK | NM_004304 | 19, (intron19), 20, 21, 22 | 5' | Fusion |
| ARHGAP26 | NM_015071 | 2, 10, 11, 12 | 5' | Fusion |
| AXL | NM_021913 | 19, 20 | 3' | Fusion |
| BRAF | NM_004333 | 7, 8 | 3' | Fusion |
| BRAF | NM_004333 | 7, 8, 9, 10, 11, 12 | 5' | Fusion |
| BRAF | NM_004333 | 15 | 5' | Fusion |
| BRAF | NM_004333 | V600E | n/a | Mutation |
| BRD3 | NM_007371 | 9, 10, 11, 12 | 3' | Fusion |
| BRD4 | NM_014299 | 10, 11 | 3' | Fusion |
| EGFR | NM_005228 | 7, 9, 16, 20 | 5' | Fusion |
| EGFR | NM_005228 | 8 (2-7 exon skipping event) | n/a | Mutation |
| EGFR | NM_005228 | 24, 25 | 3' | Fusion |
| ERG | NM_004449 | 2, 3, 4, 5, 6, 7, 8, 9, 10, 11 | 5' | Fusion |
| ESR1 | NM_001122742 | 3, 4, 5, 6 | 3' | Fusion |
| ETV1 | NM_004956 | 3, 4, 5, 6, 7, 8, 9, 10, 11, 12, 13 | 5' | Fusion |

TABLE 2-continued

Known target sequences

| GENE | TRANSCRIPT NCBI Reference Sequences (RefSeq) | EXONS | DIRECTION | TYPE |
|---|---|---|---|---|
| ETV4 | NM_001986 | 2, 4, 5, 6, 7, 8, 9, 10 | 5' | Fusion |
| ETV5 | NM_004454 | 2, 3, 7, 8, 9 | 5' | Fusion |
| ETV6 | NM_001987 | 1, 2, 3, 4, 5, 6 | 3' | Fusion |
| ETV6 | NM_001987 | 2, 3, 5, 6, 7 | 5' | Fusion |
| EWSR1 | NM_005243 | 4, 5, 6, 7, 8, 9, 10, 11, 12, 13, 14 | 3' | Fusion |
| FGFR1 | NM_015850 | 2, 8, 9, 10, 17 | 5' | Fusion |
| FGFR2 | NM_000141 | 2, 8, 9, 10 | 5' | Fusion |
| FGFR2 | NM_000141 | 17 | 3' | Fusion |
| FGFR3 | NM_000142 | 17, Intron 17 | 3' | Fusion |
| FGFR3 | NM_000142 | 8, 9, 10 | 5' | Fusion |
| FGR | NM_005248 | 2 | 5' | Fusion |
| INSR | NM_000208 | 20, 21, 22 | 3' | Fusion |
| INSR | NM_000208 | 12, 13, 14, 15, 16, 17, 18, 19 | 5' | Fusion |
| MAML2 | NM_032427 | 2, 3 | 5' | Fusion |
| MAST1 | NM_014975 | 7, 8, 9, 18, 19, 20, 21 | 5' | Fusion |
| MAST2 | NM_015112 | 2, 3, 5, 6 | 5' | Fusion |
| MET | NM_000245 | 13 | 3' | Fusion |
| MET | NM_000245 | 13, 15 (exon 14 skipping event) | n/a | Mutation |
| MSMB | NM_002443 | 2, 3, 4 | 3' | Fusion |
| MUSK | NM_005592 | 7, 8, 9, 11, 12, 13, 14 | 5' | Fusion |
| MYB | NM_001130173 | 7, 8, 9, 11, 12, 13, 14, 15, 16 | 3' | Fusion |
| NOTCH1 | NM_017617 | 2, 4, 29, 30, 31 | 3' | Fusion |
| NOTCH1 | NM_017617 | 26, 27, 28, 29 (internal exon 3-27 deletion) | 5' | Fusion |
| NOTCH2 | NM_024408 | 5, 6, 7 | 3' | Fusion |
| NOTCH2 | NM_024408 | 26, 27, 28 | 5' | Fusion |
| NRG1 | NM_004495 | 1, 2, 3, 6 | 5' | Fusion |
| NTRK1 | NM_002529 | 8, 10, 11, 12, 13 | 5' | Fusion |
| NTRK2 | NM_006180 | 11, 12, 13, 14, 15, 16, 17 | 5' | Fusion |
| NTRK3 | NM_002530 | 13, 14, 15, 16 | 5' | Fusion |
| NTRK3 | NM_001007156 | 15 | 5' | Fusion |
| NUMBL | NM_004756 | 3 | 5' | Fusion |
| NUTM1 | NM_175741 | 3 | 5' | Fusion |
| PDGFRA | NM_006206 | 7 (exon 8 deletion) | n/a | Mutation |
| PDGFRA | NM_006206 | 10, 11, 12, 13, 14, | 5' | Fusion |
| PDGFRA | NM_006206 | T674I, D842V | n/a | Mutation |
| PDGFRB | NM_002609 | 8, 9, 10, 11, 12, 13, 14 | 5' | Fusion |
| PIK3CA | NM_006218 | 2 | 5' | Fusion |
| PKN1 | NM_002741 | 10, 11, 12, 13 | 5' | Fusion |
| PPARG | NM_015869 | 1, 2, 3 | 5' | Fusion |
| PRKCA | NM_002737 | 4, 5, 6 | 5' | Fusion |
| PRKCB | NM_002738 | 3 | 5' | Fusion |
| RAF1 | NM_002880 | 4, 5, 6, 7, 9 | 3' | Fusion |
| RAF1 | NM_002880 | 4, 5, 6, 7, 9, 10, 11, 12 | 5' | Fusion |
| RELA | NM_021975 | 3, 4 | 5' | Fusion |
| RET | NM_020630 | 8, 9, 10, 11, 12, 13 | 5' | Fusion |
| ROS1 | NM_002944 | 31, 32, 33, 34, 35, 36, 37 | 5' | Fusion |
| RSPO2 | NM_178565 | 1, 2 | 5' | Fusion |
| RSPO3 | NM_032784 | 2 | 5' | Fusion |
| TERT | NM_198253 | 2 | 5' | Fusion |
| TFE3 | NM_006521 | 2, 3, 4, 5, 6 | 3' | Fusion |
| TFE3 | NM_006521 | 2, 3, 4, 5, 6, 7, 8 | 5' | Fusion |
| TFEB | NM_007162 | 1, 2 | 5' | Fusion |
| THADA | NM_022065 | 28 | 3' | Fusion |
| TMPRSS2 | NM_005656 | 1, 2, 3, 4, 5, 6 | 3' | Fusion |
| TMPRSS2 | NM_001135099 | 1 | 3' | Fusion |

Further non-limiting examples of applications of methods described herein include detection of hematological malignancy markers and panels thereof (e.g., including those to detect genomic rearrangements in lymphomas and leukemias), detection of sarcoma-related genomic rearrangements and panels thereof; and detection of IGH/TCR gene rearrangements and panels thereof for lymphoma testing.

In some embodiments, methods described herein relate to treating a subject having or diagnosed as having, e.g., cancer with a treatment for cancer. Subjects having cancer can be identified by a physician using current methods of diagnosing cancer. For example, symptoms and/or complications of lung cancer which characterize these conditions and aid in diagnosis are well known in the art and include but are not limited to, weak breathing, swollen lymph nodes above the collarbone, abnormal sounds in the lungs, dullness when the chest is tapped, and chest pain. Tests that may aid in a diagnosis of, e.g., lung cancer include, but are not limited to, x-rays, blood tests for high levels of certain substances (e.g., calcium), CT scans, and tumor biopsy. A family history of lung cancer, or exposure to risk factors for lung cancer (e.g., smoking or exposure to smoke and/or air pollution) can also aid in determining if a subject is likely to have lung cancer or in making a diagnosis of lung cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non-Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chronic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS1arcoma, and osteosarcoma; pancreatic cancer; skin cancer including melanoma, stromal cells, germ cells and mesenchymal cells; pROS ltate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors. In some embodiments, the cancer can be lung cancer.

Multiplex Methods

Methods described herein can be employed in a multiplex format. In embodiments of methods described herein, multiplex applications can include determining the nucleotide sequence contiguous to one or more known target nucleotide sequences. As used herein, "multiplex amplification" refers to a process that involves simultaneous amplification of more than one target nucleic acid in one or more reaction vessels. In some embodiments, methods involve subsequent determination of the sequence of the multiplex amplification products using one or more sets of primers. Multiplex can refer to the detection of between about 2-1,000 different target sequences in a single reaction. In some embodiments, however, multiplex can refer to the detection of between about 1,000-10,000 different target sequences in a single reaction. In some embodiments, multiplex can refer to the detection of between about 10,000-100,000 different target sequences in a single reaction. As used herein, multiplex refers to the detection of any range between 2-1,000, e.g., between 5-500, 25-1,000, or 10-100 different target sequences in a single reaction, etc. The term "multiplex" as applied to PCR implies that there are primers specific for at least two different target sequences in the same PCR reaction.

In some embodiments, target nucleic acids in a sample, or separate portions of a sample, can be amplified with a plurality of primers (e.g., a plurality of first and second target-specific primers). In some embodiments, the plurality of primers (e.g., a plurality of first and second target-specific primers) can be present in a single reaction mixture, e.g., multiple amplification products can be produced in the same reaction mixture. In some embodiments, the plurality of primers (e.g., a plurality of sets of first and second target-specific primers) can specifically anneal to known target sequences comprised by separate genes. In some embodiments, at least two sets of primers (e.g., at least two sets of first and second target-specific primers) can specifically anneal to different portions of a known target sequence. In some embodiments, at least two sets of primers (e.g., at least two sets of first and second target-specific primers) can specifically anneal to different portions of a known target sequence comprised by a single gene. In some embodiments, at least two sets of primers (e.g., at least two sets of first and second target-specific primers) can specifically anneal to different exons of a gene comprising a known target sequence. In some embodiments, the plurality of primers (e.g., first target-specific primers) can comprise identical 5' tag sequence portions.

In embodiments of methods described herein, multiplex applications can include determining the nucleotide sequence contiguous to one or more known target nucleotide sequences in multiple samples in one sequencing reaction or sequencing run. In some embodiments, multiple samples can be of different origins, e.g., from different tissues and/or different subjects. In such embodiments, primers (e.g., tailed random primers) can further comprise a barcode portion. In some embodiments, a primer (e.g., a tailed random primer) with a unique barcode portion can be added to each sample and ligated to the nucleic acids therein; the samples can subsequently be pooled. In such embodiments, each resulting sequencing read of an amplification product will comprise a barcode that identifies the sample containing the template nucleic acid from which the amplification product is derived.

EXAMPLES

The following examples are intended to illustrate certain embodiments described herein, including certain aspects of the present invention, but do not exemplify the full scope of the invention.

Example 1

Nucleic Acid Sample Preparation

An example of a protocol that illustrates a method of preparing a nucleic acid sample for analysis is shown in FIG. 1.

A biotinylated receptor-specific primer is annealed with sample RNA. A thermal cycler is heated to 65° C. and purified total nucleic acid or RNA (20-250 ng) is combined with nuclease-free water while on ice before combining with receptor-specific primer. The sample is then transferred to the thermal cycler and incubated with a heated lid ($\geq 100°$ C.) at 65° C. for 5 minutes and then held at 4° C. Once finished, the sample is placed on ice for at least 2 minutes.

Following annealing, the first strand cDNA is synthesized by extension of the receptor-specific primer by the action of a reverse transcriptase enzyme to generate a DNA/RNA hybrid. The sample is incubated in a thermal cycler with a heated lid (≥100° C.) at 50° C. for 30 minutes, followed by 20 minutes at 80° C., and then held at 4° C.

The RNA strand of the resulting DNA/RNA hybrid is partially degraded via the action of a ribonuclease, which leaves behind RNA fragments annealed to the first strand that serve as primers for a second strand synthesis reaction. The second strand cDNA is synthesized following incubation with DNA PolI in a thermal cycler with a heated lid (≥100° C.) at 16° C. for 60 minutes, followed by 20 minutes at 75° C., and then held at 4° C.

The double-stranded cDNA sample is subjected to end repair to blunt end the cDNA and phosphorylate the 5' ends. In this step, an excess of T4 DNA Polymerase and T4 Polynucleotide Kinase is added to the sample along with sufficient dNTPs and allowed to incubate for 30 minutes at 25° C. in a thermal cycler (without a heated lid). The DNA is subjected to a cleanup step using AMPure® XP beads (2.5×). The beads are completely re-suspended by vortexing and added to each reaction with mixing to ensure a homogenous mixture. The reaction is then incubated for 5 minutes at room temperature (20 to 25° C.). The tubes are then spun down and placed on a magnet for 4 minutes to ensure the beads are fully pelleted against the tube wall. The supernatant is discarded without disturbing the bead pellet and more magnification is used as necessary to re-pellet the beads. The beads are washed with 70% ethanol for 30 seconds while still on the magnet before the supernatant is discarded. The washing is repeated twice. After the final wash, the visible supernatant residue is completely removed and the beads are dried for 5 minutes at room temperature with open lids. The beads should not be over-dried as this significantly decreases the overall yield of nucleic acid. The DNA is eluted by re-suspending the beads in 10 mM Tris-HCl pH 8.0. The tubes are then placed back on the magnet for 2 minutes.

In a first ligation step, the purified DNA is then subjected to a dA-tailing reaction that incorporates dAMPs onto the 3' ends of the DNA strands during incubation in a thermal cycler with a heated lid (≥100° C.) for 15 minutes at 37° C. and then held at 4° C. The reaction is then spun down and placed on ice.

Following the A-tailing, the samples are cleaned using AMPure® XP beads (2.5×) following the same procedure described above. The DNA is eluted using nuclease-free water.

In a second ligation step, unique nucleotide sequences or molecular barcodes (MBCs) are ligated to the DNA via the action of DNA ligase following incubation in a thermal cycler (without a heated lid) for 15 minutes at 25° C. and then held at 4° C. The samples are then purified using streptavidin-coated beads. The samples are placed on a magnet for 1 minute or until the beads are pelleted. The supernatant is removed using a pipette without disturbing the bead pellet. The beads are then re-suspended in ligation cleanup buffer (1 M NaCl, 1 mM EDTA, 0.1% Tween, 10 mM Tris pH 8). The ligated DNA product (50 μL) is mixed with ligation cleanup beads (50 μL for a total of 100 μL) and the reaction is incubated at room temperature for 5 minutes, followed by mixing, and another 5 minutes of incubation. The samples are spun down and placed on a magnet for 1 minute to ensure the beads are fully pelleted against the tube wall. The supernatant is discarded without disturbing the beads and the beads are washed with ligation buffer and placed on a magnet for 1 minute. Once the slurry has cleared, the supernatant is discarded. The beads are then washed twice with buffer and then once with nuclease-free water. The MBC adapter-bound beads are then transferred to a separate mixture of components for a first PCR step.

A first round of PCR is performed using a first gene-specific primer and a first adapter primer. The reaction is kept on ice before performing the first PCR in a thermal cycler with a heated lid (>100° C.) using the program described in Table 3. Once the reaction has reached 4° C., the reactions are briefly spun down and placed on ice.

TABLE 3

PCR Conditions for the First PCR Reaction.

| Step | Temperature (° C.) | Time (min) | Cycles |
|---|---|---|---|
| 1 | 95 | 3 min | 1 |
| 2 | 95 | 30 sec | 24 |
| 3 | 65 | 3 min (100% ramp rate) | |
| 4 | 72 | 3 min | 1 |
| 5 | 4 | Hold | 1 |

The PCR reaction is then cleaned using AMPure® XP beads (1.2×) and incubated for 5 minutes at room temperature (20 to 25° C.). The tubes are then briefly spun down and placed on a magnet for 4 minutes to ensure that the beads are fully pelleted against the tube wall. The supernatant is discarded without disturbing the bead pellet. The tubes are then washed for 30 seconds with 70% ethanol while remaining on the magnet. The washing is repeated twice. After the final wash, the supernatant is removed with a pipette and the tubes are dried for 3 minutes at room temperature. The beads should not be over-dried as this significantly decreases the overall yield of nucleic acid. The DNA is eluted by re-suspending the beads in 10 mM Tris-HCl pH 8.0. The tubes are then placed on the magnet for 2 minutes before the supernatant is transferred to a separate mixture of components for a second PCR step.

A second round of PCR is performed using a second gene-specific primer and a second adapter primer. The second PCR step incorporates a P7-tail, which is incorporated as a 5' tailed region of the second gene-specific primer, as shown in FIG. 1. The sequences for Index 1 (P7) tags are shown in Table 4.

TABLE 4

Index 1 (P7) Sequence Table.

| Sample Number | IIlumina Index 1 P7/i7 Sequence |
|---|---|
| 1 | TAAGGCGA |
| 2 | CGTACTAG |
| 3 | AGGCAGAA |
| 4 | TCCTGAGC |
| 5 | GGACTCCT |
| 6 | TAGGCATG |
| 7 | CTCTCTAC |
| 8 | CAGAGAGG |

The purified library DNA from the first PCR is mixed with the second gene-specific primer and second adapter primer and PCR components, and the second PCR is performed in the thermal cycler with a heated lid (≥100° C.) using the program described in Table 5. Once the reaction has reached 4° C., the reactions are briefly spun down and placed on ice.

TABLE 5

PCR Conditions for the Second PCR Reaction.

| Step | Temperature (° C.) | Time | Cycles |
|------|--------------------|------|--------|
| 1 | 95 | 3 min | 1 |
| 2 | 95 | 30 sec | 6 |
| 3 | 65 | 3 min (100% ramp rate) | |
| 4 | 72 | 3 min | 1 |
| 5 | 4 | Hold | 1 |

The PCR reaction is then cleaned using AMPure® XP beads (1.2×) following the same procedure outlined in the First PCR Reaction. The DNA is eluted by re-suspending the beads in 10 mM Tris-HCl pH 8.0 and incubating on a magnet for 2 minutes. The library-tagged DNA is then transferred to a new PCR tube for storage, quantification, or normalization and sequencing.

Example 2

Diversity and Reproducibility

Figure 4:
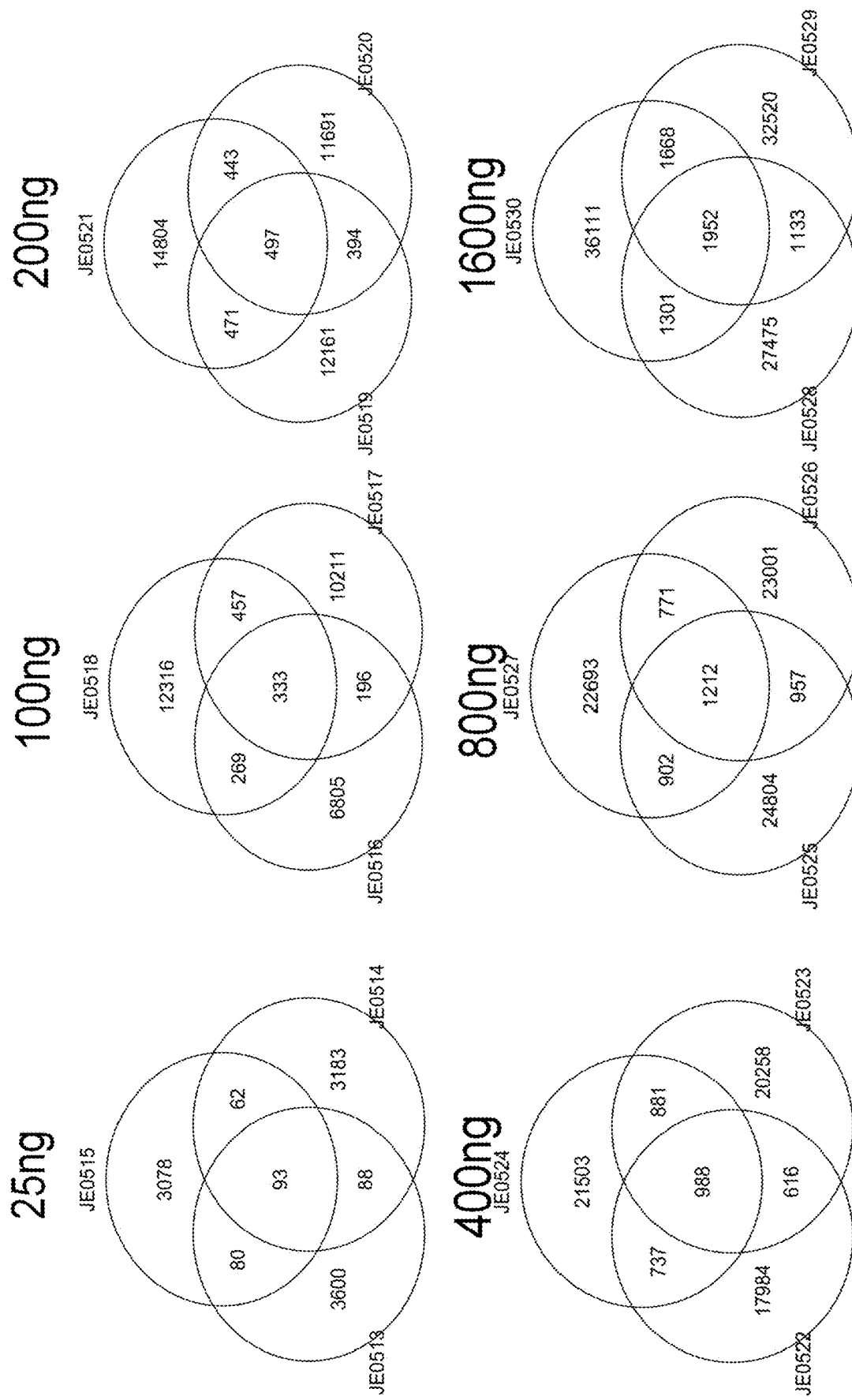
FIG. 4 is an illustration showing clonotype overlap between replicates in relation to input amount. The intersection of all samples yields sixty six overlapping clonotypes.
Figure 5:
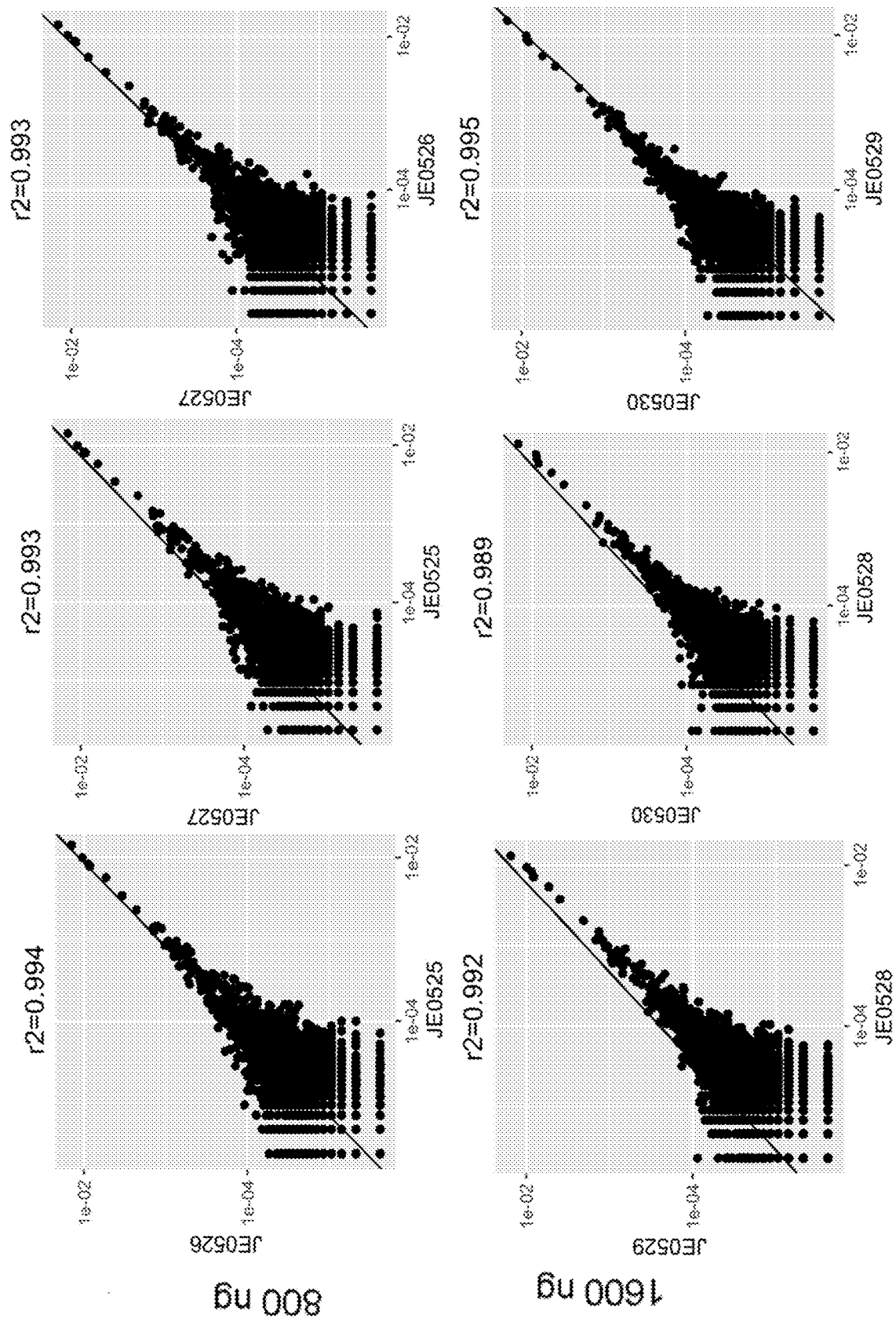
FIG. 5 is a chart illustrating that pairwise analysis of replicate samples demonstrates the highly reproducible nature of the assay.
Figure 6A:
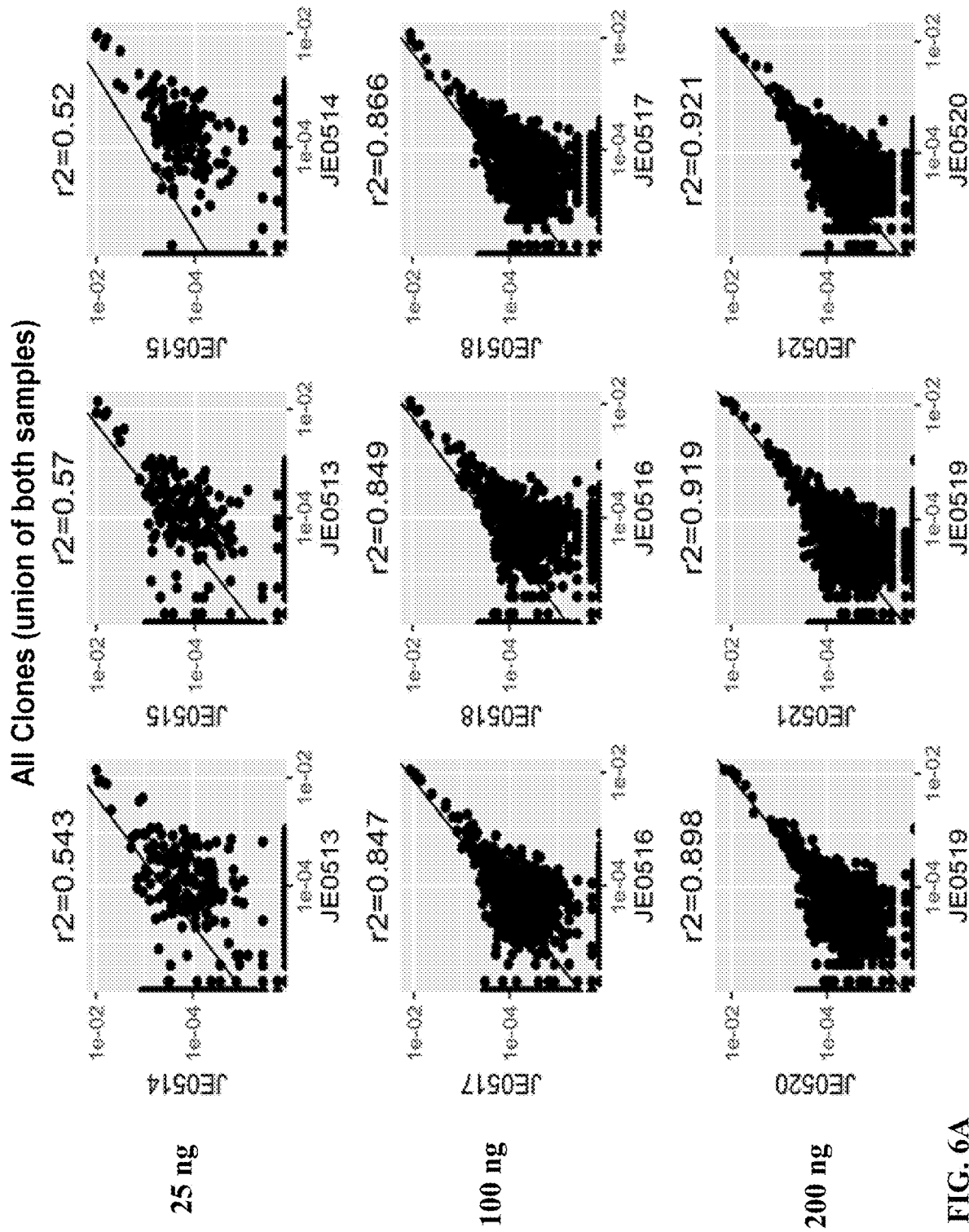
FIGS. 6A and 6B depict a comparison between all clones (FIG. 6A) and overlapping clones (FIG. 6B).
Figure 6A:
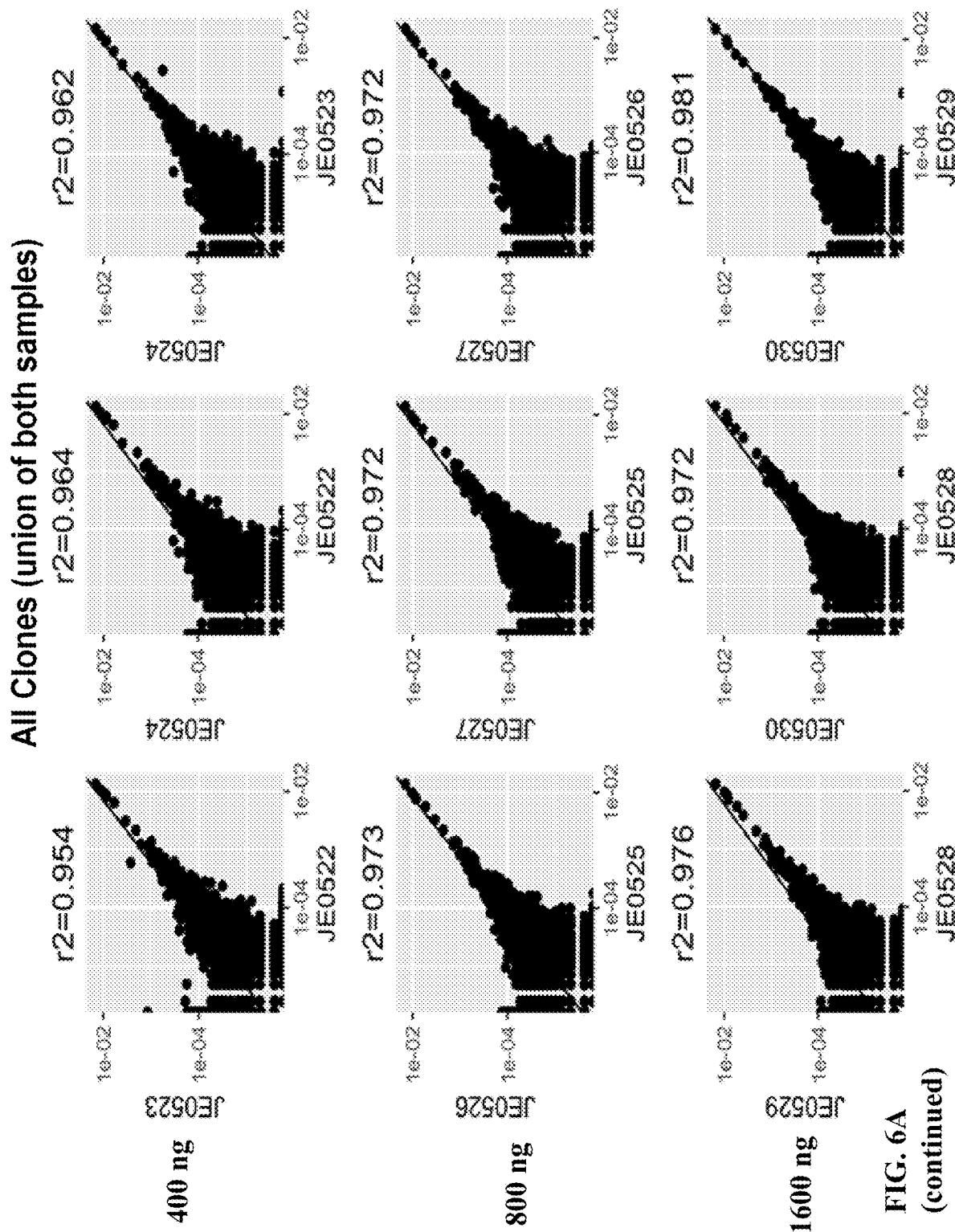
Figure 6B:
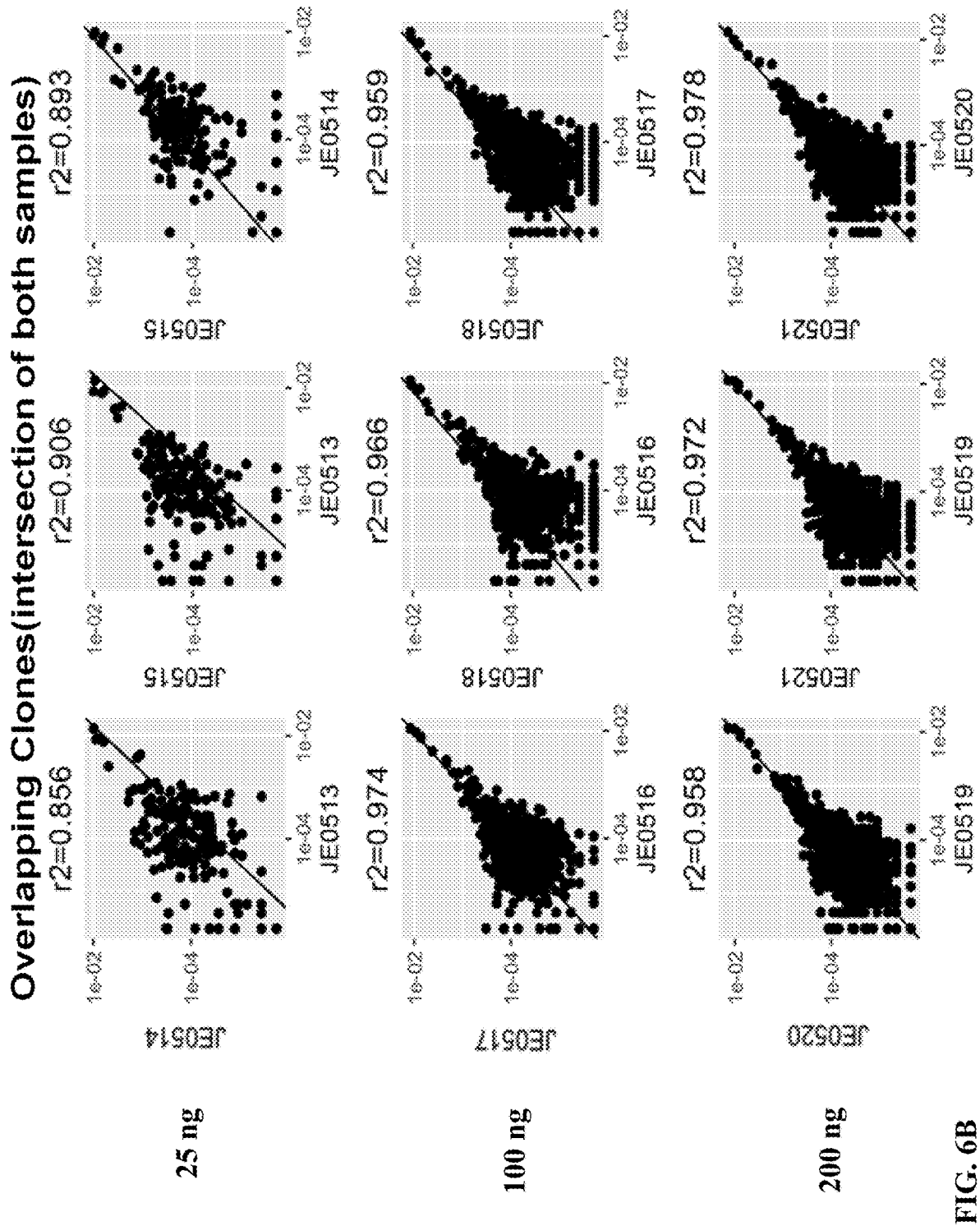
Figure 6B:
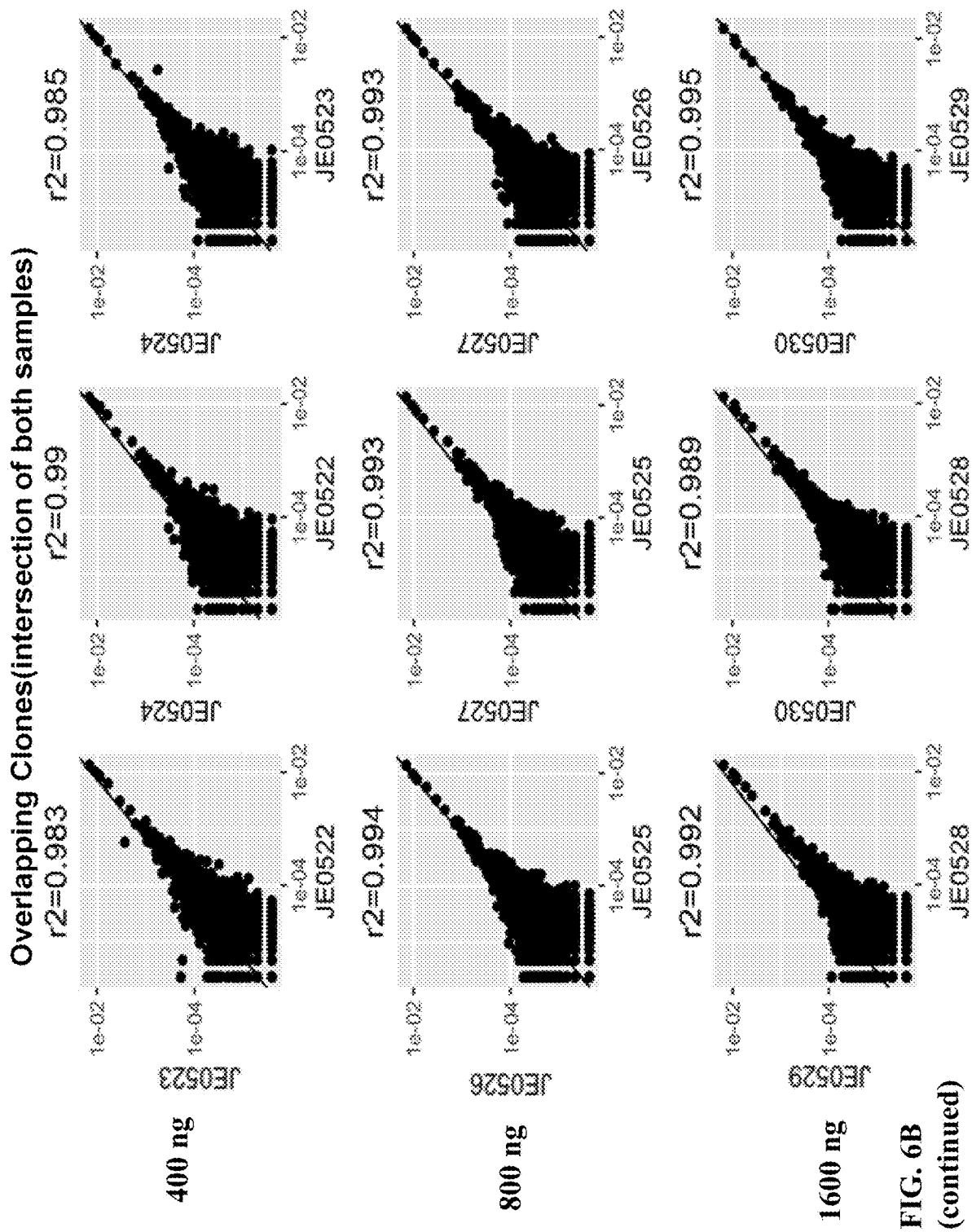
Figure 7:
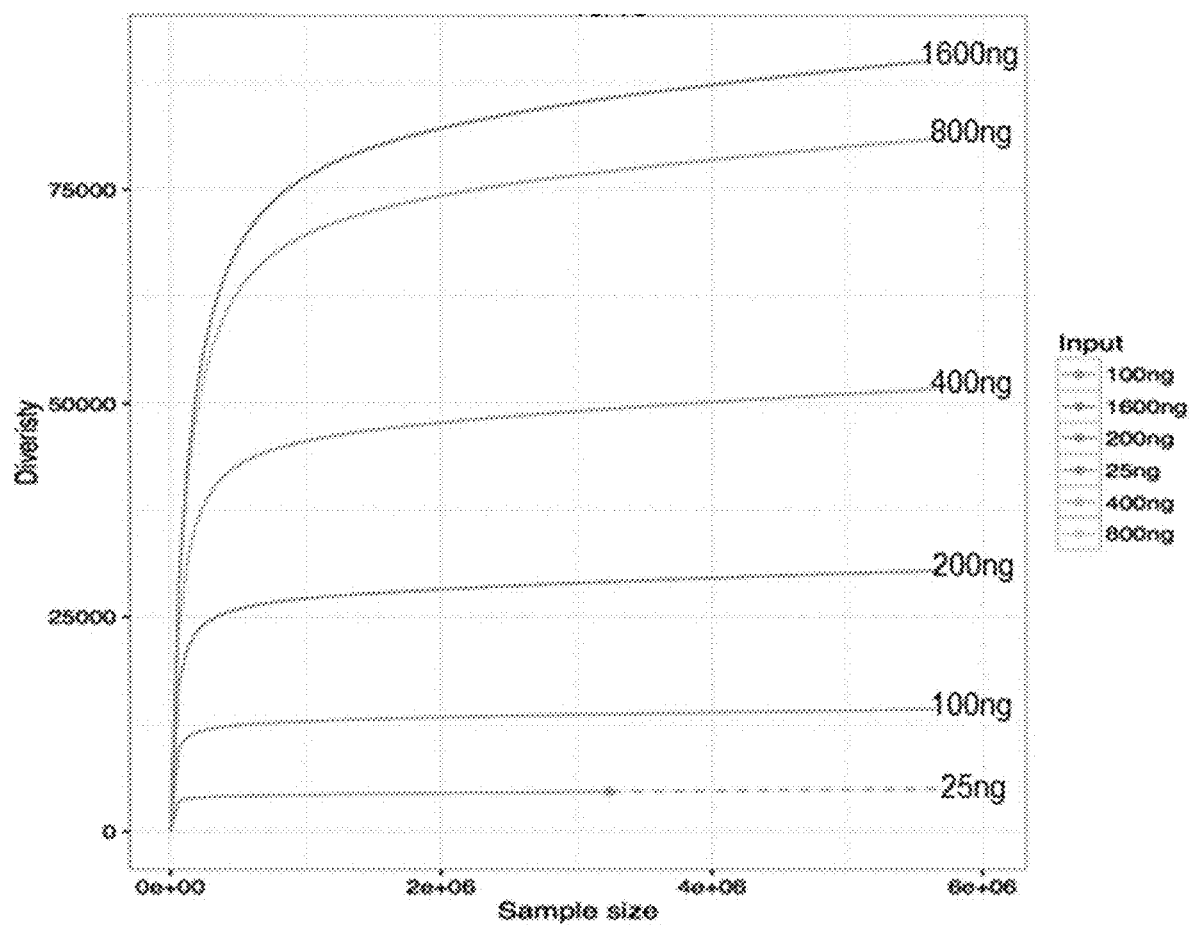
FIG. 7 illustrates that input quantity drives complexity and diversity of observation, with diversity in relation to sample size depicted at top and a chart depicting Shannon diversity index shown at bottom.
Figure 7:
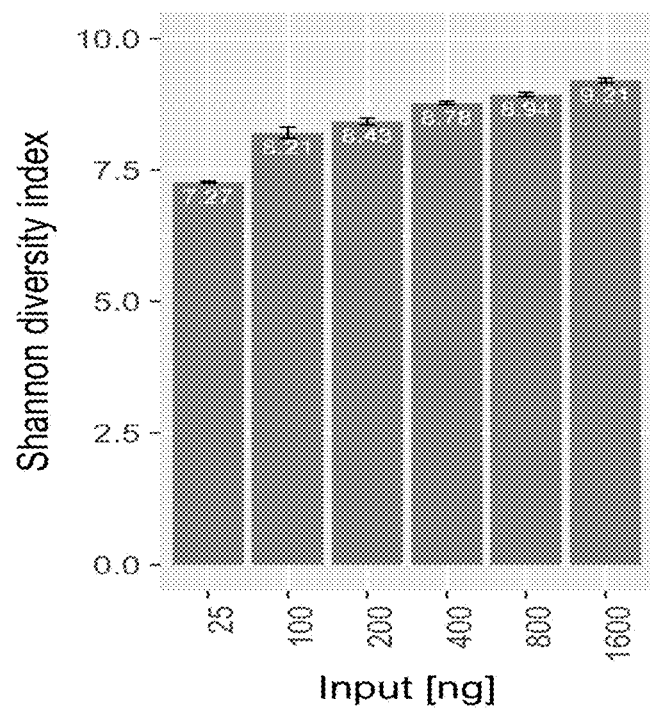

Sequencing information was obtained from samples of varied input amounts (25, 100, 200, 400, 800, and 1600 ng) across repeat experiments using the methods described above. As shown in FIG. 4, clonotype overlap between replicate experiments increases with input amount. A pairwise analysis of replicate samples was further performed using data from 256,000 reads. The results, which demonstrated the highly reproducible nature of the assay, are shown for 800 and 1600 ng input samples in FIG. 5. FIGS. 6A and 6B depict the full side-by-side analysis of all clones (FIG. 6A) versus overlapping clones (FIG. 6B). FIG. 7 shows a plot of diversity versus sample size (top) and a chart of Shannon diversity index by input size (bottom), which show that input quantity drives complexity and diversity of observation.

Figure 8:
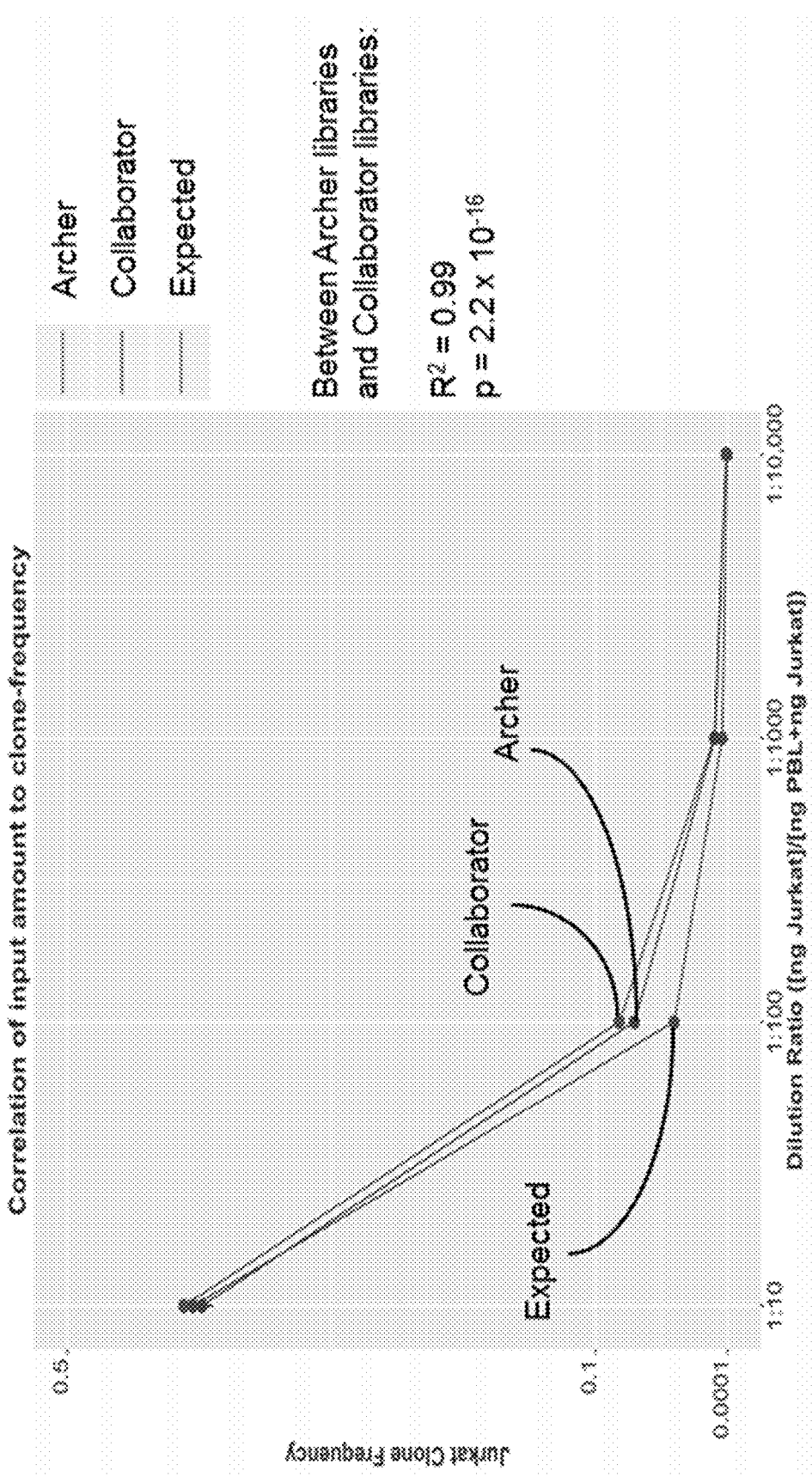
FIG. 8 is a graph demonstrating highly reproducible and quantitative clone tracking.
Figure 9:
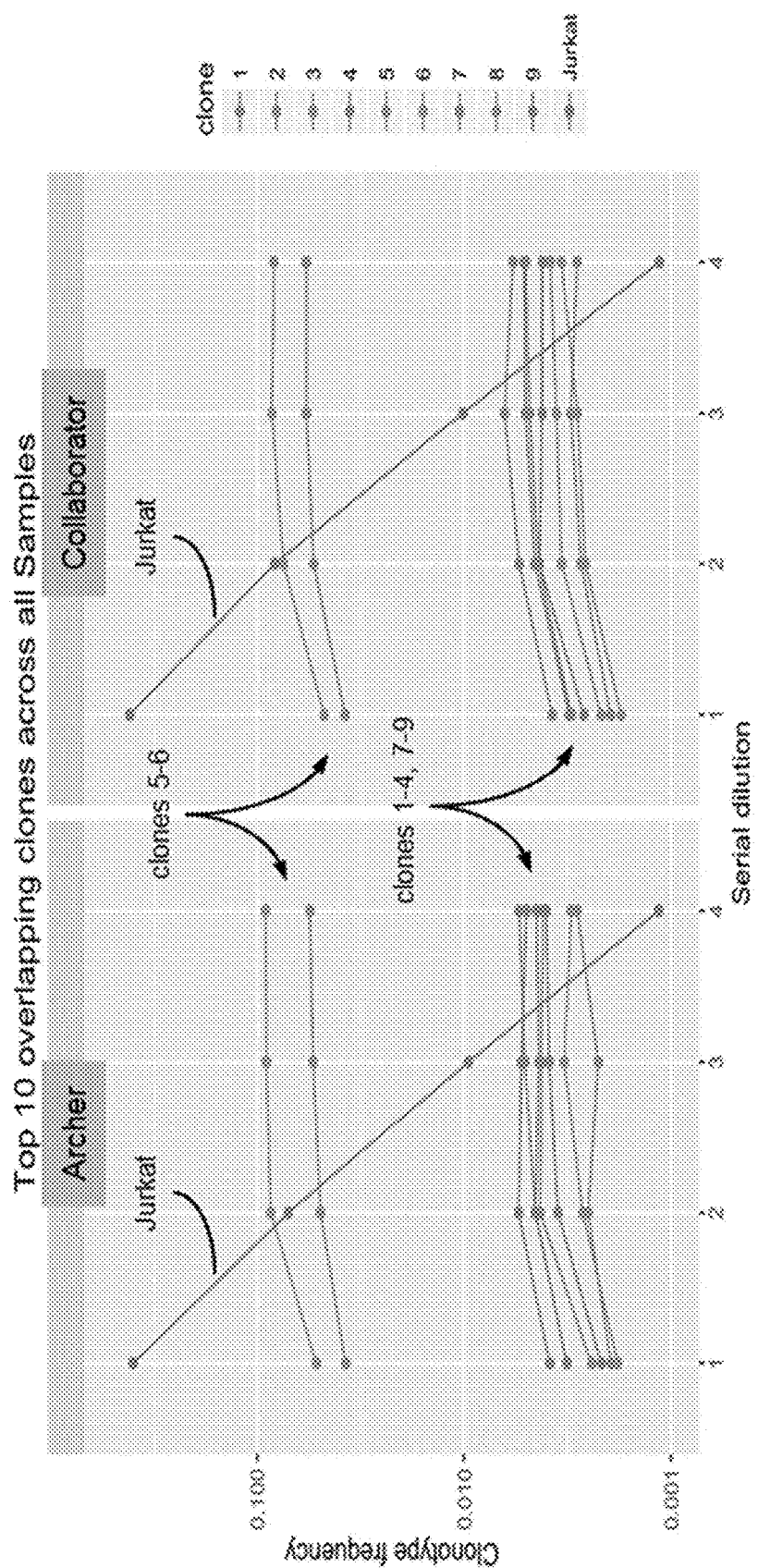
FIG. 9 illustrates that clonal tracking across dilutions is highly reproducible between independent laboratories.
Figure 10:
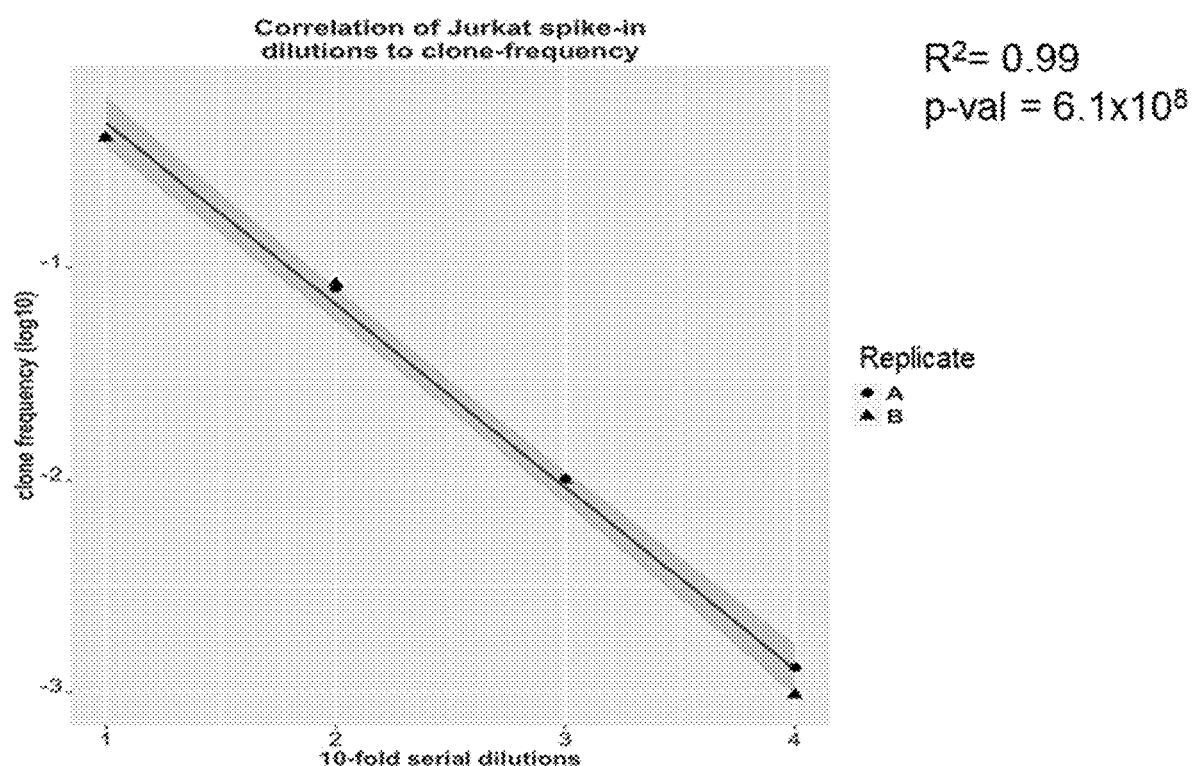
FIG. 10 is a graph depicting intra-laboratory reproducibility using a Jurkat sample dilution series.

As shown in FIGS. 8-10, a Jurkat dilution series was used to test intra- and inter-lab reproducibility. The Jurkat cell line expressing the TCRα:β receptor was spiked into healthy donor peripheral blood lymphocytes (PBL) RNA to determine limits of T cell receptor beta chain (TRB) detection and to assess inter-lab assay variation. A serial dilution of Jurkat total RNA into PBL RNA was performed ranging from 1:10 dilution to 1:10,000 [ng Jurkat/(ng Jurkat+ng PBL)] in duplicate.

Figure 11:
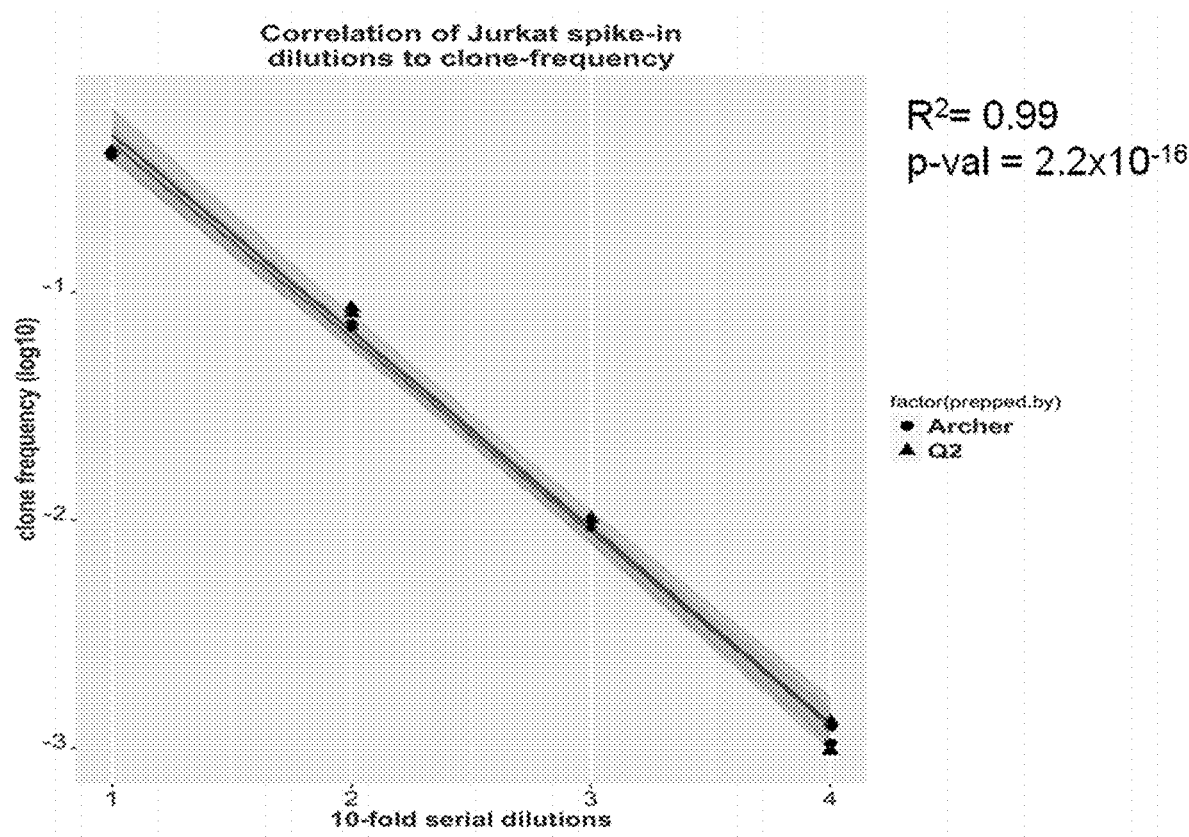
FIG. 11 is a graph depicting inter-laboratory reproducibility using the Jurkat sample dilution series.

The serial dilution was divided into two aliquots per dilution, and the libraries were prepared and sequenced. The results in FIG. 11 show a strong correlation between both labs.

All libraries were normalized to 600,000, deduplicated and error-corrected. The expected frequencies were determined by multiplying the clonotype frequencies of the 1:10 dilutions by 10 and dividing the resulting number by the respective dilution factors (e.g., factor=0.5 (1:10 dilution)× 10=5.5/dilution factor=experimental frequency for given dilution factor).

Example 3

Primers

Figure 12:
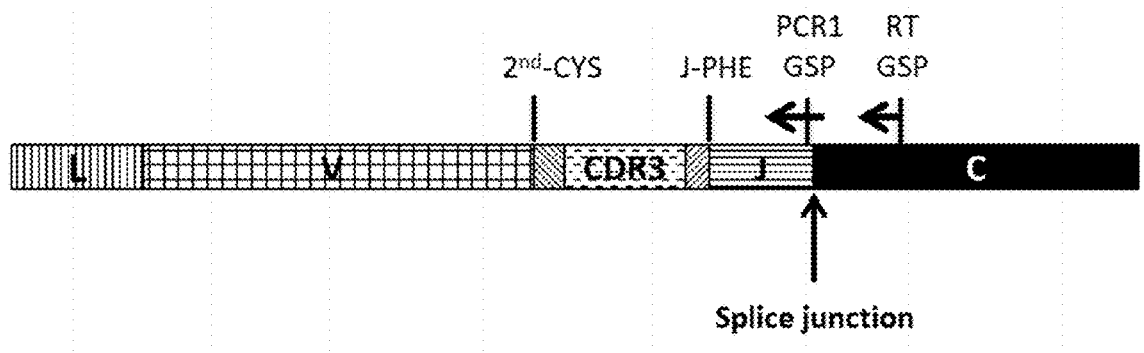
FIG. 12 is a schematic, not shown to scale, that generally depicts T cell receptor primer locations.

FIG. 12 depicts an FFPE-optimized strategy for analysis of TCR (β/γ) repertoire. As shown, the reverse transcriptase (RT) primer binding site corresponds to a 5' region of the constant domain exon. The first PCR gene-specific primers (GSPs) are designed to bind to a region that corresponds either to a 3' region of the J-segment or a region spanning the J-segment:C exon intersection. The average distance from the 5' end of the RT primer to the 5' end of CDR3 is less than 100 base pairs. Panels of primers were designed for immune repertoire sequencing of TCR (β/γ) and TCR (α/δ), listed in Table 6 and Table 7, respectively.

TABLE 6

T Cell Receptor (β/γ) Primer Panel

Reverse Transcriptase Primers

| Primer Name | Sequence (sequence with modified nucleotides shown beneath each) |
|-------------|------------------------------------------------------------------|
| TRAC_RT_19_60.7_BIOTIN_redesign | CACTGGATTTAGAGTCTCTCAGC (SEQ ID NO: 1)<br>/52-Bio/C*ACTGGATTTAGAGTCTCTCAGC (SEQ ID NO: 2) |
| TRBC1_RT_2_59.8_BIOTIN | GAACACCTTGTTCAGGTCCT (SEQ ID NO: 3)<br>/52-Bio/G*AACACCTTGTTCAGGTCCT (SEQ ID NO: 4) |
| TRBC2_RT_1_59.8_BIOTIN | GAACACGTTTTTCAGGTCCTC (SEQ ID NO: 5)<br>/52-Bio/G*AACACGTTTTTCAGGTCCTC (SEQ ID NO: 6) |
| TRDC_RT_37_59_BIOTIN | TCTTATATCCTTGGGGTAGAATTCC (SEQ ID NO: 7)<br>/52-Bio/T*CTTATATCCTTGGGGTAGAATTCC (SEQ ID NO: 8) |
| TRGC_RT_24_univ_60.6_BIOTIN | GGGAAACATCTGCATCAAGTTG (SEQ ID NO: 9)<br>/52-Bio/G*GGAAACATCTGCATCAAGTTG (SEQ ID NO: 10) |

First PCR Gene-Specific Primers

| Primer Name | Sequence (sequence with tail shown beneath each) |
|-------------|--------------------------------------------------|
| TRBJ1-1*01_12_69.7 | CAGGTCCTCTACAACTGTGAGTCTGG (SEQ ID NO: 11)<br>AGACGTGTGCTCTTCCGATCTCAGGTCCTCTACAACTGTGAGTCTGG (SEQ ID NO: 12) |
| TRBJ1-2*01_3_70.1 | GGTCCTCTACAACGGTTAACCTGGTC (SEQ ID NO: 13)<br>AGACGTGTGCTCTTCCGATCTGGTCCTCTACAACGGTTAACCTGGTC (SEQ ID NO: 14) |
| TRBJ1-3*01_10_70.1 | GGTCCTCTACAACAGTGAGCCAACTT (SEQ ID NO: 15)<br>AGACGTGTGCTCTTCCGATCTGGTCCTCTACAACAGTGAGCCAACTT (SEQ ID NO: 16) |

TABLE 6-continued

T Cell Receptor (β/γ) Primer Panel

| | |
|---|---|
| TRBJ1-4*01_11_70.1 | GGTCCTCCAAGACAGAGAGCTGG (SEQ ID NO: 17)<br>AGACGTGTGCTCTTCCGATCTGGTCCTCCAAGACAGAGAGCTGG (SEQ ID NO: 18) |
| TRBJ1-5*01_9_70.4 | GGTCCTCTAGGATGGAGAGTCGAGTC (SEQ ID NO: 19)<br>AGACGTGTGCTCTTCCGATCTGGTCCTCTAGGATGGAGAGTCGAGTC (SEQ ID NO: 20) |
| TRBJ1-6_7_70.5 | GGTCCTCTGTCACAGTGAGCCTG (SEQ ID NO: 21)<br>AGACGTGTGCTCTTCCGATCTGGTCCTCTGTCACAGTGAGCCTG (SEQ ID NO: 22) |
| TRBJ2-1*01_1_70.1 | TCTAGCACGGTGAGCCGTGT (SEQ ID NO: 23)<br>AGACGTGTGCTCTTCCGATCTTCTAGCACGGTGAGCCGTGT (SEQ ID NO: 24) |
| TRBJ2-2*01_6_70.0 | CAGTACGGTCAGCCTAGAGCCTTC (SEQ ID NO: 25)<br>AGACGTGTGCTCTTCCGATCTCAGTACGGTCAGCCTAGAGCCTTC (SEQ ID NO: 26) |
| TRBJ2-3*01_2_70.0 | TTCAGGTCCTCGAGCACTGTCAG (SEQ ID NO: 27)<br>AGACGTGTGCTCTTCCGATCTTTCAGGTCCTCGAGCACTGTCAG (SEQ ID NO: 28) |
| TRBJ2-4*01_2_69.5 | TTCAGGTCCTCCAGCACTGAGAG (SEQ ID NO: 29)<br>AGACGTGTGCTCTTCCGATCTTTCAGGTCCTCCAGCACTGAGAG (SEQ ID NO: 30) |
| TRBJ2-5*01_1_69.9 | CAGGTCCTCGAGCACCAGGA (SEQ ID NO: 31)<br>AGACGTGTGCTCTTCCGATCTCAGGTCCTCGAGCACCAGGA (SEQ ID NO: 32) |
| TRBJ2-6*01_1_69.5 | CAGCACGGTCAGCCTGCT (SEQ ID NO: 33)<br>AGACGTGTGCTCTTCCGATCTCAGCACGGTCAGCCTGCT (SEQ ID NO: 34) |
| TRBJ2-7*01_2_69.7 | TTCAGGTCCTCTGTGACCGTGAG (SEQ ID NO: 35)<br>AGACGTGTGCTCTTCCGATCTTTCAGGTCCTCTGTGACCGTGAG (SEQ ID NO: 36) |
| TRGJ1_2_C_Ex1_20_69.5 | ACATCTGCATCAAGTTGTTTATCTGTGACAAC (SEQ ID NO: 37)<br>AGACGTGTGCTCTTCCGATCTACATCTGCATCAAGTTGTTTATCTGTGACAC (SEQ ID NO: 38) |
| TRGJP*01_C_Ex1_1_69.6 | TGTTTATCTGTAATGATAAGCTTTGTTCCGGGA (SEQ ID NO: 39)<br>AGACGTGTGCTCTTCCGATCTTGTTTATCTGTAATGATAAGCTTTGTTCCGGGA (SEQ ID NO: 40) |
| TRGJP1*1_C_Ex1_8_69.8 | TCAGGTGAAGTTACTATGAGCTTAGTCCCT (SEQ ID NO: 41)<br>AGACGTGTGCTCTTCCGATCTTCAGGTGAAGTTACTATGAGCTTAGTCCCT (SEQ ID NO: 42) |
| TRGJP2*01_C_Ex1_5_69.3 | GCGAAGTTACTATGAGCCTAGTCCCTT (SEQ ID NO: 43)<br>AGACGTGTGCTCTTCCGATCTGCGAAGTTACTATGAGCCTAGTCCCTT (SEQ ID NO: 44) |

TABLE 7

T Cell Receptor (α/δ) Primer Panel

Reverse Transcriptase Primers

| Primer Name | Sequence (sequence with modified nucleotides shown beneath each) |
|---|---|
| TRAC_RT_1_60.7_BIOTIN_redesign | CACTGGATTTAGAGTCTCTCAGC (SEQ ID NO: 1)<br>/52-Bio/C*ACTGGATTTAGAGTCTCTCAGC (SEQ ID NO: 2) |
| TRBC1_RT_2_59.8_BIOTIN | GAACACCTTGTTCAGGTCCT (SEQ ID NO: 3)<br>/52-Bio/G*AACACCTTGTTCAGGTCCT (SEQ ID NO: 4) |
| TRBC2_RT_1_59.8_BIOTIN | GAACACGTTTTTCAGGTCCTC (SEQ ID NO: 5)<br>/52-Bio/G*AACACGTTTTTCAGGTCCTC (SEQ ID NO: 6) |
| TRBC2_RT_37_59_BIOTIN | TCTTATATCCTTGGGGTAGAATTCC (SEQ ID NO: 7)<br>/52-Bio/T*CTTATATCCTTGGGGTAGAATTCC (SEQ ID NO: 8) |
| TRGC_RT_24_univ_60.6_BIOTIN | GGGAAACATCTGCATCAAGTTG (SEQ ID NO: 9)<br>/52-Bio/G*GGAAACATCTGCATCAAGTTG (SEQ ID NO: 10) |

First PCR Gene-Specific Primers

| Primer Name | Sequence (sequence with tail shown beneath each) |
|---|---|
| TRAC_PCR_9_69 | TCTCTCAGCTGGTACACGGCA (SEQ ID NO: 45)<br>AGACGTGTGCTCTTCCGATCTTCTCTCAGCTGGTACACGGCA (SEQ ID NO: 46) |
| TRDC_PCR_21_69 | TCACCAGACAAGCGACATTTGTTCC (SEQ ID NO: 47)<br>AGACGTGTGCTCTTCCGATCTTCACCAGACAAGCGACATTTGTTCC (SEQ ID NO: 48) |

Figure 13:
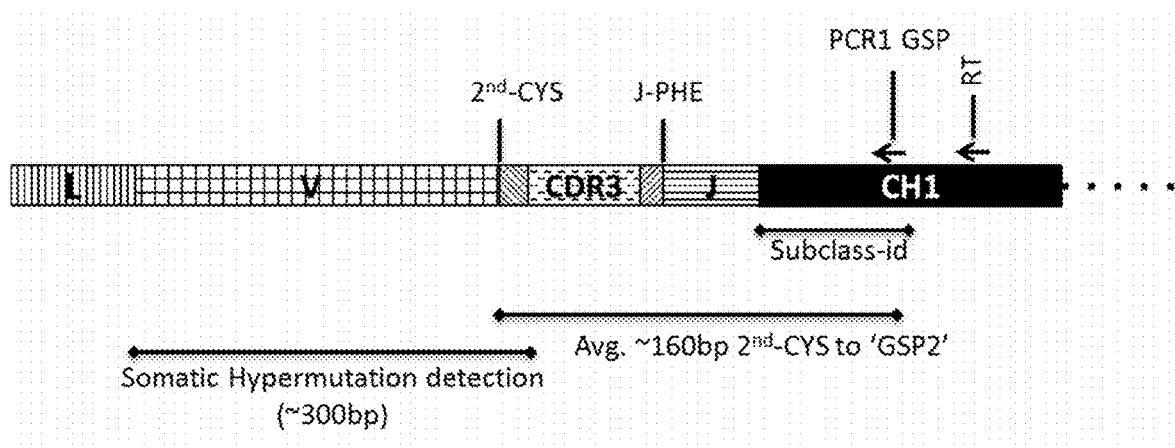
FIG. 13 is a schematic, not drawn to scale, that generally depicts immunoglobulin heavy chain (IgH) primer locations.

The BCR IgH primer panel has some additional requirements besides clonotype (CDR3) identification, compared to the TCR panels, since the IgH panel determines the isotype (A, D, E, G, M) and select subclasses. It also determines if the clone has undergone somatic hyper-mutation (V-segment analysis). The IgH primer locations are shown in FIG. 13. The RT primer and first PCR gene-specific primer bind to regions corresponding to the CH1 exon of the respective isotype constant region to distinguish select isotype subclasses. Panels of primers were designed for immune repertoire sequencing of BCR (IgH) and BCR (IgK/IgL), listed in Table 8 and Table 9, respectively

TABLE 8

B Cell Receptor (IgH) Primer Panel

Reverse Transcriptase Primers

| Primer Name | Sequence (sequence with modified nucleotides shown beneath each) |
|---|---|
| IGHA_RT_4_59_BIOTIN | GGCTCCTGGGGGAAGA (SEQ ID NO: 49)<br>/52-Bio/G*GCTCCTGGGGGAAGA (SEQ ID NO: 50) |
| IGHD_RT_40_59_BIOTIN | GTACCCAGTTATCAAGCATGC (SEQ ID NO: 51)<br>/52-Bio/G*TACCCAGTTATCAAGCATGC (SEQ ID NO: 52) |
| IGHE_RT_33_60_BIOTIN | AGTCACGGAGGTGGCAT (SEQ ID NO: 53)<br>/52-Bio/A*GTCACGGAGGTGGCAT (SEQ ID NO: 54) |
| IGHG_RT_18_59_BIOTIN | GACACCGTCACCGGTTC (SEQ ID NO: 55)<br>/52-Bio/G*ACACCGTCACCGGTTC (SEQ ID NO: 56) |
| IGM_RT_27_58_BIOTIN | GAAGGAAGTCCTGTGCGA (SEQ ID NO: 57)<br>/52-Bio/G*AAGGAAGTCCTGTGCGA (SEQ ID NO: 58) |
| IGLC_RT_72_major_60_BIOTIN | TTGACGGGGCTGCTATCT (SEQ ID NO: 59)<br>/52-Bio/T*TGACGGGGCTGCTATCT (SEQ ID NO: 60) |
| IGLC_RT_72_minor_59_BIOTIN | ACGGGGCTGCCATCT (SEQ ID NO: 61)<br>/52-Bio/A*CGGGGCTGCCATCT (SEQ ID NO: 62) |
| IGKC_RT_10_59_BIOTIN | CAGATTTCAACTGCTCATCAGA (SEQ ID NO: 63)<br>/52-Bio/C*AGATTTCAACTGCTCATCAGA (SEQ ID NO: 64) |

Reverse Transcriptase Primers (Alternative Design 1)

| Primer Name | Sequence (sequence with modified nucleotides shown beneath each) |
|---|---|
| IGHA_RT_4_59_BIOTIN | GGCTCCTGGGGGAAGA (SEQ ID NO: 49)<br>/52-Bio/G*GCTCCTGGGGGAAGA (SEQ ID NO: 50) |
| IGHD_RT_40_59_BIOTIN | GTACCCAGTTATCAAGCATGC (SEQ ID NO: 51)<br>/52-Bio/G*TACCCAGTTATCAAGCATGC (SEQ ID NO: 52) |
| IGHE_RT_33_60_BIOTIN | AGTCACGGAGGTGGCAT (SEQ ID NO: 53)<br>/52-Bio/A*GTCACGGAGGTGGCAT (SEQ ID NO: 54) |
| IGHG_PCR_4_58_BIOTIN | GGGAAGTAGTCCTTGACCA (SEQ ID NO: 65)<br>/52-Bio/G*GGAAGTAGTCCTTGACCA (SEQ ID NO: 66) |
| IGM_RT_27_58_BIOTIN | GAAGGAAGTCCTGTGCGA (SEQ ID NO: 57)<br>/52-Bio/G*AAGGAAGTCTGTGCGA (SEQ ID NO: 58) |
| IGLC_RT_72_major_60_BIOTIN | TTGACGGGGCTGCTATCT (SEQ ID NO: 59)<br>/52-Bio/T*TGACGGGGCTGCTATCT (SEQ ID NO: 60) |
| IGLC_RT_72_minor_59_BIOTIN | ACGGGGCTGCCATCT (SEQ ID NO: 61)<br>/52-Bio/A*CGGGGCTGCCATCT (SEQ ID NO: 62) |
| IGKC_RT_10_59_BIOTIN | CAGATTTCAACTGCTCATCAGA (SEQ ID NO: 63)<br>/52-Bio/C*AGATTTCAACTGCTCATCAGA (SEQ ID NO: 64) |

First PCR Gene-Specific Primers

| Primer Name | Sequence (sequence with tail shown beneath each) |
|---|---|
| IGHA_PCR_4_69 | AGGCTCAGCGGGAAGACCT (SEQ ID NO: 67)<br>AGACGTGTGCTCTTCCGATCTAGGCTCAGCGGGAAGACCT (SEQ ID NO: 68) |
| IGHD_PCR_27_69 | CAGGGCTGTTATCCTTTGGGTGTC (SEQ ID NO: 69)<br>AGACGTGTGCTCTTCCGATCTCAGGGCTGTTATCCTTTGGGTGTC (SEQ ID NO: 70) |
| IGHE_PCR_24_68 | GAGGTGGCATTGGAGGGAATGT (SEQ ID NO: 71)<br>AGACGTGTGCTCTTCCGATCTGAGGTGGCATTGGAGGGAATGT (SEQ ID NO: 72) |
| IGHG_PCR_4_69 | TTCGGGGAAGTAGTCCTTGACCA (SEQ ID NO: 73)<br>AGACGTGTGCTCTTCCGATCTTTCGGGGAAGTAGTCCTTGACCA (SEQ ID NO: 74) |
| IGHG_PCR_4_minor_69 | GGTTCTGGGAAGTAGTCCTTGACCA (SEQ ID NO: 75)<br>AGACGTGTGCTCTTCCGATCTGGTTCTGGGAAGTAGTCCTTGACCA (SEQ ID NO: 76) |
| IGM_PCR_17_69 | TCGTATCCGACGGGGAATTCTCAC (SEQ ID NO: 77)<br>AGACGTGTGCTCTTCCGATCTTCGTATCCGACGGGGAATTCTCAC (SEQ ID NO: 78) |
| IGKC_PCR_22_70 | TGCTCATCAGATGGCGGGAAGAT (SEQ ID NO: 79)<br>AGACGTGTGCTCTTCCGATCTTGCTCATCAGATGGCGGGAAGAT (SEQ ID NO: 80) |
| IGLC_PCR_17_major_69 | CCTTGTTGGCTTGAAGCTCCTCA (SEQ ID NO: 81)<br>AGACGTGTGCTCTTCCGATCTCCTTGTTGGCTTGAAGCTCCTCA (SEQ ID NO: 82) |
| IGLC_PCR_17_minor_68 | CTTGTTGGCTTGGAGCTCCTCA (SEQ ID NO: 83)<br>AGACGTGTGCTCTTCCGATCTCTTGTTGGCTTGGAGCTCCTCA (SEQ ID NO: 84) |

TABLE 8-continued

B Cell Receptor (IgH) Primer Panel

First PCR Gene-Specific Primers (Alternative Design 1)

| Primer Name | Sequence (sequence with tail shown beneath each) |
|---|---|
| IGHA_PCR_4_69 | AGGCTCAGCGGGAAGACCT (SEQ ID NO: 67) |
| | AGACGTGTGCTCTTCCGATCTAGGCTCAGCGGGAAGACCT (SEQ ID NO: 68) |
| IGHD_PCR_27_69 | CAGGGCTGTTATCCTTTGGGTGTC (SEQ ID NO: 69) |
| | AGACGTGTGCTCTTCCGATCTCAGGGCTGTTATCCTTTGGGTGTC (SEQ ID NO: 70) |
| IGHE_PCR_24_68 | GAGGTGGCATTGGAGGGAATGT (SEQ ID NO: 71) |
| | AGACGTGTGCTCTTCCGATCTGAGGTGGCATTGGAGGGAATGT (SEQ ID NO: 72) |
| IGHG1_p38_70.2 | CCCAGAGGTGCTCTTGGAGGAG (SEQ ID NO: 85) |
| | AGACGTGTGCTCTTCCGATCTCCCAGAGGTGCTCTTGGAGGAG (SEQ ID NO: 86) |
| IGHG2_4_p48_71.1 | GCTGTGCTCTCGGAGGTGCT (SEQ ID NO: 87) |
| | AGACGTGTGCTCTTCCGATCTGCTGTGCTCTCGGAGGTGCT (SEQ ID NO: 88) |
| IGHG3_p40_70.6 | CGGAGGTGCTCCTGGAGCA (SEQ ID NO: 89) |
| | AGACGTGTGCTCTTCCGATCTCGGAGGTGCTCCTGGAGCA (SEQ ID NO: 90) |
| IGM_PCR_17_69 | TCGTATCCGACGGGGAATTCTCAC (SEQ ID NO: 77) |
| | AGACGTGTGCTCTTCCGATCTTCGTATCCGACGGGGAATTCTCAC (SEQ ID NO: 78) |

First PCR Gene-Specific Primers (Alternative Design 2)

| Primer Name | Sequence (sequence with tail shown beneath each) |
|---|---|
| IGHA_universal | GCGA/ideoxyI/GACCACGTTCCCATCT (SEQ ID NO: 91) |
| | AGACGTGTGCTCTTCCGATCTGCGA/ideoxyI/GACCACGTTCCCATCT (SEQ ID NO: 92) |
| IGHA1_p54_69.0 | GCGATGACCACGTTCCCATCT (SEQ ID NO: 93) |
| | AGACGTGTGCTCTTCCGATCTGCGATGACCACGTTCCCATCT (SEQ ID NO: 94) |
| IGHA1_p54_69.7 | GCGATGACCACGTTCCCATCTG (SEQ ID NO: 95) |
| | AGACGTGTGCTCTTCCGATCTGCGATGACCACGTTCCCATCTG (SEQ ID NO: 96) |
| IGHA2_p54_71.1 | GCGACGACCACGTTCCCATCT (SEQ ID NO: 97) |
| | AGACGTGTGCTCTTCCGATCTGCGACGACCACGTTCCCATCT (SEQ ID NO: 98) |
| IGHA2_p54_70 | GCGACGACCACGTTCCCATC (SEQ ID NO: 99) |
| | AGACGTGTGCTCTTCCGATCTGCGACGACCACGTTCCCATC (SEQ ID NO: 100) |
| IGHA1_p43_70.1 | TTCCCATCTGGCTGGGTGCT (SEQ ID NO: 101) |
| | AGACGTGTGCTCTTCCGATCTTTCCCATCTGGCTGGGTGCT (SEQ ID NO: 102) |
| IGHA2_p43_70.2 | TTCCCATCTTGGGGGGTGCT (SEQ ID NO: 103) |
| | AGACGTGTGCTCTTCCGATCTTTCCCATCTTGGGGGGTGCT (SEQ ID NO: 104) |

First PCR Gene-Specific Primers (Alternative Design 3)

| Primer Name | Sequence (sequence with tail shown beneath each) |
|---|---|
| IGHD_PCR_27_69 | CAGGGCTGTTATCCTTTGGGTGTC (SEQ ID NO: 69) |
| | AGACGTGTGCTCTTCCGATCTCAGGGCTGTTATCCTTTGGGTGTC (SEQ ID NO: 70) |
| IGHE_PCR_24_68 | GAGGTGGCATTGGAGGGAATGT (SEQ ID NO: 71) |
| | AGACGTGTGCTCTTCCGATCTGAGGTGGCATTGGAGGGAATGT (SEQ ID NO: 72) |
| IGHG1_p38_70.2 | CCCAGAGGTGCTCTTGGAGGAG (SEQ ID NO: 85) |
| | AGACGTGTGCTCTTCCGATCTCCCAGAGGTGCTCTTGGAGGAG (SEQ ID NO: 86) |
| IGHG2_4_p48_71.1 | GCTGTGCTCTCGGAGGTGCT (SEQ ID NO: 87) |
| | AGACGTGTGCTCTTCCGATCTGCTGTGCTCTCGGAGGTGCT (SEQ ID NO: 88) |
| IGHG3_p40_70.6 | CGGAGGTGCTCCTGGAGCA (SEQ ID NO: 89) |
| | AGACGTGTGCTCTTCCGATCTCGGAGGTGCTCCTGGAGCA (SEQ ID NO: 90) |
| IGM_PCR_17_69 | TCGTATCCGACGGGGAATTCTCAC (SEQ ID NO: 77) |
| | AGACGTGTGCTCTTCCGATCTTCGTATCCGACGGGGAATTCTCAC (SEQ ID NO: 78) |

TABLE 9

B Cell Receptor (IgK/IgL) Primer Panel

Reverse Transcriptase Primers

| Primer Name | Sequence (sequence with modified nucleotides shown beneath each) |
|---|---|
| IGHA_RT_4_59_BIOTIN | GGCTCCTGGGGGAAGA (SEQ ID NO: 49) |
| | /52-Bio/G*GCTCCTGGGGGAAGA (SEQ ID NO: 50) |
| IGHD_RT_40_59_BIOTIN | GTACCCAGTTATCAAGCATGC (SEQ ID NO: 51) |
| | /52-Bio/G*TACCCAGTTATCAAGCATGC (SEQ ID NO: 52) |
| IGHE_RT_33_60_BIOTIN | AGTCACGGAGGTGGCAT (SEQ ID NO: 53) |
| | /52-Bio/A*GTCACGGAGGTGGCAT (SEQ ID NO: 54) |
| IGHG_RT_18_59_BIOTIN | GACACCGTCACCGGTTC (SEQ ID NO: 55) |
| | /52-Bio/G*ACACCGTCACCGGTTC (SEQ ID NO: 56) |
| IGM_RT_27_58_BIOTIN | GAAGGAAGTCCTGTGCGA (SEQ ID NO: 57) |
| | /52-Bio/G*AAGGAAGTCCTGTGCGA (SEQ ID NO: 58) |

TABLE 9-continued

| B Cell Receptor (IgK/IgL) Primer Panel | |
|---|---|
| IGLC_RT_72_major_60_BIOTIN | TTGACGGGGCTGCTATCT (SEQ ID NO: 59)<br>/52-Bio/T*TGACGGGGCTGCTATCT (SEQ ID NO: 60) |
| IGLC_RT_72_minor_59_BIOTIN | ACGGGGCTGCCATCT (SEQ ID NO: 61)<br>/52-Bio/A*CGGGGCTGCCATCT (SEQ ID NO: 62) |
| IGKC_RT_10_59_BIOTIN | CAGATTTCAACTGCTCATCAGA (SEQ ID NO: 63)<br>/52-Bio/C*AGATTTCAACTGCTCATCAGA (SEQ ID NO: 64) |

| Reverse Transcriptase Primers (Alternative Design 1) | |
|---|---|
| Primer Name | Sequence (sequence with modified nucleotides shown beneath each) |
| IGHA_RT_4_59_BIOTIN | GGCTCCTGGGGAAGA (SEQ ID NO: 49)<br>/52-Bio/G*GCTCCTGGGGAAGA (SEQ ID NO: 50) |
| IGHD_RT_40_59_BIOTIN | GTACCCAGITATCAAGCATGC (SEQ ID NO: 51)<br>/52-Bio/G*TACCCAGTTATCAAGCATGC (SEQ ID NO: 52) |
| IGHE_RT_33_60_BIOTIN | AGTCACGGAGGTGGCAT (SEQ ID NO: 53)<br>/52-Bio/A*GTCACGGAGGTGGCAT (SEQ ID NO: 54) |
| IGHG_PCR_4_58_BIOTIN | GGGAAGTAGTCCTTGACCA (SEQ ID NO: 65)<br>/52-Bio/G*GGAAGTAGTCCTTGACCA (SEQ ID NO: 66) |
| IGM_RT_27_58_BIOTIN | GAAGGAAGTCCTGTGCGA (SEQ ID NO: 57)<br>/52-Bio/G*AAGGAAGTCCTGTGCGA (SEQ ID NO: 58) |
| IGLC_RT_72_major_60_BIOTIN | TTGACGGGGCTGCTATCT (SEQ ID NO: 59)<br>/52-Bio/T*TGACGGGGCTGCTATCT (SEQ ID NO: 60) |
| IGLC_RT_72_minor_59_BIOTIN | ACGGGGCTGCCATCT (SEQ ID NO: 61)<br>/52-Bio/A*CGGGGCTGCCATCT (SEQ ID NO: 62) |
| IGKC_RT_10_59_BIOTIN | CAGATTTCAACTGCTCATCAGA (SEQ ID NO: 63)<br>/52-Bio/C*AGATTTCAACTGCTCATCAGA (SEQ ID NO: 64) |

| First PCR Gene-Specific Primers | |
|---|---|
| Primer Name | Sequence (sequence with tail shown beneath each) |
| IGKC_PCR_22_70 | TGCTCATCAGATGGCGGGAAGAT (SEQ ID NO: 79)<br>AGACGTGTGCTCTTCCGATCTTGCTCATCAGATGGCGGGAAGAT (SEQ ID NO: 80) |
| IGLC_PCR_17_major_69 | CCTTGTTGGCTTGAAGCTCCTCA (SEQ ID NO: 81)<br>AGACGTGTGCTCTTCCGATCTCCTTGTTGGCTTGAAGCTCCTCA (SEQ ID NO: 82) |
| IGLC_PCR_17_minor_68 | CTTGTTGGCTTGGAGCTCCTCA (SEQ ID NO: 83)<br>AGACGTGTGCTCTTCCGATCTCTTGTTGGCTTGGAGCTCCTCA (SEQ ID NO: 84) |

Figure 14:
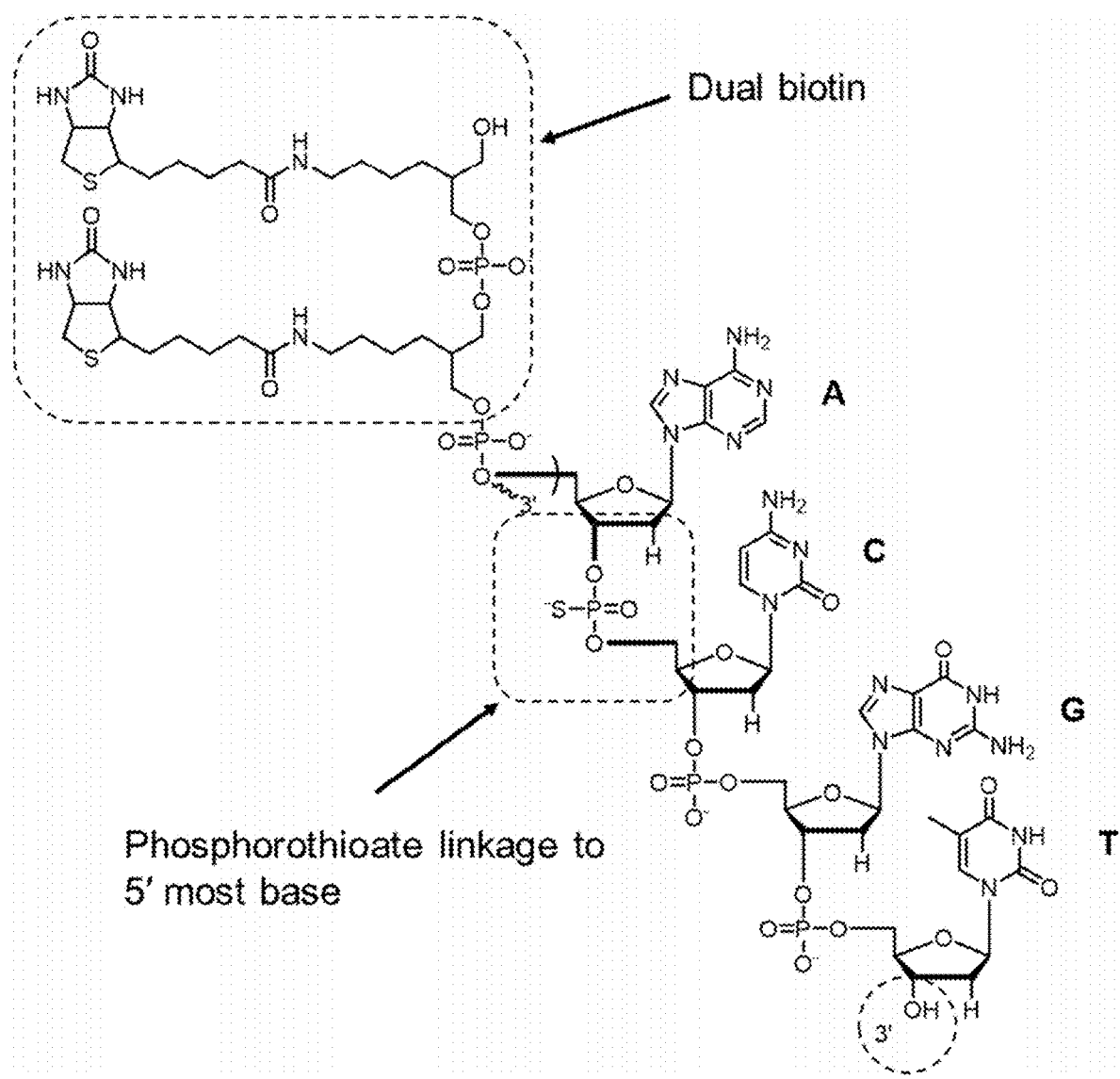
FIG. 14 is a schematic showing the structure of a reverse transcriptase (RT) primer.

The nucleotide sequences of the RT primers in Tables 6-9 are alternatively listed with modifications shown with notation according to Integrated DNA Technologies (IDT) nomenclature—where "*" denotes a phosphorothioate bond between the nucleotide preceding "*" and the nucleotide following "*" in the sequence, and "/52-Bio/" denotes a 5' dual biotin moiety. FIG. 14 shows an example of an RT primer having a 5' dual biotin moiety linked to the 5' most base ("A"), with a phosphorothioate bond between the 5' most base and the penultimate 5' most base ("C"). The dual biotin moiety allows selection of products of RT and ensures higher capture efficiency. However, it is possible to use a single biotin. The phosphorothioate linkage prevents degradation by exonuclease so as to ensure that the biotin-containing base is not removed.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of preparing nucleic acids for analysis, the method comprising:
   (a) contacting a nucleic acid molecule comprising a target nucleotide sequence with a capture moiety modified primer that specifically anneals to the target nucleotide sequence under hybridization conditions;
   (b) conducting a first strand synthesis reaction that is primed by a hybridized capture moiety modified primer and that uses the nucleic acid molecule as a template;
   (c) conducting a second strand synthesis reaction that uses a product of the first strand synthesis reaction as a template to generate a double-stranded nucleic acid comprising a capture moiety;
   (d) ligating an adapter nucleic acid to the double-stranded nucleic acid to produce a ligation product comprising the capture moiety;
   (e) capturing the ligation product by contacting the ligation product with a binding partner of the capture moiety; and
   (f) amplifying the captured ligation product by polymerase chain reaction using a target-specific primer that comprises a 3' portion that specifically anneals to the target nucleotide sequence and a first adapter primer that specifically anneals to a complementary sequence of the adapter nucleic acid, wherein the target-specific primer comprises a 5' tail portion that does not specifically anneal to the target nucleotide sequence.

2. The method of claim 1, further comprising:
   (g) amplifying an amplification product of step (f) by polymerase chain reaction using a tail primer that comprises a 3' portion that specifically anneals to a complementary sequence of the 5' tail portion of the target-specific primer and a second adapter primer that specifically anneals to a complementary sequence of the adapter nucleic acid, wherein the tail primer comprises a 5' portion that does not specifically anneal to a complementary sequence of the target-specific primer.

3. The method of claim 1, wherein:
   step (d) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid comprises a duplex portion and an overhang sequence, wherein the overhang sequence comprises a nucleotide sequence that is complementary to an overhang sequence at the 3' end of the double stranded nucleic acid; or
   step (d) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

4. The method of claim 1, wherein the capture moiety modified primer comprises at least one capture moiety modified nucleotide.

5. The method of claim 1, wherein the capture moiety is a biotin moiety.

6. The method of claim 1, wherein the binding partner is streptavidin.

7. The method of claim 1, wherein, in step (d), the double-stranded nucleic acid is ligated to the adapter nucleic acid in the presence of a crowding agent.

8. The method of claim 1, wherein:
   the second strand synthesis reaction is primed by a fragment of the nucleic acid molecule hybridized to the product of the first strand synthesis reaction; or
   the second strand synthesis is randomly primed using a plurality of random primers.

9. The method of claim 1, wherein the nucleic acid molecule comprises mRNA.

10. The method of claim 1, wherein the nucleic acid molecule is obtained from a sample comprising a T cell, a B cell, a leukocyte, or a mixture thereof.

11. The method of claim 10, wherein:
    the sample is obtained from a subject having, or suspected of having, a T cell malignancy or a B cell malignancy; or
    the sample is obtained from a subject that has undergone or will undergo transplantation; or
    the sample is obtained from a subject whose immune response to a treatment is being evaluated; or
    the sample is obtained from a subject having, or suspected of having, a white blood cell malignancy.

12. The method of claim 11, wherein the subject is a human or a chordate.

13. The method of claim 1, wherein the target nucleotide sequence comprises a nucleotide sequence corresponding to a portion of a T cell receptor (TCR) gene or a B cell receptor (BCR) gene.

14. The method of claim 1, wherein the capture moiety modified primer comprises a nucleotide sequence that is complementary to an immune receptor gene or an immunoglobulin gene.

15. The method of claim 14, wherein:
    the target-specific primer specifically anneals to a constant region or a J-segment that is downstream of a CDR3; or
    the target-specific primer specifically anneals to an exon-exon junction formed between a constant region and a J-segment, and wherein the exon-exon junction is downstream of a CDR3.

16. The method of claim 2, wherein:
    the first adapter primer and the second adapter primer are the same; or
    the first adapter primer and the second adapter primer are different; or
    the second adapter primer is nested relative to the first adapter primer.

17. The method of claim 2, wherein the 5' portion of the tail primer comprises at least one of a sample index region, a molecular barcode region, and a sequencing primer site region.

18. The method of claim 5, wherein the biotin moiety comprises biotin-triethylene glycol, bis-biotin, photocleavable biotin, desthiobiotin, desthiobiotin-triethylene glycol, or biotin azide.

19. The method of claim 6, wherein the streptavidin is attached to a substrate.

20. The method of claim 19, wherein the substrate comprises a solid surface.

21. The method of claim 20, wherein the solid surface comprises a paramagnetic bead.

22. The method of claim 8, wherein the plurality of random primers are between 6 bases in length and 15 bases in length.

23. The method of claim 11, wherein the T cell malignancy or the B cell malignancy is selected from the group consisting of lymphoma, multiple myeloma, acute lymphoblastic leukemia, and chronic lymphocytic leukemia.

24. The method of claim 14, wherein the capture moiety modified primer specifically anneals to a constant region that is downstream of a complementarity determining region 3 (CDR3).

* * * * *

SEQUENCE LISTING

```
<160> NUMBER OF SEQ ID NOS: 104

<210> SEQ ID NO 1
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 1
cactggattt agagtctctc agc                                           23

<210> SEQ ID NO 2
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond
```

```
<400> SEQUENCE: 2
cactggattt agagtctctc agc                                           23

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
gaacaccttg ttcaggtcct                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 4
gaacaccttg ttcaggtcct                                               20

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
gaacacgttt ttcaggtcct c                                             21

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 6
gaacacgttt ttcaggtcct c                                             21

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
```
tcttatatcc ttggggtaga attcc                                                25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 8
tcttatatcc ttggggtaga attcc                                                25

<210> SEQ ID NO 9
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 9
gggaaacatc tgcatcaagt tg                                                   22

<210> SEQ ID NO 10
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 10
gggaaacatc tgcatcaagt tg                                                   22

<210> SEQ ID NO 11
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 11
caggtcctct acaactgtga gtctgg                                               26

<210> SEQ ID NO 12
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 12
agacgtgtgc tcttccgatc tcaggtcctc tacaactgtg agtctgg                        47

```
<210> SEQ ID NO 13
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 13
ggtcctctac aacggttaac ctggtc                                              26

<210> SEQ ID NO 14
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 14
agacgtgtgc tcttccgatc tggtcctcta caacggttaa cctggtc                       47

<210> SEQ ID NO 15
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 15
ggtcctctac aacagtgagc caactt                                              26

<210> SEQ ID NO 16
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 16
agacgtgtgc tcttccgatc tggtcctcta caacagtgag ccaactt                       47

<210> SEQ ID NO 17
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 17
ggtcctccaa gacagagagc tgg                                                 23

<210> SEQ ID NO 18
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 18
agacgtgtgc tcttccgatc tggtcctcca agacagagag ctgg                          44

<210> SEQ ID NO 19
<211> LENGTH: 26
<212> TYPE: DNA
<213> ORGANISM: Artificial Sequence
<220> FEATURE:
<223> OTHER INFORMATION: Synthetic Polynucleotide
```

<400> SEQUENCE: 19
ggtcctctag gatggagagt cgagtc                                    26

<210> SEQ ID NO 20
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 20
agacgtgtgc tcttccgatc tggtcctcta ggatggagag tcgagtc             47

<210> SEQ ID NO 21
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 21
ggtcctctgt cacagtgagc ctg                                       23

<210> SEQ ID NO 22
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 22
agacgtgtgc tcttccgatc tggtcctctg tcacagtgag cctg                44

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
tctagcacgg tgagccgtgt                                           20

<210> SEQ ID NO 24
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 24
agacgtgtgc tcttccgatc ttctagcacg gtgagccgtg t                   41

<210> SEQ ID NO 25
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 25
cagtacggtc agcctagagc cttc                                      24

<210> SEQ ID NO 26
<211> LENGTH: 45

<212> TYPE: DNA
<213> ORGANISM: Artificial Sequence
<220> FEATURE:
<223> OTHER INFORMATION: Synthetic Polynucleotide

<400> SEQUENCE: 26
agacgtgtgc tcttccgatc tcagtacggt cagcctagag ccttc          45

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 27
ttcaggtcct cgagcactgt cag          23

<210> SEQ ID NO 28
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 28
agacgtgtgc tcttccgatc tttcaggtcc tcgagcactg tcag          44

<210> SEQ ID NO 29
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 29
ttcaggtcct ccagcactga gag          23

<210> SEQ ID NO 30
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 30
agacgtgtgc tcttccgatc tttcaggtcc tccagcactg agag          44

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
caggtcctcg agcaccagga          20

<210> SEQ ID NO 32
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 32
agacgtgtgc tcttccgatc tcaggtcctc gagcaccagg a    41

<210> SEQ ID NO 33
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 33
cagcacggtc agcctgct    18

<210> SEQ ID NO 34
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 34
agacgtgtgc tcttccgatc tcagcacggt cagcctgct    39

<210> SEQ ID NO 35
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 35
ttcaggtcct ctgtgaccgt gag    23

<210> SEQ ID NO 36
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 36
agacgtgtgc tcttccgatc tttcaggtcc tctgtgaccg tgag    44

<210> SEQ ID NO 37
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 37
acatctgcat caagttgttt atctgtgaca ac    32

<210> SEQ ID NO 38
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 38
agacgtgtgc tcttccgatc tacatctgca tcaagttgtt tatctgtgac aac    53

<210> SEQ ID NO 39
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 39
tgtttatctg taatgataag ctttgttccg gga                     33

<210> SEQ ID NO 40
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 40
agacgtgtgc tcttccgatc ttgtttatct gtaatgataa gctttgttcc ggga     54

<210> SEQ ID NO 41
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 41
tcaggtgaag ttactatgag cttagtccct                         30

<210> SEQ ID NO 42
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 42
agacgtgtgc tcttccgatc ttcaggtgaa gttactatga gcttagtccc t    51

<210> SEQ ID NO 43
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 43
gcgaagttac tatgagccta gtcccctt                           27

<210> SEQ ID NO 44
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 44
agacgtgtgc tcttccgatc tgcgaagtta ctatgagcct agtcccctt    48

<210> SEQ ID NO 45
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 45
tctctcagct ggtacacggc a                                  21

<210> SEQ ID NO 46
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 46
agacgtgtgc tcttccgatc ttctctcagc tggtacacgg ca    42

<210> SEQ ID NO 47
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 47
tcaccagaca agcgacattt gttcc    25

<210> SEQ ID NO 48
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 48
agacgtgtgc tcttccgatc ttcaccagac aagcgacatt tgttcc    46

<210> SEQ ID NO 49
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 49
ggctcctggg ggaaga    16

<210> SEQ ID NO 50
<211> LENGTH: 16
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 50
ggctcctggg ggaaga    16

<210> SEQ ID NO 51
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 51
gtacccagtt atcaagcatg c    21

<210> SEQ ID NO 52
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 52
gtacccagtt atcaagcatg c                                         21

<210> SEQ ID NO 53
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 53
agtcacggag gtggcat                                              17

<210> SEQ ID NO 54
<211> LENGTH: 17
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 54
agtcacggag gtggcat                                              17

<210> SEQ ID NO 55
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 55
gacaccgtca ccggttc                                              17

<210> SEQ ID NO 56
<211> LENGTH: 17
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)

```
<223> OTHER INFORMATION: Modified by a phosphorothioate bond

<400> SEQUENCE: 56
gacaccgtca ccggttc                                                    17

<210> SEQ ID NO 57
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 57
gaaggaagtc ctgtgcga                                                   18

<210> SEQ ID NO 58
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 58
gaaggaagtc ctgtgcga                                                   18

<210> SEQ ID NO 59
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 59
ttgacggggc tgctatct                                                   18

<210> SEQ ID NO 60
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 60
ttgacggggc tgctatct                                                   18

<210> SEQ ID NO 61
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 61
```
acggggctgc catct                                                         15

<210> SEQ ID NO 62
<211> LENGTH: 15
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 62
acggggctgc catct                                                         15

<210> SEQ ID NO 63
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 63
cagatttcaa ctgctcatca ga                                                 22

<210> SEQ ID NO 64
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:
<221> NAME/KEY: misc_feature
<222> LOCATION: (1)..(2)
<223> OTHER INFORMATION: Modified by a phosphorothioate bond

<400> SEQUENCE: 64
cagatttcaa ctgctcatca ga                                                 22

<210> SEQ ID NO 65
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 65
gggaagtagt ccttgacca                                                     19

<210> SEQ ID NO 66
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by biotin
<220> FEATURE:

```
<221> NAME/KEY: misc_feature
<222> LOCATION: (1)..(2)
<223> OTHER INFORMATION: Modified by a phosphorothioate bond

<400> SEQUENCE: 66
gggaagtagt ccttgacca                                              19

<210> SEQ ID NO 67
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 67
aggctcagcg ggaagacct                                              19

<210> SEQ ID NO 68
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 68
agacgtgtgc tcttccgatc taggctcagc gggaagacct                       40

<210> SEQ ID NO 69
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 69
cagggctgtt atcctttggg tgtc                                        24

<210> SEQ ID NO 70
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 70
agacgtgtgc tcttccgatc tcagggctgt tatcctttgg gtgtc                 45

<210> SEQ ID NO 71
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 71
gaggtggcat tggagggaat gt                                          22

<210> SEQ ID NO 72
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 72
agacgtgtgc tcttccgatc tgaggtggca ttggagggaa tgt                   43
```

<210> SEQ ID NO 73
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 73
ttcggggaag tagtccttga cca                                            23

<210> SEQ ID NO 74
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 74
agacgtgtgc tcttccgatc tttcggggaa gtagtccttg acca                     44

<210> SEQ ID NO 75
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 75
ggttctggga agtagtcctt gacca                                          25

<210> SEQ ID NO 76
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 76
agacgtgtgc tcttccgatc tggttctggg aagtagtcct tgacca                   46

<210> SEQ ID NO 77
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 77
tcgtatccga cggggaattc tcac                                           24

<210> SEQ ID NO 78
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 78
agacgtgtgc tcttccgatc ttcgtatccg acggggaatt ctcac                    45

<210> SEQ ID NO 79
<211> LENGTH: 23
<212> TYPE: DNA
<213> ORGANISM: Artificial Sequence
<220> FEATURE:

<223> OTHER INFORMATION: Synthetic Polynucleotide

<400> SEQUENCE: 79
tgctcatcag atggcgggaa gat                                         23

<210> SEQ ID NO 80
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 80
agacgtgtgc tcttccgatc ttgctcatca gatggcggga agat                  44

<210> SEQ ID NO 81
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 81
ccttgttggc ttgaagctcc tca                                         23

<210> SEQ ID NO 82
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 82
agacgtgtgc tcttccgatc tccttgttgg cttgaagctc ctca                  44

<210> SEQ ID NO 83
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 83
cttgttggct tggagctcct ca                                          22

<210> SEQ ID NO 84
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 84
agacgtgtgc tcttccgatc tcttgttggc ttggagctcc tca                   43

<210> SEQ ID NO 85
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 85
cccagaggtg ctcttggagg ag                                          22

<210> SEQ ID NO 86
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 86
agacgtgtgc tcttccgatc tcccagaggt gctcttggag gag        43

<210> SEQ ID NO 87
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 87
gctgtgctct cggaggtgct        20

<210> SEQ ID NO 88
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 88
agacgtgtgc tcttccgatc tgctgtgctc tcggaggtgc t        41

<210> SEQ ID NO 89
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 89
cggaggtgct cctggagca        19

<210> SEQ ID NO 90
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 90
agacgtgtgc tcttccgatc tcggaggtgc tcctggagca        40

<210> SEQ ID NO 91
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (4)..(5)
<223> OTHER INFORMATION: Modified by ideoxyI

<400> SEQUENCE: 91
gcgagaccac gttcccatct        20

<210> SEQ ID NO 92
<211> LENGTH: 41
<212> TYPE: DNA

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(26)
<223> OTHER INFORMATION: Modified by ideoxyI

<400> SEQUENCE: 92
agacgtgtgc tcttccgatc tgcgagacca cgttcccatc t                    41

<210> SEQ ID NO 93
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 93
gcgatgacca cgttcccatc t                                          21

<210> SEQ ID NO 94
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 94
agacgtgtgc tcttccgatc tgcgatgacc acgttcccat ct                   42

<210> SEQ ID NO 95
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 95
gcgatgacca cgttcccatc tg                                         22

<210> SEQ ID NO 96
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 96
agacgtgtgc tcttccgatc tgcgatgacc acgttcccat ctg                  43

<210> SEQ ID NO 97
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 97
gcgacgacca cgttcccatc t                                          21

<210> SEQ ID NO 98
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 98
agacgtgtgc tcttccgatc tgcgacgacc acgttcccat ct            42

<210> SEQ ID NO 99
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 99
gcgacgacca cgttcccatc                                     20

<210> SEQ ID NO 100
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 100
agacgtgtgc tcttccgatc tgcgacgacc acgttcccat c             41

<210> SEQ ID NO 101
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 101
ttcccatctg gctgggtgct                                     20

<210> SEQ ID NO 102
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 102
agacgtgtgc tcttccgatc tttcccatct ggctgggtgc t             41

<210> SEQ ID NO 103
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 103
ttcccatctt gggggtgct                                      20

<210> SEQ ID NO 104
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 104
agacgtgtgc tcttccgatc tttcccatct tggggggtgc t             41